US012653910B2

(12) United States Patent
Davidson et al.

(10) Patent No.: US 12,653,910 B2
(45) Date of Patent: Jun. 16, 2026

(54) ADENO-ASSOCIATED VIRAL VECTOR VARIANTS

(71) Applicant: The Children's Hospital of Philadelphia, Philadelphia, PA (US)

(72) Inventors: Beverly Davidson, Philadelphia, PA (US); Yonghong Chen, Philadelphia, PA (US); Paul T. Ranum, Philadelphia, PA (US); Xueyuan Liu, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 932 days.

(21) Appl. No.: 17/778,783

(22) PCT Filed: Nov. 20, 2020

(86) PCT No.: PCT/US2020/061464
§ 371 (c)(1),
(2) Date: May 20, 2022

(87) PCT Pub. No.: WO2021/102234
PCT Pub. Date: May 27, 2021

(65) Prior Publication Data
US 2023/0346981 A1      Nov. 2, 2023

Related U.S. Application Data

(60) Provisional application No. 63/084,709, filed on Sep. 29, 2020, provisional application No. 62/939,315, filed on Nov. 22, 2019.

(51) Int. Cl.
| | |
|---|---|
| *A61K 48/00* | (2006.01) |
| *A61P 25/00* | (2006.01) |
| *C07K 7/06* | (2006.01) |
| *C12N 15/86* | (2006.01) |

(52) U.S. Cl.
CPC .......... *A61K 48/0075* (2013.01); *A61P 25/00* (2018.01); *C07K 7/06* (2013.01); *C12N 15/86* (2013.01); *C12N 2750/14122* (2013.01); *C12N 2750/14143* (2013.01); *C12N 2750/14171* (2013.01)

(58) Field of Classification Search
CPC ..... A61K 48/0075; A61K 48/00; A61P 25/00; A61P 25/28; C07K 7/06; C07K 14/005; C07K 2319/33; C12N 15/86; C12N 2750/14122; C12N 2750/14143; C12N 2750/14171; C12N 2750/14145
See application file for complete search history.

(56) References Cited

U.S. PATENT DOCUMENTS

| | | | |
|---|---|---|---|
| 8,299,215 | B2 | 10/2012 | Davidson et al. |
| 8,691,948 | B2 | 4/2014 | Davidson et al. |
| 9,585,971 | B2 | 3/2017 | Deverman |
| 10,472,650 | B2 | 11/2019 | Davidson et al. |
| 2004/0031072 | A1 | 2/2004 | La Rosa et al. |
| 2013/0224836 | A1 | 8/2013 | Muramatsu |
| 2013/0330335 | A1 | 12/2013 | Bremel et al. |
| 2017/0029464 | A1 | 2/2017 | Körbelin et al. |
| 2019/0175763 | A1 | 6/2019 | Shapiro et al. |

FOREIGN PATENT DOCUMENTS

| | | | |
|---|---|---|---|
| KR | 10-2017-0086537 | 7/2017 | |
| KR | 10-2018-0097629 | 8/2018 | |
| KR | 10-2019-0034239 | 4/2019 | |
| WO | WO2003/052051 | 6/2003 | |
| WO | WO2006105392 | 10/2006 | |
| WO | WO2012057363 | 5/2012 | |
| WO | WO2015/038958 | 3/2015 | |
| WO | WO2016/081811 | 5/2016 | |
| WO | WO2017/100671 | 6/2017 | |
| WO | WO2018/022905 | 2/2018 | |
| WO | WO 2018/152333 | 8/2018 | |
| WO | WO 2018/209317 | 11/2018 | |
| WO | WO 2019/060454 | 3/2019 | |
| WO | WO 2019/067840 | 4/2019 | |
| WO | WO 2019/222329 | 11/2019 | |
| WO | WO-2020014471 A1 * | 1/2020 | ........... A61K 31/522 |
| WO | WO 2021/163556 | 8/2021 | |

OTHER PUBLICATIONS

Chen X et al. Fusion Protein Linkers: Property, design, and functionality. 2013. Advanced Drug Delivery Reviews. 65, 1357-1369. ( Year: 2013).*
Pham Q et al. Chemical approaches to probe and engineer AAV vectors. 2024. Nanoscale. 16. 13820-13833. (Year: 2024).*
Singh RK et al. Protein Engineering Approaches in the Post-Genomic Era. 2017. Current Protein and Peptide Science. 18, 1-11. ( Year: 2017).*
Zhang M et al. Propagated Perturbations from a Peripheral Mutation Show Interactions Supporting WW Domain Thermostability. 2018. Structure. 26, 1474-1485. (Year: 2018).*
Chen et al., Molecular signatures of disease brain endothelia provide new sites for CNS-directed enzyme therapy. Nat Med, 2009. 15(10): p. 1215-8.
Chen et al., Overcoming Limitations Inherent in Sulfamidase to Improve Mucopolysaccharidosis IIIA Gene Therapy. Mol Ther, 2018. 26(4): p. 1118-1126.
Deverman et al., Cre-dependent selection yields AAV variants for widespread gene transfer to the adult brain. Nat Biotechnol, 2016. 34(2): p. 204-9.

(Continued)

*Primary Examiner* — Paul J Holland
(74) *Attorney, Agent, or Firm* — pH IP Law

(57) ABSTRACT

Provided herein are targeting peptides and vectors containing a sequence that encodes the targeting peptides that deliver agents to specific substructures in the brain. Provided herein are viral vectors each comprising a modified capsid, wherein the modified capsid comprises at least one amino acid sequence that targets the viral vector to a distinct brain structure.

23 Claims, 22 Drawing Sheets

Specification includes a Sequence Listing.

(56) References Cited

OTHER PUBLICATIONS

Hartz et al., Isolation of Cerebral Capillaries from Fresh Human Brain Tissue. J Vis Exp, 2018(139).

Hordeaux et al., The Neurotropic Properties of AAV-PHP.B are Limited to C57BL/6J Mice. Mol Ther, 2018. 26(3): p. 664-668.

International Preliminary Report on Patentability issued in Patent Application No. PCT/US20/61464, dated May 27, 2022.

International Search Report issued in Patent Application No. PCT/US20/61464, dated Apr. 9, 2021.

Katz et al., AAV gene transfer delays disease onset in a TPP1-deficient canine model of the late infantile form of Batten disease. Sci Transl Med, 2015. 7(313): p. 313ra180.

Keiser et al., Broad distribution of ataxin 1 silencing in rhesus cerebella for spinocerebellar ataxia type 1 therapy. Brain, 2015. 138(Pt 12): p. 3555-66.

Koerber et al., DNA shuffling of adeno-associated virus yields functionally diverse viral progeny. Mol Ther, 2008. 16(10): p. 1703-9.

Matsuzaki et al., Intravenous administration of the adeno-associated virus-PHP.B capsid fails to upregulate transduction efficiency in the marmoset brain. Neurosci Lett, 2018. 665: p. 182-188.

McBride et al., Preclinical safety of RNAi-mediated HTT suppression in the rhesus macaque as a potential therapy for Huntington's disease. Mol Ther, 2011. 19(12): p. 2152-62.

Monteys et al., CRISPR/Cas9 Editing of the Mutant Huntingtin Allele In Vitro and In Vivo. Mol Ther, 2017. 25(1): p. 12-23.

Muller et al., Random peptide libraries displayed on adeno-associated virus to select for targeted gene therapy vectors. Nat Biotechnol, 2003. 21(9): p. 1040-6.

Schaffer & Maheshri, Directed evolution of AAV mutants for enhanced gene delivery. Conf Proc IEEE Eng Med Biol Soc, 2004. 5: p. 3520-3.

Zhong et al., Next generation of adeno-associated virus 2 vectors: point mutations in tyrosines lead to high-efficiency transduction at lower doses. Proc Natl Acad Sci U S A, 2008. 105(22): p. 7827-32.

Chekhonin et al., "Targeted Transport of Genetic Material into Brain" *Biootechnology*, 5, 14-23, 2007.

Dalton et al., "Multiple Myeloma" *American Society of Hematology*, 2001, 157-177.

Lundberg et al., "Direct delivery of leptin to the hypothalamus using recombinant adeno-associated virus vectors results in increased therapeutic efficacy", *Nature Biotechnology*, 19, 169-172, 2001.

Muller et al., "Spliceosomal Peptide P140 for Immunotherapy of Systemic Lupus Erythematosus" *Arthritis & Rheumatism*, 58(12):3873-3883, 2008.

Pires et al. "Old and new challenges in Parkinson's disease therapeutics", *Progress in Neurobiology*, 156, 69-89, 2017.

Schwab et al., "Dopamine and Huntington's disease", *Expert Rev. Neurother*, 15(4):445-458, 2015.

Smirnova et al., "Structure of the nervous system", *Human anatomy. Nervous system: educational manual, MSEI named after A.D. Sakharov BSU*, 2018.

Zhou et al., "Mitochondria-homing peptide functionalized nanoparticles performing dual extracellular/intracellular roles to inhibit aminoglycosides induced ototoxicity", *Artificial Cells, Nanomedicine, and Biotechnologyi*, 46(2), 2018.

Zvěřová "Clinical aspects of Alzheimer's disease", *Clinical Biochemistry*, 72, 3-6, 2019.

Extended European Search Report for EP Application No. 20890214.8 dated Dec. 11, 2023, 9 pages.

Lee et al. "Adeno-Associated Virus (AAV) Vectors: Rational Design Strategies for Capsid Engineering", *Curr Opin Biomed Eng.*, 7:58-63, 2018.

Stover et al., "Transduction of the contralateral ear after adenovirus-mediated cochlear gene transfer", *Gene Therapy*, 7, 377-383, 2000.

Office Action for Korean Application No. 10-2022-7021143 dated Sep. 19, 2025; 8 pages, inclusive of machine translation to English.

Office Action for Columbian Application No. NC2022/0008507 dated Aug. 8, 2025; 20 pages, inclusive of machine translation to English.

Office Action for Singapore Application No. 11202205339R dated Sep. 19, 2025, 13 pages.

Büning et al., "Capsid Modifications for Targeting and Improving the Efficacy of AAV Vectors", *Molecular Therapy Methods & Clinical Development*, 12, 248-265, 2019.

Office Action for Canadian Application No. 3,159,113 dated Mar. 24, 2026, 8 pages.

* cited by examiner

AAV Peptide Display Library
Random heptapeptide
AAV genome showing the insertion of
random heptapeptide into AAV serotype
1, 2 and 9 capsid.
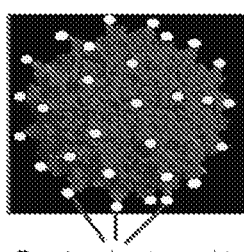
Random heptapeptide
The topology of AAV capsids (red) showing the
insertion of random heptapeptide (yellow) to
the capsid surface.
FIG. 1

FIG. 4

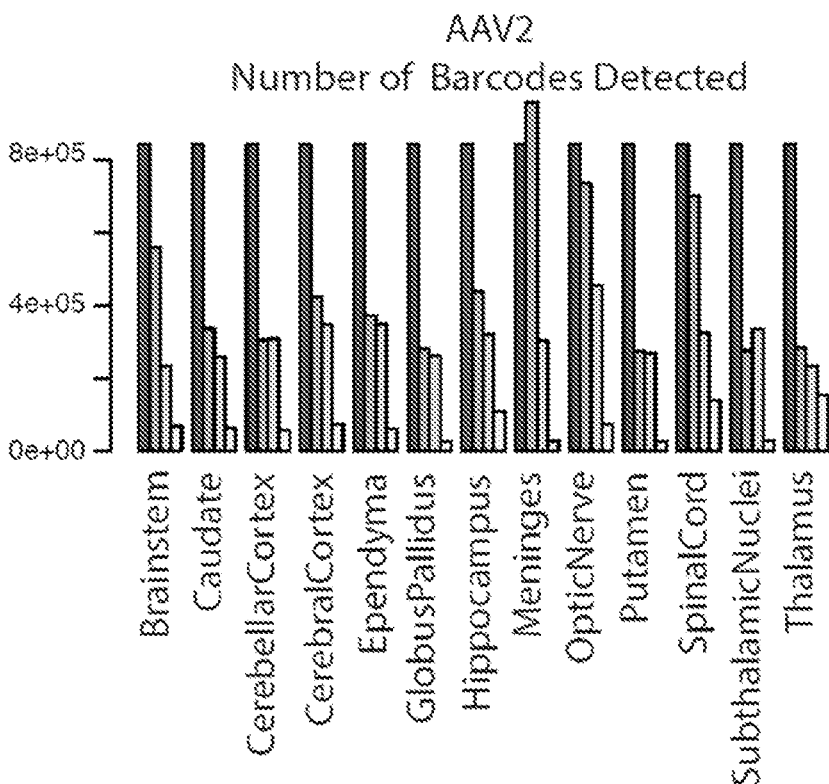
FIG. 4, con't.

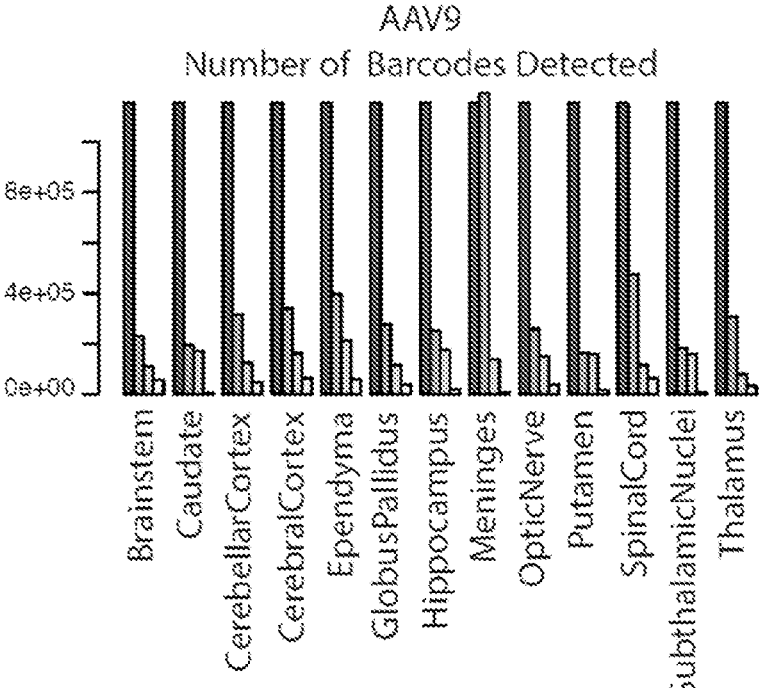
FIG. 4, con't.

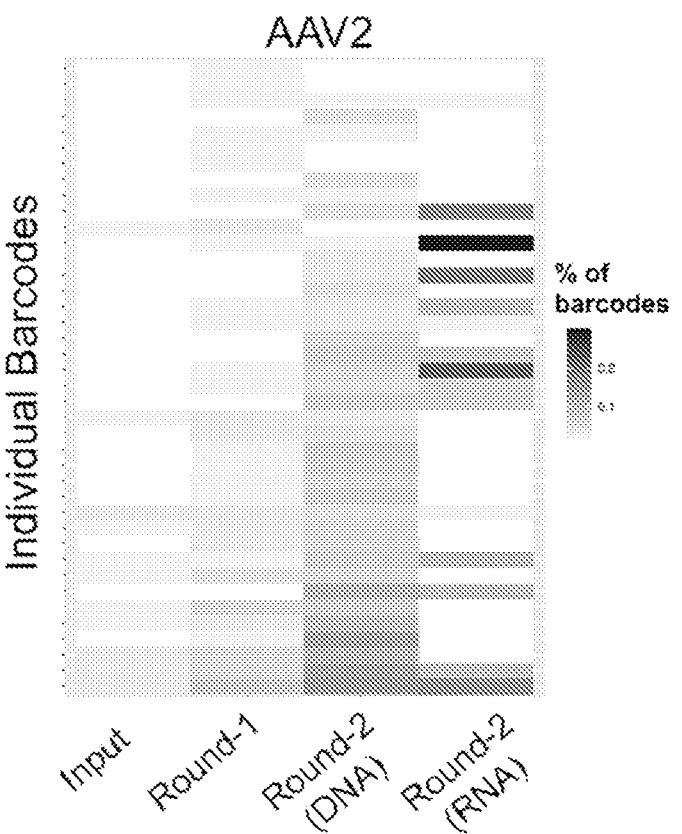
FIG. 5, con't.

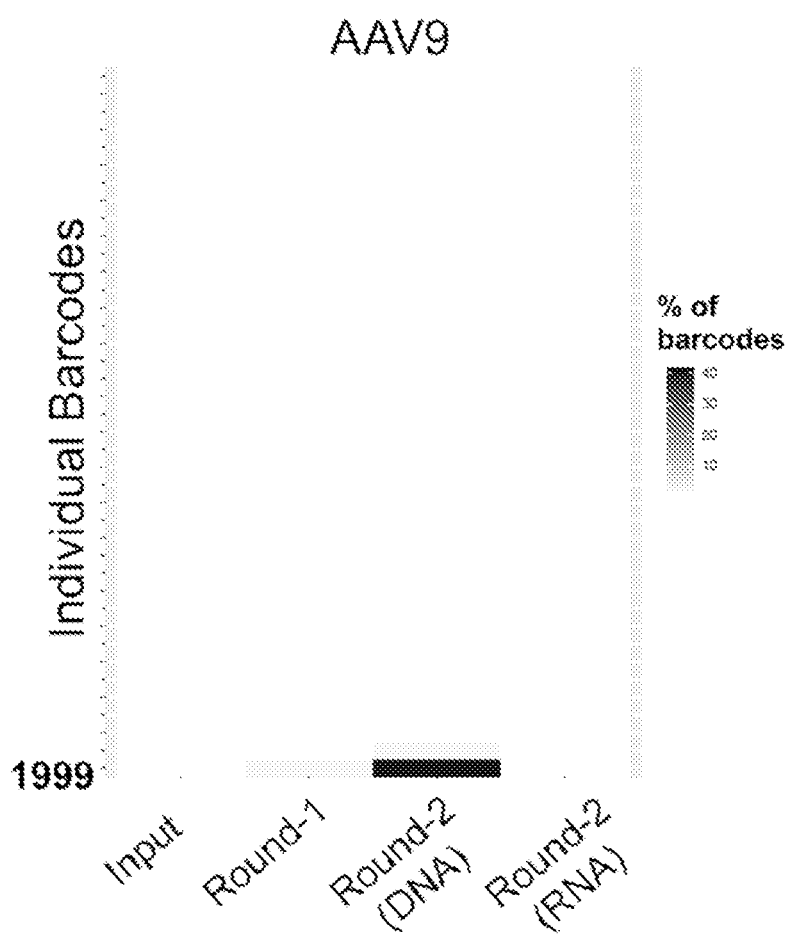
FIG. 5, con't.

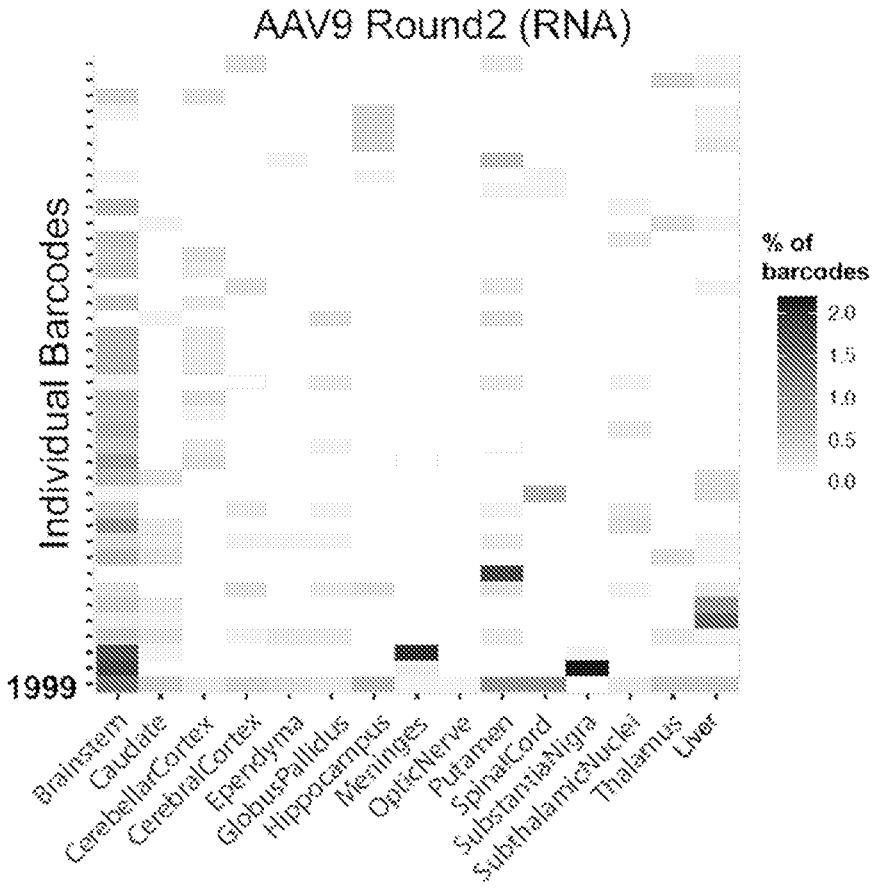
FIG. 6, con't.

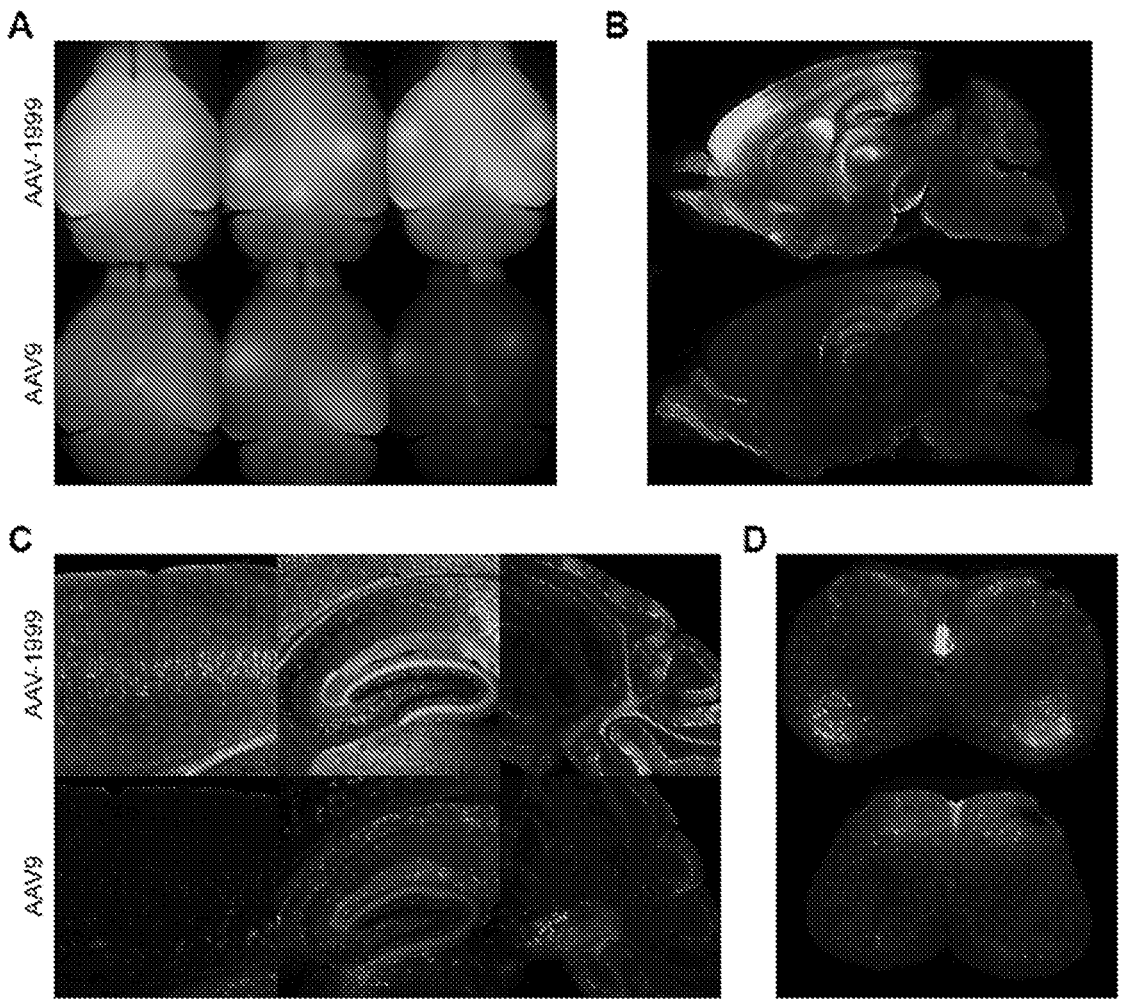
FIGS. 9A-D

Inner Hair Cell Transduction Visible

SEQUENCE LISTING

<160> NUMBER OF SEQ ID NOS: 144

<210> SEQ ID NO 1
<211> LENGTH: 7
<212> TYPE: PRT

-continued

<213> ORGANISM: Artificial Sequence
<220> FEATURE:
<223> OTHER INFORMATION: Synthetic polypeptide

<400> SEQUENCE: 1

Arg Pro Gly Arg Glu Gln Ala
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 2

Arg Gly Val Leu Val Thr Thr
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 3

Arg Pro Gly Arg Glu Ser Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 4

Asn Glu Ser Leu Lys Lys Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 5

Asp Lys Thr Arg Ala Gly Ser
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 6

Thr Ala Lys Ser Lys Gln Ala
1               5

<210> SEQ ID NO 7
<211> LENGTH: 7
<212> TYPE: PRT
<213> ORGANISM: Artificial Sequence -continued

```
<220> FEATURE:
<223> OTHER INFORMATION: Synthetic polypeptide

<400> SEQUENCE: 7

Pro Val Lys Lys Lys Asp Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 8

Gly Arg Glu Thr Leu Lys Gly
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 9

Pro Ile Pro Ala Gly Lys Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 10

Asn Val Val Arg Ala Gly Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 11

Lys Ala Thr Ala Asn Thr Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 12

Arg Asp Ala Thr Arg Ser Ser
1               5

<210> SEQ ID NO 13
<211> LENGTH: 7
<212> TYPE: PRT
<213> ORGANISM: Artificial Sequence
<220> FEATURE:
```

-continued

<223> OTHER INFORMATION: Synthetic polypeptide

<400> SEQUENCE: 13

Val Pro Thr Lys Ser Pro Lys
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 14

Ala Gly Val Ala Arg Ser Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 15

Arg Ser Arg Ser Glu Val Leu
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 16

Glu Val Lys Gly Lys Gly Lys
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 17

Ala Lys Leu Asn Lys Ser Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 18

Asn Ser Val His Asn Thr Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic polypeptide -continued

```
<400> SEQUENCE: 19

Asn Val Val Arg Gly Gly Ala
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 20

Asn Arg Leu Val Ala Gly Gly
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 21

Glu Arg Asp Arg Thr Arg Gly
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 22

Val Gln Gly Ser Lys Met Lys
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 23

Asn Ser Val Arg Pro Leu Thr
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 24

Asn Lys Ile His Ala Asn Pro
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic polypeptide
```

```
<400> SEQUENCE: 25

Thr Ala Pro Lys Ser Leu Lys
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 26

Arg Asp Ser Thr Arg Gln Leu
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 27

Asn Ser Val Lys Ser Val Leu
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 28

Asn Val Thr Ile Lys Ser Lys
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 29

Val Ser Leu Lys Glu Arg Val
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 30

Asp Glu Thr Ser Arg Leu Val
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 31
```

```
Asp Arg Leu Lys Gly Ile Val
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 32

Ser Gly Val Leu Val Gln Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 33

Ser Gly Thr Phe Val Lys Ala
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 34

Asn Ser Ile Ala Arg Pro Val
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 35

Asn Arg Ala Arg Ala Gly Glu
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 36

Ala Arg His Ala Leu Gly Gly
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 37
```

```
His Ser Ser Arg Pro Val Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 38

Lys Thr Gly Thr Ala Arg Leu
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 39

Val Lys Ala Leu Gly Arg Pro
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 40

Asn Asp Val Arg Ala Lys Gly
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 41

Gln Gly Val Leu Val Val Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 42

Lys Gln Tyr Ala Gly Ser Gln
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 43

Thr Asn Arg Met Ala Leu Ser
```

```
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 44

Gly Ile Thr Leu Gly Arg Leu
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 45

Ala Gly Ile Met Val Arg Val
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 46

Lys Ala Ala Gly Arg Thr Val
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 47

His Val Ile Arg Leu Pro Ser
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 48

Ser Val Ala Ser Ala Lys Lys
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 49

Thr Ala Thr Pro Arg Lys Gly
1               5
```

-continued

```
<210> SEQ ID NO 50
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 50

Thr Lys Thr Gly Leu Lys Leu
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 51

Lys Gly Leu Arg Thr Pro Thr
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 52

Leu Thr Ser Arg Thr Ser Pro
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 53

Asp Asp Pro Ser Ala Arg Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 54

Gly Glu Gln Asp Leu Arg Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 55

Val Ser Thr Ala Leu Pro Arg
1               5
```

-continued

<210> SEQ ID NO 56
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 56

Arg Asp Asp Val Pro Leu Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 57

Thr Arg Val Gly Thr Ala Gly
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 58

Ser Ser Ser Lys Thr Gly Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 59

Ser Leu Ser Thr Gly Pro Lys
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 60

Val Gln Gly Arg Gln Gly Gly
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 61

Arg Gly Ala Ser Gly Ala Val
1               5

```
<210> SEQ ID NO 62
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 62

Asn Ala Arg Ala Gln Gly Val
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 63

Thr Ser Asn Arg Gly Gln Val
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 64

Ala Val Arg Gly Gly Met Ala
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 65

Arg Gly Leu Asp Lys Gly Thr
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 66

Lys Gly Val Asp Leu Lys Pro
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 67

Thr Ala Val Arg Glu Glu Arg
1               5

<210> SEQ ID NO 68
```

```
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 68

Gly Asn Ala Gly Ile Thr Lys
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 69

Ser Ala Arg Ala Gly Ala Pro
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 70

Ser Gly Glu Phe Val Gly Arg
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 71

Ser Gly Arg Lys Leu Glu Val
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 72

Ser Ala Arg Ser Gly Ser Val
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 73

Glu Ser Thr Gly Arg Glu Arg
1               5

<210> SEQ ID NO 74
<211> LENGTH: 7
```

-continued

```
<212> TYPE: PRT
<213> ORGANISM: Artificial Sequence
<220> FEATURE:
<223> OTHER INFORMATION: Synthetic polypeptide

<400> SEQUENCE: 74

Val Thr Gln Ser Lys Gly Ala
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 75

Arg Gly Ser Gly Ser Ala Val
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 76

Asn Ala Arg Pro Val Ser Ala
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 77

Thr Ala Arg Gly Gly Gly Gly
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 78

Gly Arg Ser Ala Ser Gly Ser
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 79

Lys Ala Gln Gly Val Gly Gly
1               5

<210> SEQ ID NO 80
<211> LENGTH: 7
<212> TYPE: PRT
```

```
<213> ORGANISM: Artificial Sequence
<220> FEATURE:
<223> OTHER INFORMATION: Synthetic polypeptide

<400> SEQUENCE: 80

Gly Arg Gly Ala Pro Gly Gly
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 81

Val Pro Gly Arg Thr Ala Gly
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 82

Ala Arg Gly Ser Gly Val Asn
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 83

Ser Val Arg Val Gly Gly Gln
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 84

Arg Ala Val Pro Ala Gly Gly
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 85

Val Met Ser Ser Gly Lys Pro
1               5

<210> SEQ ID NO 86
<211> LENGTH: 7
<212> TYPE: PRT
<213> ORGANISM: Artificial Sequence
```

```
<220> FEATURE:
<223> OTHER INFORMATION: Synthetic polypeptide

<400> SEQUENCE: 86

Ser Thr Pro Ala Pro Lys Ser
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 87

Arg Gly Gly Ala Gln Val Val
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 88

Lys Ala Ser Gly Ala Gly Gly
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 89

Thr Gly Thr Ala Gly Leu Lys
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 90

Arg Ser Asn Ala Pro Gln Thr
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 91

Glu Ala Gln Ser His Pro Arg
1               5

<210> SEQ ID NO 92
<211> LENGTH: 7
<212> TYPE: PRT
<213> ORGANISM: Artificial Sequence
<220> FEATURE:
```

-continued

<223> OTHER INFORMATION: Synthetic polypeptide

<400> SEQUENCE: 92

Thr Lys Ser Leu Ser Ser Gly
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 93

Ala Ala Gly Ala Lys Val Met
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 94

Arg Gly Ser Thr Gln Val Gly
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 95

Gly Arg Ser Thr Gly Met Thr
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 96

Arg Ala Thr Ser Gln Ser Thr
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 97

Val Gly Arg Ser Val Gly Ala
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic polypeptide -continued

```
<400> SEQUENCE: 98

Gly Glu Gly Gly Gly Gly Arg
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 99

Thr Ala Ala Gly Gly Gln Arg
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 100

Gly Arg Gly Gly Ala Ala Leu
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 101

Val Ala Pro Ile Ser Lys Ser
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 102

Ala Pro Pro Val Lys Leu Ser
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 103

His Asp Gly Gly Ala Ser Arg
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic polypeptide
```

```
<400> SEQUENCE: 104

Arg Ser Gly Gly Ala Ala Val
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 105

Gly Ser Arg Ala Gly Val Gly
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 106

Lys Leu Ser Ile Ser Gly Asn
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 107

Gly Ala Val Gly Gly Val Lys
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 108

Lys Asn Glu Ser Gly Lys Val
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 109

Ala Gly Gln Leu Ala Gly Arg
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 110
```

Lys Gly Gly Gly Phe His Gly
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 111

Arg Ala Lys Pro Gly Met Glu
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 112

Gly Arg Asp Val Thr Arg Ser
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 113

Arg Gly Asp Leu Gln Trp Val
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 114

Gly Gly Asp Arg Thr Arg Gly
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 115

Arg Gly Asp Leu Ala Ser Val
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 116

```
Arg Asp Thr Thr Arg Asn Leu
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 117

Lys Gly Gly Gly Val His Gly
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 118

Arg Gly Asp Met Tyr Arg Val
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 119

Arg Gly Asp Arg Pro Val Ser
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 120

Arg Ser Asp Val Gly Ser Leu
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 121

Ala Gly Val Lys Pro Gly Arg
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 122

Arg Gly Asp Trp Pro Arg Gly
```

```
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 123

Gly Gly Arg Pro Gly Ser Trp
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 124

Arg Gly Asp Tyr Pro Arg Ser
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 125

Arg Gly Asp Leu Arg Phe Ile
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 126

Arg Gly Gly Gly Val Tyr Gly
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 127

Gly Ala Asp Arg Thr Arg Gly
1               5

<210> SEQ ID NO 128
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 128

Arg Gly Asp Phe Met Gly Leu
1               5
```

```
<210> SEQ ID NO 129
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 129

Arg Arg Asp Glu Thr Arg Thr
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 130

Ala Glu Ser Pro Trp Glu Arg
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 131

Ala Trp Asp Gly Thr Arg Val
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 132

Ala Arg Gly Asp Gly Trp Arg
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 133

Gly Arg Asp Tyr Thr Arg Leu
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 134

Arg Arg Gly Asp Ala Trp Ser
1               5
```

<210> SEQ ID NO 135
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 135

Met Asp Leu Thr Lys Ala Val
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 136

Met Met Gly Arg Pro Gly Arg
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 137

Thr Gly Arg Pro Gly Val Trp
1               5

<210> SEQ ID NO 138
<211> LENGTH: 736
<212> TYPE: PRT
<213> ORGANISM: adeno-associated virus 1

<400> SEQUENCE: 138

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

```
Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590
```

-continued

```
Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 139
<211> LENGTH: 735
<212> TYPE: PRT
<213> ORGANISM: adeno-associated virus 2

<400> SEQUENCE: 139

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
                20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
        100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
        130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Met Gly Asp Arg Val Ile
225                 230                 235                 240
```

```
Thr Thr Ser Thr Arg Thr Trp Ala Leu Pro Thr Tyr Asn Asn His Leu
            245             250                 255

Tyr Lys Gln Ile Ser Ser Gln Ser Gly Ala Ser Asn Asp Asn His Tyr
            260             265                 270

Phe Gly Tyr Ser Thr Pro Trp Gly Tyr Phe Asp Phe Asn Arg Phe His
            275             280             285

Cys His Phe Ser Pro Arg Asp Trp Gln Arg Leu Ile Asn Asn Asn Trp
    290             295                 300

Gly Phe Arg Pro Lys Arg Leu Asn Phe Lys Leu Phe Asn Ile Gln Val
305             310             315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
            340             345             350

Val Leu Gly Ser Ala His Gln Gly Cys Leu Pro Pro Phe Pro Ala Asp
            355             360             365

Val Phe Met Val Pro Gln Tyr Gly Tyr Leu Thr Leu Asn Asn Gly Ser
    370             375             380

Gln Ala Val Gly Arg Ser Ser Phe Tyr Cys Leu Glu Tyr Phe Pro Ser
385             390             395                 400

Gln Met Leu Arg Thr Gly Asn Asn Phe Thr Phe Ser Tyr Thr Phe Glu
            405             410             415

Asp Val Pro Phe His Ser Ser Tyr Ala His Ser Gln Ser Leu Asp Arg
            420             425             430

Leu Met Asn Pro Leu Ile Asp Gln Tyr Leu Tyr Tyr Leu Ser Arg Thr
            435             440             445

Asn Thr Pro Ser Gly Thr Thr Thr Gln Ser Arg Leu Gln Phe Ser Gln
    450             455             460

Ala Gly Ala Ser Asp Ile Arg Asp Gln Ser Arg Asn Trp Leu Pro Gly
465             470             475                 480

Pro Cys Tyr Arg Gln Gln Arg Val Ser Lys Thr Ser Ala Asp Asn Asn
            485             490             495

Asn Ser Glu Tyr Ser Trp Thr Gly Ala Thr Lys Tyr His Leu Asn Gly
            500             505             510

Arg Asp Ser Leu Val Asn Pro Gly Pro Ala Met Ala Ser His Lys Asp
            515             520             525

Asp Glu Glu Lys Phe Phe Pro Gln Ser Gly Val Leu Ile Phe Gly Lys
    530             535             540

Gln Gly Ser Glu Lys Thr Asn Val Asp Ile Glu Lys Val Met Ile Thr
545             550             555                 560

Asp Glu Glu Glu Ile Arg Thr Thr Asn Pro Val Ala Thr Glu Gln Tyr
            565             570             575

Gly Ser Val Ser Thr Asn Leu Gln Arg Gly Asn Arg Gln Ala Ala Thr
            580             585             590

Ala Asp Val Asn Thr Gln Gly Val Leu Pro Gly Met Val Trp Gln Asp
    595             600             605

Arg Asp Val Tyr Leu Gln Gly Pro Ile Trp Ala Lys Ile Pro His Thr
    610             615             620

Asp Gly His Phe His Pro Ser Pro Leu Met Gly Gly Phe Gly Leu Lys
625             630             635                 640

His Pro Pro Pro Gln Ile Leu Ile Lys Asn Thr Pro Val Pro Ala Asn
            645             650             655
```

-continued

```
Pro Ser Thr Thr Phe Ser Ala Ala Lys Phe Ala Ser Phe Ile Thr Gln
            660             665             670

Tyr Ser Thr Gly Gln Val Ser Val Glu Ile Glu Trp Glu Leu Gln Lys
            675             680             685

Glu Asn Ser Lys Arg Trp Asn Pro Glu Ile Gln Tyr Thr Ser Asn Tyr
            690             695             700

Asn Lys Ser Val Asn Val Asp Phe Thr Val Asp Thr Asn Gly Val Tyr
705             710             715             720

Ser Glu Pro Arg Pro Ile Gly Thr Arg Tyr Leu Thr Arg Asn Leu
            725             730             735

<210> SEQ ID NO 140
<211> LENGTH: 736
<212> TYPE: PRT
<213> ORGANISM: adeno-associated virus 9

<400> SEQUENCE: 140

Met Ala Ala Asp Gly Tyr Leu Pro Asp Trp Leu Glu Asp Asn Leu Ser
1               5               10              15

Glu Gly Ile Arg Glu Trp Trp Ala Leu Lys Pro Gly Ala Pro Gln Pro
            20              25              30

Lys Ala Asn Gln Gln His Gln Asp Asn Ala Arg Gly Leu Val Leu Pro
            35              40              45

Gly Tyr Lys Tyr Leu Gly Pro Gly Asn Gly Leu Asp Lys Gly Glu Pro
            50              55              60

Val Asn Ala Ala Asp Ala Ala Ala Leu Glu His Asp Lys Ala Tyr Asp
65              70              75              80

Gln Gln Leu Lys Ala Gly Asp Asn Pro Tyr Leu Lys Tyr Asn His Ala
            85              90              95

Asp Ala Glu Phe Gln Glu Arg Leu Lys Glu Asp Thr Ser Phe Gly Gly
            100             105             110

Asn Leu Gly Arg Ala Val Phe Gln Ala Lys Lys Arg Leu Leu Glu Pro
            115             120             125

Leu Gly Leu Val Glu Glu Ala Ala Lys Thr Ala Pro Gly Lys Lys Arg
            130             135             140

Pro Val Glu Gln Ser Pro Gln Glu Pro Asp Ser Ser Ala Gly Ile Gly
145             150             155             160

Lys Ser Gly Ala Gln Pro Ala Lys Lys Arg Leu Asn Phe Gly Gln Thr
            165             170             175

Gly Asp Thr Glu Ser Val Pro Asp Pro Gln Pro Ile Gly Glu Pro Pro
            180             185             190

Ala Ala Pro Ser Gly Val Gly Ser Leu Thr Met Ala Ser Gly Gly Gly
            195             200             205

Ala Pro Val Ala Asp Asn Asn Glu Gly Ala Asp Gly Val Gly Ser Ser
            210             215             220

Ser Gly Asn Trp His Cys Asp Ser Gln Trp Leu Gly Asp Arg Val Ile
225             230             235             240

Thr Thr Ser Thr Arg Thr Trp Ala Leu Pro Thr Tyr Asn Asn His Leu
            245             250             255

Tyr Lys Gln Ile Ser Asn Ser Thr Ser Gly Gly Ser Ser Asn Asp Asn
            260             265             270

Ala Tyr Phe Gly Tyr Ser Thr Pro Trp Gly Tyr Phe Asp Phe Asn Arg
            275             280             285

Phe His Cys His Phe Ser Pro Arg Asp Trp Gln Arg Leu Ile Asn Asn
            290             295             300
```

```
Asn Trp Gly Phe Arg Pro Lys Arg Leu Asn Phe Lys Leu Phe Asn Ile
305                 310             315             320

Gln Val Lys Glu Val Thr Asp Asn Asn Gly Val Lys Thr Ile Ala Asn
                325             330             335

Asn Leu Thr Ser Thr Val Gln Val Phe Thr Asp Ser Asp Tyr Gln Leu
            340             345             350

Pro Tyr Val Leu Gly Ser Ala His Glu Gly Cys Leu Pro Pro Phe Pro
            355             360             365

Ala Asp Val Phe Met Ile Pro Gln Tyr Gly Tyr Leu Thr Leu Asn Asp
        370             375             380

Gly Ser Gln Ala Val Gly Arg Ser Ser Phe Tyr Cys Leu Glu Tyr Phe
385             390             395             400

Pro Ser Gln Met Leu Arg Thr Gly Asn Asn Phe Gln Phe Ser Tyr Glu
                405             410             415

Phe Glu Asn Val Pro Phe His Ser Ser Tyr Ala His Ser Gln Ser Leu
            420             425             430

Asp Arg Leu Met Asn Pro Leu Ile Asp Gln Tyr Leu Tyr Tyr Leu Ser
            435             440             445

Lys Thr Ile Asn Gly Ser Gly Gln Asn Gln Gln Thr Leu Lys Phe Ser
        450             455             460

Val Ala Gly Pro Ser Asn Met Ala Val Gln Gly Arg Asn Tyr Ile Pro
465             470             475             480

Gly Pro Ser Tyr Arg Gln Gln Arg Val Ser Thr Thr Val Thr Gln Asn
                485             490             495

Asn Asn Ser Glu Phe Ala Trp Pro Gly Ala Ser Ser Trp Ala Leu Asn
            500             505             510

Gly Arg Asn Ser Leu Met Asn Pro Gly Pro Ala Met Ala Ser His Lys
            515             520             525

Glu Gly Glu Asp Arg Phe Phe Pro Leu Ser Gly Ser Leu Ile Phe Gly
        530             535             540

Lys Gln Gly Thr Gly Arg Asp Asn Val Asp Ala Asp Lys Val Met Ile
545             550             555             560

Thr Asn Glu Glu Glu Ile Lys Thr Thr Asn Pro Val Ala Thr Glu Ser
                565             570             575

Tyr Gly Gln Val Ala Thr Asn His Gln Ser Ala Gln Ala Gln Ala Gln
            580             585             590

Thr Gly Trp Val Gln Asn Gln Gly Ile Leu Pro Gly Met Val Trp Gln
            595             600             605

Asp Arg Asp Val Tyr Leu Gln Gly Pro Ile Trp Ala Lys Ile Pro His
        610             615             620

Thr Asp Gly Asn Phe His Pro Ser Pro Leu Met Gly Gly Phe Gly Met
625             630             635             640

Lys His Pro Pro Pro Gln Ile Leu Ile Lys Asn Thr Pro Val Pro Ala
                645             650             655

Asp Pro Pro Thr Ala Phe Asn Lys Asp Lys Leu Asn Ser Phe Ile Thr
            660             665             670

Gln Tyr Ser Thr Gly Gln Val Ser Val Glu Ile Glu Trp Glu Leu Gln
            675             680             685

Lys Glu Asn Ser Lys Arg Trp Asn Pro Glu Ile Gln Tyr Thr Ser Asn
        690             695             700

Tyr Tyr Lys Ser Asn Asn Val Glu Phe Ala Val Asn Thr Glu Gly Val
705             710             715             720
```

-continued

```
Tyr Ser Glu Pro Arg Pro Ile Gly Thr Arg Tyr Leu Thr Arg Asn Leu
                725             730             735

<210> SEQ ID NO 141
<211> LENGTH: 748
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (594)..(600)
<223> OTHER INFORMATION: X is any amino acid

<400> SEQUENCE: 141

Met Ala Ala Asp Gly Tyr Leu Pro Asp Trp Leu Glu Asp Asn Leu Ser
1               5               10              15

Glu Gly Ile Arg Glu Trp Trp Asp Leu Lys Pro Gly Ala Pro Lys Pro
            20              25              30

Lys Ala Asn Gln Gln Lys Gln Asp Asp Gly Arg Gly Leu Val Leu Pro
        35              40              45

Gly Tyr Lys Tyr Leu Gly Pro Phe Asn Gly Leu Asp Lys Gly Glu Pro
    50              55              60

Val Asn Ala Ala Asp Ala Ala Ala Leu Glu His Asp Lys Ala Tyr Asp
65              70              75              80

Gln Gln Leu Lys Ala Gly Asp Asn Pro Tyr Leu Arg Tyr Asn His Ala
            85              90              95

Asp Ala Glu Phe Gln Glu Arg Leu Gln Glu Asp Thr Ser Phe Gly Gly
            100             105             110

Asn Leu Gly Arg Ala Val Phe Gln Ala Lys Lys Arg Val Leu Glu Pro
        115             120             125

Leu Gly Leu Val Glu Glu Gly Ala Lys Thr Ala Pro Gly Lys Lys Arg
    130             135             140

Pro Val Glu Gln Ser Pro Gln Glu Pro Asp Ser Ser Ser Gly Ile Gly
145             150             155             160

Lys Thr Gly Gln Gln Pro Ala Lys Lys Arg Leu Asn Phe Gly Gln Thr
            165             170             175

Gly Asp Ser Glu Ser Val Pro Asp Pro Gln Pro Leu Gly Glu Pro Pro
            180             185             190

Ala Thr Pro Ala Ala Val Gly Pro Thr Thr Met Ala Ser Gly Gly Gly
        195             200             205

Ala Pro Met Ala Asp Asn Asn Glu Gly Ala Asp Gly Val Gly Asn Ala
    210             215             220

Ser Gly Asn Trp His Cys Asp Ser Thr Trp Leu Gly Asp Arg Val Ile
225             230             235             240

Thr Thr Ser Thr Arg Thr Trp Ala Leu Pro Thr Tyr Asn Asn His Leu
            245             250             255

Tyr Lys Gln Ile Ser Ser Ala Ser Thr Gly Ala Ser Asn Asp Asn His
            260             265             270

Tyr Phe Gly Tyr Ser Thr Pro Trp Gly Tyr Phe Asp Phe Asn Arg Phe
    275             280             285

His Cys His Phe Ser Pro Arg Asp Trp Gln Arg Leu Ile Asn Asn Asn
    290             295             300

Trp Gly Phe Arg Pro Lys Arg Leu Asn Phe Lys Leu Phe Asn Ile Gln
305             310             315             320

Val Lys Glu Val Thr Thr Asn Asp Gly Val Thr Thr Ile Ala Asn Asn
            325             330             335
```

```
Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Ser Ser
                580                 585                 590

Ala Xaa Xaa Xaa Xaa Xaa Xaa Xaa Ala Ser Pro Ala Thr Gly Asp Val
            595                 600                 605

His Ala Met Gly Ala Leu Pro Gly Met Val Trp Gln Asp Arg Asp Val
    610                 615                 620

Tyr Leu Gln Gly Pro Ile Trp Ala Lys Ile Pro His Thr Asp Gly His
625                 630                 635                 640

Phe His Pro Ser Pro Leu Met Gly Gly Phe Gly Leu Lys Asn Pro Pro
                645                 650                 655

Pro Gln Ile Leu Ile Lys Asn Thr Pro Val Pro Ala Asn Pro Pro Ala
                660                 665                 670

Glu Phe Ser Ala Thr Lys Phe Ala Ser Phe Ile Thr Gln Tyr Ser Thr
            675                 680                 685

Gly Gln Val Ser Val Glu Ile Glu Trp Glu Leu Gln Lys Glu Asn Ser
    690                 695                 700

Lys Arg Trp Asn Pro Glu Val Gln Tyr Thr Ser Asn Tyr Ala Lys Ser
705                 710                 715                 720

Ala Asn Val Asp Phe Thr Val Asp Asn Asn Gly Leu Tyr Thr Glu Pro
                725                 730                 735

Arg Pro Ile Gly Thr Arg Tyr Leu Thr Arg Pro Leu
            740                 745
```

-continued

<210> SEQ ID NO 142
<211> LENGTH: 747
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (591)..(597)
<223> OTHER INFORMATION: X is any amino acid

<400> SEQUENCE: 142

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
                20                  25                  30

Lys Pro Ala Glu Arg His Lys Asp Asp Ser Arg Gly Leu Val Leu Pro
                35                  40                  45

Gly Tyr Lys Tyr Leu Gly Pro Phe Asn Gly Leu Asp Lys Gly Glu Pro
            50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
            130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

-continued

```
Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Ala Ala Ala Xaa Xaa
            580                 585                 590

Xaa Xaa Xaa Xaa Xaa Ala Ala Arg Gln Ala Ala Thr Ala Asp Val Asn
        595                 600                 605

Thr Gln Gly Val Leu Pro Gly Met Val Trp Gln Asp Arg Asp Val Tyr
    610                 615                 620

Leu Gln Gly Pro Ile Trp Ala Lys Ile Pro His Thr Asp Gly His Phe
625                 630                 635                 640

His Pro Ser Pro Leu Met Gly Gly Phe Gly Leu Lys His Pro Pro Pro
            645                 650                 655

Gln Ile Leu Ile Lys Asn Thr Pro Val Pro Ala Asn Pro Ser Thr Thr
            660                 665                 670

Phe Ser Ala Ala Lys Phe Ala Ser Phe Ile Thr Gln Tyr Ser Thr Gly
        675                 680                 685

Gln Val Ser Val Glu Ile Glu Trp Glu Leu Gln Lys Glu Asn Ser Lys
    690                 695                 700

Arg Trp Asn Pro Glu Ile Gln Tyr Thr Ser Asn Tyr Asn Lys Ser Val
705                 710                 715                 720

Asn Val Asp Phe Thr Val Asp Thr Asn Gly Val Tyr Ser Glu Pro Arg
            725                 730                 735

Pro Ile Gly Thr Arg Tyr Leu Thr Arg Asn Leu
            740                 745
```

```
<210> SEQ ID NO 143
<211> LENGTH: 748
```

-continued

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (592)..(598)
<223> OTHER INFORMATION: X is any amino acid

<400> SEQUENCE: 143

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
    355                 360                 365
```

```
Ala Asp Val Phe Met Ile Pro Gln Tyr Gly Tyr Leu Thr Leu Asn Asp
    370             375             380

Gly Ser Gln Ala Val Gly Arg Ser Ser Phe Tyr Cys Leu Glu Tyr Phe
385             390             395             400

Pro Ser Gln Met Leu Arg Thr Gly Asn Asn Phe Gln Phe Ser Tyr Glu
            405             410             415

Phe Glu Asn Val Pro Phe His Ser Ser Tyr Ala His Ser Gln Ser Leu
            420             425             430

Asp Arg Leu Met Asn Pro Leu Ile Asp Gln Tyr Leu Tyr Tyr Leu Ser
        435             440             445

Lys Thr Ile Asn Gly Ser Gly Gln Asn Gln Gln Thr Leu Lys Phe Ser
    450             455             460

Val Ala Gly Pro Ser Asn Met Ala Val Gln Gly Arg Asn Tyr Ile Pro
465             470             475             480

Gly Pro Ser Tyr Arg Gln Gln Arg Val Ser Thr Thr Val Thr Gln Asn
            485             490             495

Asn Asn Ser Glu Phe Ala Trp Pro Gly Ala Ser Ser Trp Ala Leu Asn
            500             505             510

Gly Arg Asn Ser Leu Met Asn Pro Gly Pro Ala Met Ala Ser His Lys
        515             520             525

Glu Gly Glu Asp Arg Phe Phe Pro Leu Ser Gly Ser Leu Ile Phe Gly
    530             535             540

Lys Gln Gly Thr Gly Arg Asp Asn Val Asp Ala Asp Lys Val Met Ile
545             550             555             560

Thr Asn Glu Glu Glu Ile Lys Thr Thr Asn Pro Val Ala Thr Glu Ser
            565             570             575

Tyr Gly Gln Val Ala Thr Asn His Gln Ser Ala Gln Ala Ala Ala Xaa
            580             585             590

Xaa Xaa Xaa Xaa Xaa Xaa Ala Ser Ala Gln Ala Gln Thr Gly Trp Val
        595             600             605

Gln Asn Gln Gly Ile Leu Pro Gly Met Val Trp Gln Asp Arg Asp Val
    610             615             620

Tyr Leu Gln Gly Pro Ile Trp Ala Lys Ile Pro His Thr Asp Gly Asn
625             630             635             640

Phe His Pro Ser Pro Leu Met Gly Gly Phe Gly Met Lys His Pro Pro
            645             650             655

Pro Gln Ile Leu Ile Lys Asn Thr Pro Val Pro Ala Asp Pro Pro Thr
            660             665             670

Ala Phe Asn Lys Asp Lys Leu Asn Ser Phe Ile Thr Gln Tyr Ser Thr
        675             680             685

Gly Gln Val Ser Val Glu Ile Glu Trp Glu Leu Gln Lys Glu Asn Ser
    690             695             700

Lys Arg Trp Asn Pro Glu Ile Gln Tyr Thr Ser Asn Tyr Tyr Lys Ser
705             710             715             720

Asn Asn Val Glu Phe Ala Val Asn Thr Glu Gly Val Tyr Ser Glu Pro
            725             730             735

Arg Pro Ile Gly Thr Arg Tyr Leu Thr Arg Asn Leu
            740             745
```

```
<210> SEQ ID NO 144
<211> LENGTH: 7
<212> TYPE: PRT
<213> ORGANISM: Artificial Sequence
<220> FEATURE:
```

-continued

<223> OTHER INFORMATION: Synthetic polypeptide

<400> SEQUENCE: 144

Arg Pro Gly Arg Glu Ala Ser
1               5

ADENO-ASSOCIATED VIRAL VECTOR VARIANTS

REFERENCE TO RELATED APPLICATIONS

This application is a national phase application under 35 U.S.C. § 371 of International Application No. PCT/US2020/061464, filed Nov. 20, 2020, which claims benefit of priority to U.S. Provisional Application Ser. No. 62/939,315, filed Nov. 22, 2019, and 63/084,709, filed Sep. 29, 2020, the entire contents of each of which are being hereby incorporated by reference in their entirety.

REFERENCE TO A SEQUENCE LISTING

The instant application contains a Sequence Listing, which has been submitted in ASCII format via EFS-Web and is hereby incorporated by reference in its entirety. Said ASCII copy, created on May 20, 2022, is named CHOPP0038US_ST25.txt and is 63,782 bytes in size.

BACKGROUND

1. Field

The present invention relates generally to the fields of medicine, virology, and neurology. More particularly, it concerns targeting peptides that target delivery of viral vectors to distinct structures in the brain.

2. Description of Related Art

Different strategies have been developed to generate AAV vector variants including rational design and directed evolution. The rational design approach utilizes knowledge of AAV capsids to make targeted changes to the capsid to alter transduction efficiency or specificity, such as tyrosine mutations on the capsid surface for increasing transduction efficiency. The directed evolution approach does not require any knowledge of capsid structure and is done through random mutagenesis, capsid shuffling, or random peptide insertions. These strategies generally use in vitro systems or mice, which are ideal for cell-based or mouse studies, but do not imply translation to the clinic. In fact, no AAV variants target distinct brain structures specifically or efficiently. As such, AAV variants that are able to target distinct primate brain structures are needed.

SUMMARY

Provided herein are viral vectors each comprising a modified capsid, wherein the modified capsid comprises at least one amino acid sequence that targets the viral vector to a distinct brain structure.

In one embodiment, provided are modified adeno-associated virus (AAV) capsid proteins comprising a targeting peptide that targets a viral vector comprising the modified AAV capsid protein to a distinct organ or brain structure, and the targeting peptide is three to ten amino acids in length. In some aspects, the modified AAV capsid proteins are modified AAV1 capsid proteins, modified AAV2 capsid proteins, or modified AAV9 capsid proteins.

In some aspects, the modified AAV capsid proteins are derived from an AAV1 capsid protein (see SEQ ID NO: 138), and the targeting peptide is inserted after residue 590 of the AAV1 capsid protein. In some aspects, the targeting peptide is flanked by linker sequences, and the linker sequences on each side of the targeting peptides are two or three amino acids long. In some aspects, the linker sequences are SSA on the N-terminal side of the targeting peptide and AS on the C-terminal side of the targeting peptide. In some aspects, the modified AAV1 capsid proteins have a sequence at least 95% identical to SEQ ID NO: 141.

In some aspects, the modified AAV capsid proteins are derived from an AAV2 capsid protein (see SEQ ID NO: 139), and the targeting peptide is inserted after residue 587 of the AAV2 capsid protein. In some aspects, the targeting peptide is flanked by linker sequences, and the linker sequences on each side of the targeting peptides are two or three amino acids long. In some aspects, the linker sequences are AAA on the N-terminal side of the targeting peptide and AA on the C-terminal side of the targeting peptide. In some aspects, the modified AAV2 capsid proteins have a sequence at least 95% identical to SEQ ID NO: 142.

In some aspects, the modified AAV capsid proteins are derived from an AAV9 capsid protein (see SEQ ID NO: 140), and the targeting peptide is inserted after residue 588 of the AAV9 capsid protein. In some aspects, the targeting peptide is flanked by linker sequences, and the linker sequences on each side of the targeting peptides are two or three amino acids long. In some aspects, the linker sequences are AAA on the N-terminal side of the targeting peptide and AS on the C-terminal side of the targeting peptide. In some aspects, the modified AAV9 capsid proteins have a sequence at least 95% identical to SEQ ID NO: 143.

In some aspects, the target peptide comprises a sequence up to ten amino acids in length having therein an amino acid sequence selected from the group consisting of SEQ ID NOs: 1-137 and 144. In some aspects, the targeting peptide is seven amino acids in length.

In some aspects, the distinct brain structure is the brainstem, caudate, cerebellar cortex, cerebral cortex, ependyma, globus pallidus, hippocampus, meninges, optic nerve, putamen, spinal cord, substantia nigra, subthalamic nuclei, or thalamus. In certain aspects, the modified AAV capsid protein is a modified AAV1 capsid protein, and the targeting peptide is selected from those listed in Table 1 in order to target a corresponding brain structure. In certain aspects, the modified AAV capsid protein is a modified AAV2 capsid protein, and the targeting peptide is selected from those listed in Table 2 in order to target a corresponding brain structure. In certain aspects, the modified AAV capsid protein is a modified AAV9 capsid protein, and the targeting peptide is selected from those listed in Table 3 in order to target a corresponding brain structure.

In some aspects, the distinct organ is the brain, kidney, heart, liver, gonad, spleen, or liver. In certain aspects, the modified AAV capsid protein is a modified AAV1 capsid protein, and the targeting peptide is selected from those listed in Table 4 in order to target a corresponding organ. In certain aspects, the modified AAV capsid protein is a modified AAV2 capsid protein, and the targeting peptide is selected from those listed in Table 5 in order to target a corresponding organ. In certain aspects, the modified AAV capsid protein is a modified AAV9 capsid protein, and the targeting peptide is selected from those listed in Table 6 in order to target a corresponding organ.

In one embodiment, provided herein are nucleic acids comprising a sequence encoding the modified capsid protein of any one of the present embodiments.

In one embodiment, provided herein are recombinant adeno-associated viruses (rAAV) comprising the modified capsid protein of any one of the present embodiments. In some aspects, combinations of rAAVs are provided. For example, the combination of an rAAV having a modified AAV1 capsid protein and a targeting peptide of SEQ ID NO: 21, an rAAV having a modified AAV2 capsid protein and a targeting peptide of SEQ ID NO: 53, an rAAV having a modified AAV2 capsid protein and a targeting peptide of SEQ ID NO: 80, and an rAAV having a modified AAV9 capsid protein and a targeting peptide of SEQ ID NO: 113 is provided.

In one embodiment, provided herein are viral vectors comprising a nucleic acid encoding the modified capsid protein of any one of the present embodiments. In some aspects, the viral vectors further comprise a nucleic acid sequence encoding a nucleic acid of interest. In some aspects, the nucleic acid of interest is a therapeutic agent. In some aspects, the therapeutic agent is an enzyme or an RNAi molecule.

In one embodiment, provided herein are cells comprising the viral vector of any one of the present embodiments. In some aspects, the cell is a mammalian cell, such as a human cell. In some aspects, the cell is in vitro or in vivo.

In one embodiment, provided herein are pharmaceutical compositions comprising the viral vector of the present embodiments and a pharmaceutically acceptable carrier.

In one embodiment, provided herein are methods to deliver an agent to a distinct brain structure of a subject, comprising administering a virus of the present embodiments to the subject. In some aspects, the distinct brain structure is the brainstem, caudate, cerebellar cortex, cerebral cortex, ependyma, globus pallidus, hippocampus, meninges, optic nerve, putamen, spinal cord, substantia nigra, subthalamic nuclei, or thalamus. In certain aspects, an rAAV having a modified AAV1 capsid protein is used, and the targeting peptide is selected from those listed in Table 1 in order to target a corresponding brain structure. In certain aspects, an rAAV having a modified AAV2 capsid protein is used, and the targeting peptide is selected from those listed in Table 2 in order to target a corresponding brain structure. In certain aspects, an rAAV having a modified AAV9 capsid protein is used, and the targeting peptide is selected from those listed in Table 3 in order to target a corresponding brain structure. In various aspects, combinations of any of the rAAVs are used. For example, the combination of an rAAV having a modified AAV1 capsid protein and a targeting peptide of SEQ ID NO: 21, an rAAV having a modified AAV2 capsid protein and a targeting peptide of SEQ ID NO: 53, an rAAV having a modified AAV2 capsid protein and a targeting peptide of SEQ ID NO: 80, and an rAAV having a modified AAV9 capsid protein and a targeting peptide of SEQ ID NO: 113 is used.

In one embodiment, provided herein are methods to deliver an agent to a distinct organ of a subject, comprising administering a virus of the present embodiments to the subject. In some aspects, the organ is the brain, kidney, heart, liver, gonad, spleen, or liver. In certain aspects, an rAAV having a modified AAV1 capsid protein is used, and the targeting peptide is selected from those listed in Table 4 in order to target a corresponding organ. In certain aspects, an rAAV having a modified AAV2 capsid protein is used, and the targeting peptide is selected from those listed in Table 5 in order to target a corresponding organ. In certain aspects, an rAAV having a modified AAV9 capsid protein is used, and the targeting peptide is selected from those listed in Table 6 in order to target a corresponding organ. In various aspects, combinations of any of the rAAVs are used.

In some aspects, the agent is an siRNA, shRNA, miRNA, non-coding RNA, lncRNA, therapeutic protein, or CRISPR system. In some aspects, the administration is to the central nervous system. In some aspects, the administration is to a cisterna magna, an intraventricular space, an ependyma, a brain ventricle, a subarachnoid space, and/or an intrathecal space. In some aspects, the brain ventricle is the rostral lateral ventricle, and/or the caudal lateral ventricle, and/or the right lateral ventricle, and/or the left lateral ventricle, and/or the right rostral lateral ventricle, and/or the left rostral lateral ventricle, and/or the right caudal lateral ventricle, and/or the left caudal lateral ventricle.

In some aspects, a plurality of viral particles is administered. In some aspects, the virus is administered at a dose of about $1 \times 10^6$ to about $1 \times 10^{18}$ vector genomes per kilogram (vg/kg). In some aspects, the virus is administered at a dose from about $1 \times 10^7 - 1 \times 10^{17}$, about $1 \times 10^8 - 1 \times 10^{16}$, about $1 \times 10^9 - 1 \times 10^{15}$, about $1 \times 10^{10} - 1 \times 10^{14}$, about $1 \times 10^{10} - 1 \times 10^{13}$, about $1 \times 10^{10} - 1 \times 10^{13}$, about $1 \times 10^{10} - 1 \times 10^{11}$, about $1 \times 10^{11} - 1 \times 10^{12}$, about $1 \times 10^{12} - \times 10^{13}$, or about $1 \times 10^{13} - 1 \times 10^{14}$ vg/kg of the patient. In some aspects, the subject is human.

In one embodiment, provided herein are methods of treating a disease in a mammal comprising administering the virus of the present embodiments to the mammal. In some aspects, the disease is a neurodegenerative disease. In some aspects, the neurodegenerative disease is Huntington's disease, ALS, hereditary spastic hemiplegia, primary lateral sclerosis, spinal muscular atrophy, Kennedy's disease, Alzheimer's disease, a polyglutamine repeat disease, or Parkinson's disease. In some aspects, the mammal is human.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. AAV peptide display library schematic.

FIG. 4. Graphical representation of round-over-round barcode enrichment. The total number of unique barcodes recovered after Round 1 and Round 2 enrichment in Rhesus macaque for each tissue collected. Round 2 values for DNA and RNA are shown.

In FIG. 7A, RPGREAS is SEQ ID NO: 144, RDATRSS is SEQ ID NO: 12, NSVRPLT is SEQ ID NO: 23, TAPKSLK is SEQ ID NO: 25, RGVLVTT is SEQ ID NO: 2, DKTRAGS is SEQ ID NO: 5, RDSTROL is SEQ ID NO: 26, PIPAGKK is SEQ ID NO: 9, SGVLVOR is SEQ ID NO: 32, NSVHNTA is SEQ ID NO: 18, TATPRKG is SEQ ID NO: 49, VSLKERV is SEQ ID NO: 29, DETSRLV is SEQ ID NO: 30, SVASAKK is SEQ ID NO: 48, NDVRAKG is SEQ ID NO: 40, SGTFVKA is SEQ ID NO: 33, DRLKGIV is SEQ ID NO: 31, KAAGRTV is SEQ ID NO: 46, ERDRTRG is SEQ ID NO: 21, NSVKSVL is SEQ ID NO: 27, VKALGRP is SEQ ID NO: 39, AKLNKSS is SEQ ID NO: 17, KGLRTPT is SEQ ID NO: 51, HVIRLPS is SEQ ID NO: 47, and TNRMALS is SEQ ID NO: 43. In FIG. 7B, HDGGASR is SEQ ID NO: 103, GSRAGVG is SEQ ID NO: 105, ESTGRER is SEQ ID NO: 73, KAQGVGG is SEQ ID NO: 79, RGSTQVG is SEQ ID NO: 94, EAQSHPR is SEQ ID NO: 91, RDDVPLR is SEQ ID NO: 56, GRSTGMT is SEQ ID NO: 95, VPGRTAG is SEQ ID NO: 81, ARGSGVN is SEQ ID NO: 82, GRGGAAL is SEQ ID NO: 100, TKSLSSG is SEQ ID NO: 92, RAVPAGG is SEQ ID NO: 84, NARPVSA is SEQ ID NO: 76, DDPSARR is SEQ ID NO: 53, TSNRGOV is SEQ ID NO: 63, VOGROGG is SEQ ID NO: 60, SSSKTGS is SEQ ID NO: 58, KASGAGG is SEQ ID NO: 88, VTOSKGA is SEQ ID NO: 74, STPAPKS is SEQ ID NO: 86, RSNAPOT is SEQ ID NO: 90, LTSRTSP is SEQ ID NO: 52, RGSGSAV is SEQ ID NO: 75, and KLSISGN is SEQ ID NO: 106. In FIG. 7C, MMGRPGR is SEQ ID NO: 136, KGGGFHG is SEQ ID NO: 110, RGDLOWV is SEQ ID NO: 113, MDLTKAV is SEQ ID NO: 135, RGGGVYG is SEQ ID NO: 126, RAKPGME is SEQ ID NO: 111, GGRPGSW is SEQ ID NO: 123, RSDVGSL is SEQ ID NO: 120, KGGGVHG is SEQ ID NO: 117, RGDLRFI is SEQ ID NO: 125, AGVKPGR is SEQ ID NO: 121, GRDVTRS is SEQ ID NO: 112, AWDGTRV is SEQ ID NO: 131, GGDRTRG is SEQ ID NO: 114, ARGDGWR is SEQ ID NO: 132, RRGDAWS is SEQ ID NO: 134, GADRTRG is SEQ ID NO: 127, RDTTRNL is SEQ ID NO: 116, RGDLASV is SEQ ID NO: 115, GRDYTRL is SEQ ID NO: 133, RRDETRT is SEQ ID NO: 129, RGDMYRV is SEQ ID NO: 118, RGDEMGL is SEQ ID NO: 128, RGDWPRG is SEQ ID NO: 122, and RGDYPRS is SEQ ID NO: 124.

FIGS. 9A-D. AAV9 1999 in vivo mouse validation. An eGFP expression construct was packaged into AAV9 1999 driven by the CAG promoter. AAV9 1999 and AAV9 capsids containing the eGFP construct were delivered to C57BL/6 p0 mouse pups by ICV injection at 1 E10 vg. Representative images of eGFP fluorescence signal is the whole brain (FIG. 9A), whole brain sagittal section (FIG. 9B), S1 cortex sections (FIG. 9C, left), hippocampus sections (FIG. 9C, middle), cerebellum sagittal section (FIG. 9C, right), and lumbar spinal cord coronal section (FIG. 9D).

DETAILED DESCRIPTION

Figure 2:
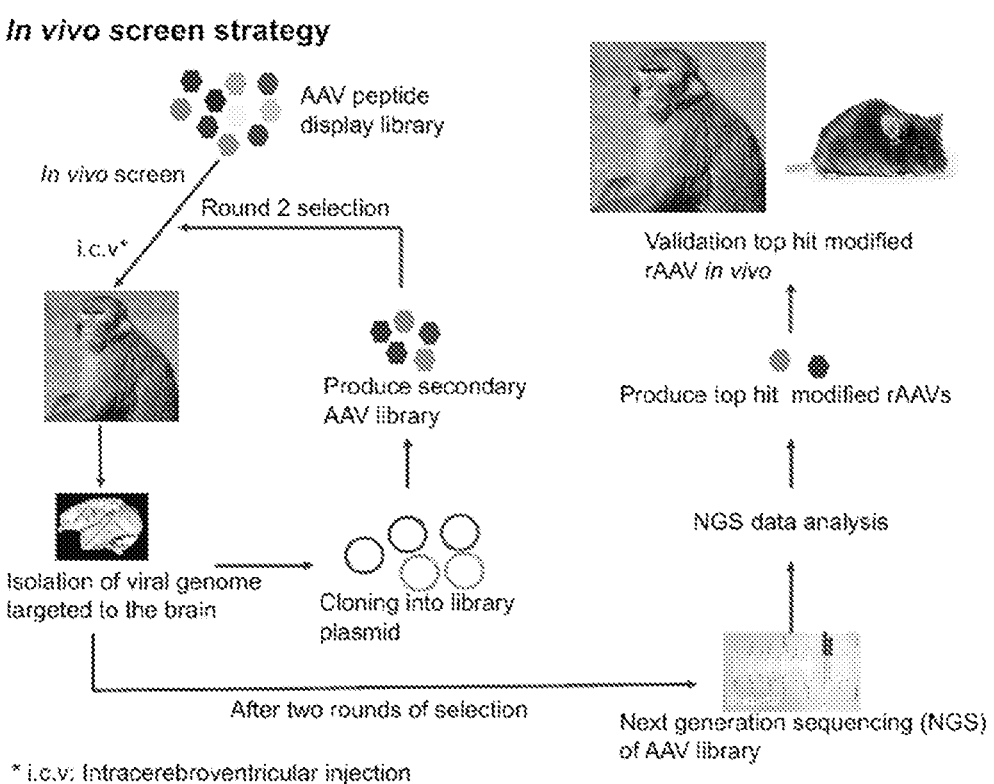
FIG. 2 In vivo screen strategy schematic.

Provided herein are viral vectors each comprising a modified capsid, wherein the modified capsid comprises at least one amino acid sequence that targets the viral vector to a distinct brain structure. In certain embodiments, the brain structure is the brainstem, caudate, cerebellar cortex, cerebral cortex, ependyma, globus pallidus, hippocampus, meninges, optic nerve, putamen, spinal cord, substantia nigra, subthalamic nuclei, or thalamus. The targeting peptides for each brain structure are provided in Tables 1-3.

In certain embodiments, the viral vector is an adeno associated viral vector (AAV). In certain embodiments, the AAV is AAV1, AAV2, or AAV9. An exemplary wildtype reference AAV1 capsid protein sequence is provided in SEQ ID NO: 138. An exemplary wildtype reference AAV2 capsid protein sequence is provided in SEQ ID NO: 139. An exemplary wildtype reference AAV9 capsid protein sequence is provided in SEQ ID NO: 140. In certain aspects, the targeting peptide is inserted at position 590 of the AAV1 capsid, position 587 of the AAV2 capsid, or position 588 of the AAV9 capsid. An exemplary modified AAV1 capsid protein sequence is provided in SEQ ID NO: 141, which shows the targeting peptide insertion after position 590 as $SSAX_7AS$, where the leading SSA and the trailing AS are linker sequences and $X_7$ represents the targeting peptide. An exemplary modified AAV2 capsid protein sequence is provided in SEQ ID NO: 142, which shows the targeting peptide insertion after position 587 as $AAAX_7AA$, where the leading AAA and the trailing AA are linker sequences and $X_7$ represents the targeting peptide. An exemplary modified AAV9 capsid protein sequence is provided in SEQ ID NO: 143, which shows the targeting peptide insertion after position 588 as $AAAX_7AS$, where the leading AAA and the trailing AS are linker sequences and $X_7$ represents the targeting peptide.

7

TABLE 1

AAV1 targeting peptides for each brain structure.

| Region | Peptide | SEQ ID NO |
|---|---|---|
| Brainstem | RPGREQA | 1 |
| | RGVLVTT | 2 |
| | RPGRESA | 3 |
| | NESLKKK | 4 |
| | DKTRAGS | 5 |
| | TAKSKQA | 6 |
| | PVKKKDA | 7 |
| | GRETLKG | 8 |
| | PIPAGKK | 9 |
| Caudate | RPGRESA | 3 |
| | PVKKKDA | 7 |
| | RPGREQA | 1 |
| | NVVRAGT | 10 |
| | KATANTR | 11 |
| | RDATRSS | 12 |
| | VPTKSPK | 13 |
| | AGVARSK | 14 |
| | RSRSEVL | 15 |
| | EVKGKGK | 16 |
| | RPGREAS | 144 |
| | RDSTRQL | 26 |
| | SGVLVQR | 32 |
| | DKTRAGS | 5 |
| | TAPKSLK | 25 |
| Cerebellar Cortex | AKLNKSS | 17 |
| | NESLKKK | 4 |
| | NSVHNTA | 18 |
| | NVVRGGA | 19 |
| | NRLVAGG | 20 |
| | RPGRESA | 3 |
| | ERDRTRG | 21 |
| | PIPAGKK | 9 |
| | RPGREQA | 1 |
| Cerebellar Cortex; Vermis | RPGREAS | 144 |
| | DKTRAGS | 5 |
| | NSVRPLT | 23 |
| | RDSTRQL | 26 |
| | RDATRSS | 12 |
| Cerebellum; right upper vermis | NSVRPLT | 23 |
| | RDATRSS | 12 |
| | DKTRAGS | 5 |
| | TAPKSLK | 25 |
| | RPGREAS | 144 |
| Cerebellum; lateral to brainstem (right) | NSVRPLT | 23 |
| | TAPKSLK | 25 |
| | RDSTRQL | 26 |
| | RPGREAS | 144 |
| | PIPAGKK | 9 |
| | RDATRSS | 12 |
| Cerebellum; Left hemisphere adjacent to upper vermis | RPGREAS | 144 |
| | DKTRAGS | 5 |
| | RDATRSS | 12 |
| | RDSTRQL | 26 |
| | TAPKSLK | 25 |
| Cerebellum; Left hemisphere, Most lateral point | RPGREAS | 144 |
| | RDSTRQL | 26 |
| | DKTRAGS | 5 |
| | TAPKSLK | 25 |
| | NSVRPLT | 23 |
| | RDATRSS | 12 |
| Cerebellum; Left hemisphere, Adjacent to brain stem | NSVRPLT | 23 |
| | RPGREAS | 144 |
| | RDATRSS | 12 |
| | DKTRAGS | 5 |
| | NSVHNTA | 18 |
| | TAPKSLK | 25 |

8

TABLE 1-continued

AAV1 targeting peptides for each brain structure.

| Region | Peptide | SEQ ID NO |
|---|---|---|
| Cerebral Cortex | VQGSKMK | 22 |
| | RDATRSS | 12 |
| | NSVRPLT | 23 |
| | RPGRESA | 3 |
| | NKIHANP | 24 |
| | ERDRTRG | 21 |
| | DKTRAGS | 5 |
| | TAPKSLK | 25 |
| | RDSTRQL | 26 |
| | RPGREQA | 1 |
| Cochlea (ear) | RDATRSS | 12 |
| | RPGREAS | 144 |
| | TAPKSLK | 25 |
| | DKTRAGS | 5 |
| | NSVRPLT | 23 |
| | TATPRKG | 49 |
| Deep Cerebellar Nuclei | RPGREAS | 144 |
| | TAPKSLK | 25 |
| | RDATRSS | 12 |
| | RDSTRQL | 26 |
| | DKTRAGS | 5 |
| Dorsal Root Ganglia, Lumbar | RPGREAS | 144 |
| | RDATRSS | 12 |
| | NSVRPLT | 23 |
| | DKTRAGS | 5 |
| | TAPKSLK | 25 |
| Dorsal Root Ganglia, Cervical | RPGREAS | 144 |
| | DKTRAGS | 5 |
| | TAPKSLK | 25 |
| | RDATRSS | 12 |
| | NSVHNTA | 18 |
| | NSVRPLT | 23 |
| Dorsal Root Ganglia, Thoracic | RDATRSS | 12 |
| | RPGREAS | 144 |
| | DKTRAGS | 5 |
| | TAPKSLK | 25 |
| | RDSTRQL | 26 |
| Ependyma | ERDRTRG | 21 |
| | RGVLVTT | 2 |
| | RPGRESA | 3 |
| | PIPAGKK | 9 |
| | NESLKKK | 4 |
| | NSVKSVL | 27 |
| | PVKKKDA | 7 |
| | VQGSKMK | 22 |
| | NVTIKSK | 28 |
| Ependyma; 3rd Ventrical | DKTRAGS | 5 |
| | TAPKSLK | 25 |
| | RPGREAS | 144 |
| | RDATRSS | 12 |
| | DRLKGIV | 31 |
| Ependyma; 4th Ventrical | TAPKSLK | 25 |
| | NSVRPLT | 23 |
| | RPGREAS | 144 |
| | KAAGRTV | 46 |
| | RDATRSS | 12 |
| | DKTRAGS | 5 |
| Ependyma; Lt Ventrical | RPGREAS | 144 |
| | NSVRPLT | 23 |
| | RDATRSS | 12 |
| | TAPKSLK | 25 |
| | DETSRLV | 30 |
| | DKTRAGS | 5 |
| Globus Pallidus | RPGRESA | 3 |
| | ERDRTRG | 21 |

9
10

TABLE 1-continued

TABLE 1-continued

AAV1 targeting peptides for each brain structure.

AAV1 targeting peptides for each brain structure.

| Region | Peptide | SEQ ID NO |
|---|---|---|
| | VSLKERV | 29 |
| | VQGSKMK | 22 |
| | DKTRAGS | 5 |
| | DETSRLV | 30 |
| | RDATRSS | 12 |
| | AGVARSK | 14 |
| | EVKGKGK | 16 |
| | DRLKGIV | 31 |
| Globus Pallidus External | RGVLVTT | 2 |
| | SGTFVKA | 33 |
| | EVKGKGK | 16 |
| | SVASAKK | 48 |
| | VSLKERV | 29 |
| | TATPRKG | 49 |
| Globus Pallidus Internal | RGVLVTT | 2 |
| | TAPKSLK | 25 |
| | TKTGLKL | 50 |
| | ERDRTRG | 21 |
| | SGVLVQR | 32 |
| | TATPRKG | 49 |
| | RPGREAS | 144 |
| Hippocampus | RGVLVTT | 2 |
| | RPGRESA | 3 |
| | SGVLVQR | 32 |
| | PVKKKDA | 7 |
| | NESLKKK | 4 |
| | SGTFVKA | 33 |
| | RPGREQA | 1 |
| | NSIARPV | 34 |
| Hippocampus; CA1 | RGVLVTT | 2 |
| | SGVLVQR | 32 |
| | SVASAKK | 48 |
| | RDATRSS | 12 |
| | DKTRAGS | 5 |
| | TAPKSLK | 25 |
| Hippocampus; CA3 | RPGREAS | 144 |
| | DETSRLV | 30 |
| | RDATRSS | 12 |
| | DKTRAGS | 5 |
| | ERDRTRG | 21 |
| | RDSTRQL | 26 |
| Hippocampus; DG | NSVRPLT | 23 |
| | RDATRSS | 12 |
| | TAPKSLK | 25 |
| | RDSTRQL | 26 |
| | RPGREAS | 144 |
| Inferior Olive | RPGREAS | 144 |
| | DKTRAGS | 5 |
| | TAPKSLK | 25 |
| | NDVRAKG | 40 |
| | RDATRSS | 12 |
| | NSVRPLT | 23 |
| Lateral Geniculate Nuclei | NSVRPLT | 23 |
| | TAPKSLK | 25 |
| | RPGREAS | 144 |
| | DKTRAGS | 5 |
| | RDATRSS | 12 |
| Meninges | RPGRESA | 3 |
| | ERDRTRG | 21 |
| | RDATRSS | 12 |
| | DKTRAGS | 5 |
| | PIPAGKK | 9 |
| | NRARAGE | 35 |
| | ARHALGG | 36 |
| | HSSRPVA | 37 |
| | PVKKKDA | 7 |
| | RPGREAS | 144 |

| Region | Peptide | SEQ ID NO |
|---|---|---|
| | TAPKSLK | 25 |
| | NSVRPLT | 23 |
| Motor Cortex | RPGREAS | 144 |
| | RGVLVTT | 2 |
| | NSVRPLT | 23 |
| | TAPKSLK | 25 |
| | DKTRAGS | 5 |
| | RDATRSS | 12 |
| Optic Nerve | AGVARSK | 14 |
| | RSRSEVL | 15 |
| | EVKGKGK | 16 |
| | DRLKGIV | 31 |
| | KTGTARL | 38 |
| | RPGRESA | 3 |
| | PVKKKDA | 7 |
| | RGVLVTT | 2 |
| | ERDRTRG | 21 |
| | RPGREAS | 144 |
| | NSVRPLT | 23 |
| | TAPKSLK | 25 |
| | DKTRAGS | 5 |
| | NDVRAKG | 40 |
| | RDATRSS | 12 |
| Prefrontal Cortex | RPGREAS | 144 |
| | NSVRPLT | 23 |
| | TAPKSLK | 25 |
| | DKTRAGS | 5 |
| | RDATRSS | 12 |
| Pons | RPGREAS | 144 |
| | NSVRPLT | 23 |
| | TAPKSLK | 25 |
| | RDATRSS | 12 |
| | DKTRAGS | 5 |
| Putamen | DETSRLV | 30 |
| | VKALGRP | 39 |
| | NDVRAKG | 40 |
| | NESLKKK | 4 |
| | ERDRTRG | 21 |
| | RPGREAS | 144 |
| | QGVLVVR | 41 |
| | KQYAGSQ | 42 |
| | RDATRSS | 12 |
| | VPTKSPK | 13 |
| | DKTRAGS | 5 |
| | KAAGRTV | 46 |
| | TAPKSLK | 25 |
| Reticular Formation | RPGREAS | 144 |
| | RDSTRQL | 26 |
| | KGLRTPT | 51 |
| | RDATRSS | 12 |
| | NSVRPLT | 23 |
| | DKTRAGS | 5 |
| Spinal Cord | PVKKKDA | 7 |
| | RGVLVTT | 2 |
| | PIPAGKK | 9 |
| | SGVLVQR | 32 |
| | NESLKKK | 4 |
| | RPGRESA | 3 |
| | TNRMALS | 43 |
| | ERDRTRG | 21 |
| | SGTFVKA | 33 |
| Spinal Cord, Thoracic | NSVRPLT | 23 |
| | SGTFVKA | 33 |
| | RPGREAS | 144 |
| | RGVLVTT | 2 |
| | RDATRSS | 12 |
| | TAPKSLK | 25 |
| | DKTRAGS | 5 |

TABLE 1-continued

AAV1 targeting peptides for each brain structure.

| Region | Peptide | SEQ ID NO |
|---|---|---|
| Spinal Cord, Lumbar | RPGREAS | 144 |
| | TATPRKG | 49 |
| | TAPKSLK | 25 |
| | RDATRSS | 12 |
| | KAAGRTV | 46 |
| Spinal Cord, Cervical | SGVLVQR | 32 |
| | NSVRPLT | 23 |
| | RPGREAS | 144 |
| | RGVLVTT | 2 |
| | SGTFVKA | 33 |
| | TAPKSLK | 25 |
| | RDATRSS | 12 |
| | DKTRAGS | 5 |
| Substantia Nigra | RGVLVTT | 2 |
| | GITLGRL | 44 |
| | RPGRESA | 3 |
| | PIPAGKK | 9 |
| | AGIMVRV | 45 |
| | SGVLVQR | 32 |
| | VSLKERV | 29 |
| | RDSTRQL | 26 |
| | RPGREAS | 144 |
| | RDATRSS | 12 |
| Subthalamic Nuclei | KAAGRTV | 46 |
| | RDATRSS | 12 |
| | RGVLVTT | 2 |
| | RPGRESA | 3 |
| | HVIRLPS | 47 |
| | EVKGKGK | 16 |
| | NESLKKK | 4 |
| | DETSRLV | 30 |
| | NSVRPLT | 23 |
| | SGTFVKA | 33 |
| | PIPAGKK | 9 |
| | VKALGRP | 39 |
| Temporal Cortex | NSVRPLT | 23 |
| | RPGREAS | 144 |
| | TAPKSLK | 25 |
| | RDATRSS | 12 |
| | DKTRAGS | 5 |
| Thalamus | GRETLKG | 8 |
| | RPGREQA | 1 |
| | ERDRTRG | 21 |
| | RGVLVTT | 2 |
| | SVASAKK | 48 |
| | TATPRKG | 49 |
| | RDATRSS | 12 |
| | NVTIKSK | 28 |
| | TKTGLKL | 50 |
| | KGLRTPT | 51 |
| Thalamus, Anterior | SGVLVQR | 32 |
| | NSVHNTA | 18 |
| | PIPAGKK | 9 |
| | DETSRLV | 30 |
| | AKLNKSS | 17 |
| | RPGREAS | 144 |
| VA/VL Thalamus | RGVLVTT | 2 |
| | DKTRAGS | 5 |
| | DETSRLV | 30 |
| | RDSTRQL | 26 |
| | NKIHANP | 24 |
| | TAPKSLK | 25 |
| Visual Cortex | RPGREAS | 144 |
| | NSVRPLT | 23 |
| | TAPKSLK | 25 |
| | RDATRSS | 12 |

TABLE 1-continued

AAV1 targeting peptides for each brain structure.

| Region | Peptide | SEQ ID NO |
|---|---|---|
| | NSVHNTA | 18 |
| | DKTRAGS | 5 |

TABLE 2

AAV2 targeting peptides for each brain structure.

| Region | Peptide | SEQ ID NO |
|---|---|---|
| Brainstem | LTSRTSP | 52 |
| | DDPSARR | 53 |
| | GEQDLRR | 54 |
| | VSTALPR | 55 |
| | RDDVPLR | 56 |
| | TRVGTAG | 57 |
| | SSSKTGS | 58 |
| | SLSTGPK | 59 |
| | VQGRQGG | 60 |
| Caudate | RGASGAV | 61 |
| | NARAQGV | 62 |
| | TSNRGQV | 63 |
| | AVRGGMA | 64 |
| | RGLDKGT | 65 |
| | KGVDLKP | 66 |
| | TAVREER | 67 |
| | GNAGITK | 68 |
| | SLSTGPK | 59 |
| | SARAGAP | 69 |
| | GSRAGVG | 105 |
| | NARPVSA | 76 |
| | HDGGASR | 103 |
| | VTQSKGA | 74 |
| | KAQGVGG | 79 |
| | ESTGRER | 73 |
| Cerebellar Cortex | SGEFVGR | 70 |
| | SGRKLEV | 71 |
| | SARSGSV | 72 |
| | ESTGRER | 73 |
| | SSSKTGS | 58 |
| | RDDVPLR | 56 |
| | VQGRQGG | 60 |
| | VTQSKGA | 74 |
| | RGSGSAV | 75 |
| Cerebellar Cortex; Vermis | HDGGASR | 103 |
| | EAQSHPR | 91 |
| | ESTGRER | 73 |
| | GRSTGMT | 95 |
| | GSRAGVG | 105 |
| Cerebellum; right upper vermis | HDGGASR | 103 |
| | RAVPAGG | 84 |
| | RSNAPQT | 90 |
| | TKSLSSG | 92 |
| | ESTGRER | 73 |
| | RGSTQVG | 94 |
| Cerebellum; lateral to brainstem (right) | HDGGASR | 103 |
| | ESTGRER | 73 |
| | KAQGVGG | 79 |
| | EAQSHPR | 91 |
| | RAVPAGG | 84 |
| | RDDVPLR | 56 |
| Cerebellar Left hemisphere adjacent to upper vermis | HDGGASR | 103 |
| | ESTGRER | 73 |
| | EAQSHPR | 91 |
| | NARAQGV | 62 |
| | LTSRTSP | 52 |
| | KAQGVGG | 79 |

13

TABLE 2-continued

AAV2 targeting peptides for each brain structure.

| Region | Peptide | SEQ ID NO |
|---|---|---|
| Cerebellar Left hemisphere Most lateral point | HDGGASR | 103 |
| | ESTGRER | 73 |
| | EAQSHPR | 91 |
| | KAQGVGG | 79 |
| | GSRAGVG | 105 |
| Cerebellar Left hemisphere Adjacent to brain stem | ESTGRER | 73 |
| | HDGGASR | 103 |
| | EAQSHPR | 91 |
| | GSRAGVG | 105 |
| | KAQGVGG | 79 |
| | GRGGAAL | 100 |
| Cerebral Cortex | DDPSARR | 53 |
| | NARPVSA | 76 |
| | TSNRGQV | 63 |
| | NARAQGV | 62 |
| | TARGGGG | 77 |
| | KGVDLKP | 66 |
| | GRSASGS | 78 |
| | SSSKTGS | 58 |
| | KAQGVGG | 79 |
| | VQGROGG | 60 |
| Cochlea (ear) | HDGGASR | 103 |
| | KAQGVGG | 79 |
| | RSNAPQT | 90 |
| | LTSRTSP | 52 |
| | EAQSHPR | 91 |
| Deep Cerebellar Nuclei | GSRAGVG | 105 |
| | RAVPAGG | 84 |
| | EAQSHPR | 91 |
| | AVRGGMA | 64 |
| | VPGRTAG | 81 |
| | VTQSKGA | 74 |
| Dorsal Root Ganglia Lumbar | HDGGASR | 103 |
| | TKSLSSG | 92 |
| | KAQGVGG | 79 |
| | GSRAGVG | 105 |
| | VPGRTAG | 81 |
| Dorsal Root Ganglia Cervical | GRSTGMT | 95 |
| | AVRGGMA | 64 |
| | HDGGASR | 103 |
| | TAAGGQR | 99 |
| | KAQGVGG | 79 |
| Dorsal Root Ganglia Thoracic | HDGGASR | 103 |
| | GSRAGVG | 105 |
| | ARGSGVN | 82 |
| | RAVPAGG | 84 |
| | KAQGVGG | 79 |
| Ependyma | GRGAPGG | 80 |
| | DDPSARR | 53 |
| | TSNRGQV | 63 |
| | RGSGSAV | 75 |
| | VQGROGG | 60 |
| | VTQSKGA | 74 |
| | NARPVSA | 76 |
| | KGVDLKP | 66 |
| | NARAQGV | 62 |
| | TARGGGG | 77 |
| Ependyma; 4th Ventrical | GSRAGVG | 105 |
| | RDDVPLR | 56 |
| | RGSTQVG | 94 |
| | KAQGVGG | 79 |
| | GRGGAAL | 100 |
| Ependyma; Lt Ventrical | HDGGASR | 103 |
| | ESTGRER | 73 |
| | EAQSHPR | 91 |

14

TABLE 2-continued

AAV2 targeting peptides for each brain structure.

| Region | Peptide | SEQ ID NO |
|---|---|---|
| | NARPVSA | 76 |
| | KAQGVGG | 79 |
| Ependyma; 3rd Ventrical | GRSTGMT | 95 |
| | LTSRTSP | 52 |
| | KAQGVGG | 79 |
| | GRGGAAL | 100 |
| | EAQSHPR | 91 |
| | ARGSGVN | 82 |
| Globus Pallidus | VQGROGG | 60 |
| | VPGRTAG | 81 |
| | ARGSGVN | 82 |
| | SVRVGGQ | 83 |
| | RGSGSAV | 75 |
| | RAVPAGG | 84 |
| | VMSSGKP | 85 |
| | STPAPKS | 86 |
| | RGGAQVV | 87 |
| Globus Pallidus External | EAQSHPR | 91 |
| | GSRAGVG | 105 |
| | VQGRQGG | 60 |
| | ESTGRER | 73 |
| | GRGGAAL | 100 |
| | KASGAGG | 88 |
| Globus Pallidus Internal | RDDVPLR | 56 |
| | GSRAGVG | 105 |
| | GAVGGVK | 107 |
| | DDPSARR | 53 |
| | RGSTQVG | 94 |
| | KAQGVGG | 79 |
| Hippocampus | DDPSARR | 53 |
| | KASGAGG | 88 |
| | KAQGVGG | 79 |
| | TSNRGQV | 63 |
| | VQGRQGG | 60 |
| | VSTALPR | 55 |
| | TGTAGLK | 89 |
| | NARPVSA | 76 |
| | SSSKTGS | 58 |
| Hippocampus; CA1 | VAPISKS | 101 |
| | HDGGASR | 103 |
| | LTSRTSP | 52 |
| | ESTGRER | 73 |
| | KAQGVGG | 79 |
| Hippocampus; CA3 | VQGROGG | 60 |
| | GRSTGMT | 95 |
| | GRGGAAL | 100 |
| | KAQGVGG | 79 |
| | RGSTQVG | 94 |
| | TSNRGQV | 63 |
| Hippocampus; DG | HDGGASR | 103 |
| | ESTGRER | 73 |
| | RGSTQVG | 94 |
| | EAQSHPR | 91 |
| | KAQGVGG | 79 |
| | GSRAGVG | 105 |
| Inferior Olive | VPGRTAG | 81 |
| | HDGGASR | 103 |
| | VQGROGG | 60 |
| | GSRAGVG | 105 |
| | RDDVPLR | 56 |
| | KAQGVGG | 79 |
| Lateral geniculate nuclei | HDGGASR | 103 |
| | ESTGRER | 73 |
| | GSRAGVG | 105 |
| | KAQGVGG | 79 |

TABLE 2-continued

AAV2 targeting peptides for each brain structure.

| Region | Peptide | SEQ ID NO |
|---|---|---|
| | EAQSHPR | 91 |
| | VPGRTAG | 81 |
| Meninges | SSSKTGS | 58 |
| | NARPVSA | 76 |
| | RSNAPQT | 90 |
| | EAQSHPR | 91 |
| | TKSLSSG | 92 |
| | GRGAPGG | 80 |
| | AAGAKVM | 93 |
| | ESTGRER | 73 |
| | KGVDLKP | 66 |
| | VQGRQGG | 60 |
| | HDGGASR | 103 |
| | KAQGVGG | 79 |
| | RGSTQVG | 94 |
| | VPGRTAG | 81 |
| | GSRAGVG | 105 |
| Optic Nerve | DDPSARR | 53 |
| | RGGAQVV | 87 |
| | KASGAGG | 88 |
| | RGSGSAV | 75 |
| | VQGROGG | 60 |
| | KAQGVGG | 79 |
| | TRVGTAG | 57 |
| | GEQDLRR | 54 |
| | RGSTQVG | 94 |
| | SSSKTGS | 58 |
| | GSRAGVG | 105 |
| | ESTGRER | 73 |
| | HDGGASR | 103 |
| | RDDVPLR | 56 |
| Pons | ESTGRER | 73 |
| | GSRAGVG | 105 |
| | HDGGASR | 103 |
| | KAQGVGG | 79 |
| | RDDVPLR | 56 |
| | GRGGAAL | 100 |
| Prefrontal Cortex | HDGGASR | 103 |
| | GSRAGVG | 105 |
| | ESTGRER | 73 |
| | KAQGVGG | 79 |
| | RGSTQVG | 94 |
| Primary motor cortex | GSRAGVG | 105 |
| | VPGRTAG | 81 |
| | ESTGRER | 73 |
| | RGSTQVG | 94 |
| | GRGGAAL | 100 |
| | KAQGVGG | 79 |
| Primary Visual Cortex | HDGGASR | 103 |
| | ESTGRER | 73 |
| | EAQSHPR | 91 |
| | TKSLSSG | 92 |
| | GSRAGVG | 105 |
| | KAQGVGG | 79 |
| Putamen | GRSTGMT | 95 |
| | RATSQST | 96 |
| | VGRSVGA | 97 |
| | VQGRQGG | 60 |
| | GEGGGGR | 98 |
| | VSTALPR | 55 |
| | RGASGAV | 61 |
| | TAAGGQR | 99 |
| | SLSTGPK | 59 |
| | GRGGAAL | 100 |
| | RAVPAGG | 84 |
| | KAQGVGG | 79 |
| | GSRAGVG | 105 |
| | VPGRTAG | 81 |

TABLE 2-continued

AAV2 targeting peptides for each brain structure.

| Region | Peptide | SEQ ID NO |
|---|---|---|
| | HDGGASR | 103 |
| | RDDVPLR | 56 |
| Reticular Formation | VTQSKGA | 74 |
| | DDPSARR | 53 |
| | TGTAGLK | 89 |
| | ARGSGVN | 82 |
| | RGSTQVG | 94 |
| | RDDVPLR | 56 |
| Spinal Cord | SLSTGPK | 59 |
| | GRSTGMT | 95 |
| | RGASGAV | 61 |
| | TARGGGG | 77 |
| | KASGAGG | 88 |
| | VAPISKS | 101 |
| | DDPSARR | 53 |
| | TSNRGQV | 63 |
| | SSSKTGS | 58 |
| | VQGROGG | 60 |
| Spinal Cord Thoracic | HDGGASR | 103 |
| | ESTGRER | 73 |
| | EAQSHPR | 91 |
| | GSRAGVG | 105 |
| | VQGROGG | 60 |
| | KAQGVGG | 79 |
| Spinal Cord Lumbar | HDGGASR | 103 |
| | EAQSHPR | 91 |
| | DDPSARR | 53 |
| | KLSISGN | 106 |
| | VMSSGKP | 85 |
| | KAQGVGG | 79 |
| | TSNRGQV | 63 |
| Spinal Cord Cervical | ESTGRER | 73 |
| | HDGGASR | 103 |
| | EAQSHPR | 91 |
| | GSRAGVG | 105 |
| | RGSTQVG | 94 |
| | KAQGVGG | 79 |
| Substantia Nigra | LTSRTSP | 52 |
| | NARPVSA | 76 |
| | SSSKTGS | 58 |
| | RGGAQVV | 87 |
| | APPVKLS | 102 |
| | DDPSARR | 53 |
| | RGSGSAV | 75 |
| | HDGGASR | 103 |
| | TRVGTAG | 57 |
| | GSRAGVG | 105 |
| | KLSISGN | 106 |
| | KAQGVGG | 79 |
| | TGTAGLK | 89 |
| | ARGSGVN | 82 |
| Subthalamic Nuclei | VQGRQGG | 60 |
| | RSGGAAV | 104 |
| | KASGAGG | 88 |
| | SSSKTGS | 58 |
| | KAQGVGG | 79 |
| | GSRAGVG | 105 |
| | RGGAQVV | 87 |
| | APPVKLS | 102 |
| | RGSGSAV | 75 |
| | TRVGTAG | 57 |
| | RGSTQVG | 94 |
| | KLSISGN | 106 |
| | RDDVPLR | 56 |
| | GRGGAAL | 100 |
| | TSNRGQV | 63 |
| Temporal Cortex | ESTGRER | 73 |
| | HDGGASR | 103 |

TABLE 2-continued

AAV2 targeting peptides for each brain structure.

| Region | Peptide | SEQ ID NO |
|---|---|---|
|  | GSRAGVG | 105 |
|  | KAQGVGG | 79 |
|  | RDDVPLR | 56 |
| Thalamus | KASGAGG | 88 |
|  | RDDVPLR | 56 |
|  | LTSRTSP | 52 |
|  | KLSISGN | 106 |
|  | VSTALPR | 55 |
|  | VMSSGKP | 85 |
|  | GAVGGVK | 107 |
|  | KNESGKV | 108 |
|  | VTQSKGA | 74 |
|  | AGQLAGR | 109 |
| Thalamus, Anterior | RGSTQVG | 94 |
|  | KAQGVGG | 79 |
|  | TKSLSSG | 92 |
|  | RAVPAGG | 84 |
|  | TSNRGQV | 63 |
|  | RDDVPLR | 56 |
| VA/VL Thalamus | TRVGTAG | 57 |
|  | ARGSGVN | 82 |
|  | GRGGAAL | 100 |
|  | NARPVSA | 76 |
|  | VQGRQGG | 60 |
|  | GSRAGVG | 105 |

TABLE 3

AAV9 targeting peptides for each brain structure.

| Region | Peptide | SEQ ID NO |
|---|---|---|
| Brainstem | KGGGFHG | 110 |
|  | RAKPGME | 111 |
|  | GRDVTRS | 112 |
|  | RGDLQWV | 113 |
|  | GGDRTRG | 114 |
|  | RGDLASV | 115 |
|  | RDTTRNL | 116 |
|  | KGGGVHG | 117 |
| Caudate | KGGGFHG | 110 |
|  | RGDLQWV | 113 |
|  | RGDMYRV | 118 |
|  | RGDRPVS | 119 |
|  | RSDVGSL | 120 |
|  | RGDLASV | 115 |
|  | RDTTRNL | 116 |
|  | AGVKPGR | 121 |
|  | KGGGVHG | 117 |
|  | RAKPGME | 111 |
|  | GADRTRG | 127 |
|  | GRDVTRS | 112 |
|  | ARGDGWR | 132 |
|  | RGGGVYG | 126 |
|  | GGDRTRG | 114 |
|  | GRDYTRL | 133 |
| Cortex, Cerebellar | KGGGFHG | 110 |
|  | RGDLQWV | 113 |
|  | RAKPGME | 111 |
|  | RGDWPRG | 122 |
|  | RGDRPVS | 119 |
|  | GGRPGSW | 123 |
|  | RGDYPRS | 124 |
|  | RGDLRFI | 125 |
| Cortex, Cerebral | KGGGFHG | 110 |
|  | RAKPGME | 111 |
|  | RDTTRNL | 116 |

TABLE 3-continued

AAV9 targeting peptides for each brain structure.

| Region | Peptide | SEQ ID NO |
|---|---|---|
|  | RGGGVYG | 126 |
|  | GGDRTRG | 114 |
|  | GADRTRG | 127 |
|  | RGDLQWV | 113 |
|  | RGDLRFI | 125 |
| Cortex, Prefrontal | KGGGFHG | 110 |
|  | MMGRPGR | 136 |
|  | AGVKPGR | 121 |
|  | RGGGVYG | 126 |
|  | RGDLRFI | 125 |
|  | RGDWPRG | 122 |
|  | RGDLQWV | 113 |
|  | RGDRPVS | 119 |
| Cortex, Motor | MMGRPGR | 136 |
|  | KGGGFHG | 110 |
|  | AGVKPGR | 121 |
|  | RGGGVYG | 126 |
|  | RGDLRFI | 125 |
|  | RGDWPRG | 122 |
|  | RGDLQWV | 113 |
| Cortex, Temporal | KGGGFHG | 110 |
|  | RGGGVYG | 126 |
|  | MMGRPGR | 136 |
|  | RGDLRFI | 125 |
|  | RGDLQWV | 113 |
|  | RGDWPRG | 122 |
| Cortex, Visual | AGVKPGR | 121 |
|  | MMGRPGR | 136 |
|  | RGDLRFI | 125 |
|  | RGDLQWV | 113 |
|  | RGDFMGL | 128 |
|  | RGGGVYG | 126 |
|  | KGGGFHG | 110 |
|  | AWDGTRV | 131 |
| Cochlea (ear) | MMGRPGR | 136 |
|  | KGGGFHG | 110 |
|  | RGDLASV | 115 |
|  | AGVKPGR | 121 |
|  | GGRPGSW | 123 |
|  | RGGGVYG | 126 |
|  | GGDRTRG | 114 |
| Deep Cerebellar Nuclei | RSDVGSL | 120 |
|  | KGGGFHG | 110 |
|  | RGDLQWV | 113 |
|  | GRDVTRS | 112 |
|  | RGDLRFI | 125 |
|  | RGGGVYG | 126 |
|  | RAKPGME | 111 |
| Dorsal Root Ganglia Lumbar | MMGRPGR | 136 |
|  | AGVKPGR | 121 |
|  | GGRPGSW | 123 |
|  | GRDYTRL | 133 |
|  | RGGGVYG | 126 |
|  | GGDRTRG | 114 |
| Dorsal Root Ganglia Cervical | RGDLQWV | 113 |
|  | KGGGFHG | 110 |
|  | RRDETRT | 129 |
|  | RGGGVYG | 126 |
|  | GADRTRG | 127 |
|  | RGDRPVS | 119 |
|  | GGDRTRG | 114 |
| Dorsal Root Ganglia Thoracic | MMGRPGR | 136 |
|  | AGVKPGR | 121 |
|  | GGRPGSW | 123 |
|  | GRDYTRL | 133 |
|  | RGDFMGL | 128 |
|  | RGGGVYG | 126 |

TABLE 3-continued

AAV9 targeting peptides for each brain structure.

| Region | Peptide | SEQ ID NO |
|---|---|---|
| | GGDRTRG | 114 |
| | RAKPGME | 111 |
| | AWDGTRV | 131 |
| Ependyma | KGGGFHG | 110 |
| | RGDLQWV | 113 |
| | RAKPGME | 111 |
| | RGDMYRV | 118 |
| | RSDVGSL | 120 |
| | RGDFMGL | 128 |
| | RGDRPVS | 119 |
| Ependyma; 4th Ventrical | RGDLQWV | 113 |
| | RGDLASV | 115 |
| | RSDVGSL | 120 |
| | RGDLRFI | 125 |
| | MDLTKAV | 135 |
| | RGGGVYG | 126 |
| | RAKPGME | 111 |
| | RGDRPVS | 119 |
| | GGDRTRG | 114 |
| Ependyma; Lt Ventrical | MMGRPGR | 136 |
| | RSDVGSL | 120 |
| | AGVKPGR | 121 |
| | GGRPGSW | 123 |
| | RAKPGME | 111 |
| | RGGGVYG | 126 |
| | GRDVTRS | 112 |
| | RGDLQWV | 113 |
| Ependyma; 3rd Ventrical | KGGGVHG | 117 |
| | GADRTRG | 127 |
| | GGDRTRG | 114 |
| | MMGRPGR | 136 |
| | RGDLQWV | 113 |
| | RGGGVYG | 126 |
| | GRDVTRS | 112 |
| Globus Pallidus | KGGGFHG | 110 |
| | RRDETRT | 129 |
| | RAKPGME | 111 |
| | GGDRTRG | 114 |
| | GRDVTRS | 112 |
| | RSDVGSL | 120 |
| | RGDRPVS | 119 |
| Globus Pallidus External | RAKPGME | 111 |
| | RRGDAWS | 134 |
| | RGDMYRV | 118 |
| | RGDLQWV | 113 |
| | GRDVTRS | 112 |
| | RGGGVYG | 126 |
| Globus Pallidus Internal | MDLTKAV | 135 |
| | RDTTRNL | 116 |
| | AWDGTRV | 131 |
| | RGGGVYG | 126 |
| | KGGGVHG | 117 |
| | RGDLQWV | 113 |
| Hippocampus | KGGGFHG | 110 |
| | AESPWER | 130 |
| | RGDLQWV | 113 |
| | RAKPGME | 111 |
| | RRDETRT | 129 |
| | RGDLRFI | 125 |
| | GGRPGSW | 123 |
| | RDTTRNL | 116 |
| Hippocampus CA1 | KGGGFHG | 110 |
| | ARGDGWR | 132 |
| | RGGGVYG | 126 |
| | AWDGTRV | 131 |
| | GADRTRG | 127 |
| | RAKPGME | 111 |

TABLE 3-continued

AAV9 targeting peptides for each brain structure.

| Region | Peptide | SEQ ID NO |
|---|---|---|
| Hippocampus CA3 | RAKPGME | 111 |
| | RRDETRT | 129 |
| | MDLTKAV | 135 |
| | AWDGTRV | 131 |
| | RDTTRNL | 116 |
| | GGDRTRG | 114 |
| | GRDVTRS | 112 |
| | RGGGVYG | 126 |
| Hippocampus; DG | KGGGFHG | 110 |
| | RGDFMGL | 128 |
| | RGGGVYG | 126 |
| | ARGDGWR | 132 |
| | RGDLRFI | 125 |
| | RGDLQWV | 113 |
| | GRDYTRL | 133 |
| Inferior Olive | RRGDAWS | 134 |
| | GGRPGSW | 123 |
| | KGGGFHG | 110 |
| | KGGGVHG | 117 |
| | RGDWPRG | 122 |
| | RGGGVYG | 126 |
| | GRDYTRL | 133 |
| | RGDRPVS | 119 |
| Meninges | KGGGFHG | 110 |
| | RGDLQWV | 113 |
| | RAKPGME | 111 |
| | RGDWPRG | 122 |
| | GGDRTRG | 114 |
| | AWDGTRV | 131 |
| | RGDMYRV | 118 |
| | RGDRPVS | 119 |
| | RSDVGSL | 120 |
| | KGGGVHG | 117 |
| | GRDVTRS | 112 |
| | AGVKPGR | 121 |
| | RGGGVYG | 126 |
| Optic Nerve | KGGGFHG | 110 |
| | RAKPGME | 111 |
| | RRDETRT | 129 |
| | RDTTRNL | 116 |
| | GGDRTRG | 114 |
| | ARGDGWR | 132 |
| | KGGGVHG | 117 |
| | RGDLRFI | 125 |
| | RGGGVYG | 126 |
| | AGVKPGR | 121 |
| | RGDLQWV | 113 |
| Pons | KGGGFHG | 110 |
| | RGGGVYG | 126 |
| | RRDETRT | 129 |
| | AGVKPGR | 121 |
| | KGGGVHG | 117 |
| | RAKPGME | 111 |
| | RGDLQWV | 113 |
| | GRDYTRL | 133 |
| Putamen | KGGGFHG | 110 |
| | GRDVTRS | 112 |
| | GADRTRG | 127 |
| | GRDYTRL | 133 |
| | RDTTRNL | 116 |
| | RGDLQWV | 113 |
| | RRGDAWS | 134 |
| | GGRPGSW | 123 |
| | KGGGVHG | 117 |
| | RGDMYRV | 118 |
| | RAKPGME | 111 |
| | RGGGVYG | 126 |
| | GGDRTRG | 114 |
| | RGDRPVS | 119 |

TABLE 3-continued

AAV9 targeting peptides for each brain structure.

| Region | Peptide | SEQ ID NO |
|---|---|---|
| Reticular Formation | MMGRPGR | 136 |
| | GRDVTRS | 112 |
| | GADRTRG | 127 |
| | RAKPGME | 111 |
| | RSDVGSL | 120 |
| | RGGGVYG | 126 |
| | AWDGTRV | 131 |
| Spinal Cord | KGGGFHG | 110 |
| | RGDLQWV | 113 |
| | RGDRPVS | 119 |
| | RGDWPRG | 122 |
| | RSDVGSL | 120 |
| | GGRPGSW | 123 |
| | RRGDAWS | 134 |
| | RGDFMGL | 128 |
| Spinal Cord; Thoracic | KGGGFHG | 110 |
| | RGGGVYG | 126 |
| | RGDLQWV | 113 |
| | RGDLRFI | 125 |
| | RRGDAWS | 134 |
| | RGDRPVS | 119 |
| | GRDYTRL | 133 |
| Spinal Cord; Lumbar | RGDLASV | 115 |
| | KGGGFHG | 110 |
| | RGGGVYG | 126 |
| | MMGRPGR | 136 |
| | RGDLQWV | 113 |
| | AWDGTRV | 131 |
| | RAKPGME | 111 |
| Spinal Cord; Cervical | KGGGFHG | 110 |
| | RGDLRFI | 125 |
| | RGGGVYG | 126 |
| | RRGDAWS | 134 |
| | RGDLQWV | 113 |
| | RGDWPRG | 122 |
| Substantia Nigra | KGGGFHG | 110 |
| | RAKPGME | 111 |
| | GRDVTRS | 112 |
| | GGDRTRG | 114 |
| | RRDETRT | 129 |
| | RGDLQWV | 113 |
| | KGGGVHG | 117 |
| | MDLTKAV | 135 |
| | RRGDAWS | 134 |
| | GGRPGSW | 123 |
| | GADRTRG | 127 |
| | RGGGVYG | 126 |
| Subthalamic Nuclei | KGGGFHG | 110 |
| | RAKPGME | 111 |
| | MDLTKAV | 135 |
| | RGDRPVS | 119 |
| | RGDWPRG | 122 |
| | ARGDGWR | 132 |
| | RGDLQWV | 113 |
| | RSDVGSL | 120 |
| | RGDLASV | 115 |
| | RGGGVYG | 126 |
| Thalamus | KGGGFHG | 110 |
| | GRDVTRS | 112 |
| | GGDRTRG | 114 |
| | RGDLQWV | 113 |
| | GRDYTRL | 133 |
| | RGDLRFI | 125 |
| | MMGRPGR | 136 |
| | TGRPGVW | 137 |

TABLE 3-continued

AAV9 targeting peptides for each brain structure.

| Region | Peptide | SEQ ID NO |
|---|---|---|
| Thalamus, Anterior | MDLTKAV | 135 |
| | GGRPGSW | 123 |
| | RGDLRFI | 125 |
| | RDTTRNL | 116 |
| | RAKPGME | 111 |
| | RGGGVYG | 126 |
| | GRDYTRL | 133 |
| | RGDWPRG | 122 |
| VA/VL Thalamus | RGDWPRG | 122 |
| | GGDRTRG | 114 |
| | RRGDAWS | 134 |
| | RGDLRFI | 125 |
| | RGDYPRS | 124 |
| | RGDRPVS | 119 |
| | RGGGVYG | 126 |

TABLE 4

AAV1 targeting peptides for various organs.

| Organ | Peptide | SEQ ID NO |
|---|---|---|
| Brain | RPGREAS | 144 |
| | TAPKSLK | 25 |
| | RDATRSS | 12 |
| | DKTRAGS | 5 |
| | NSVRPLT | 23 |
| | RDSTRQL | 26 |
| | RGVLVTT | 2 |

TABLE 5

AAV2 targeting peptides for various organs.

| Organ | Peptide | SEQ ID NO |
|---|---|---|
| Brain | HDGGASR | 103 |
| | KAQGVGG | 79 |
| | GSRAGVG | 105 |
| | ESTGRER | 73 |
| | RDDVPLR | 56 |
| | RGSTQVG | 94 |
| | EAQSHPR | 91 |
| Kidney | GSRAGVG | 105 |
| | TSNRGQV | 63 |
| | GRSTGMT | 95 |
| | GRGAPGG | 80 |
| | GAVGGVK | 107 |
| | KAQGVGG | 79 7 |
| | RDDVPLR | 56 |
| Heart | HDGGASR | 103 |
| | SLSTGPK | 59 |
| | GSRAGVG | 105 |
| | RGSTQVG | 94 |
| | NARAQGV | 62 |
| | ESTGRER | 73 |
| Liver | KAQGVGG | 79 |
| | GSRAGVG | 105 |
| | RDDVPLR | 56 |
| | HDGGASR | 103 |
| | NARPVSA | 76 |
| Gonad | VPGRTAG | 81 |
| | KAQGVGG | 79 |
| | RGSTQVG | 94 |
| | HDGGASR | 103 |

TABLE 5-continued

| AAV2 targeting peptides for various organs. | | |
|---|---|---|
| Organ | Peptide | SEQ ID NO |
| | GAVGGVK | 107 |
| | RDDVPLR | 56 |
| Spleen | KAQGVGG | 79 |
| | GSRAGVG | 105 |
| | GRGGAAL | 100 |
| | VPGRTAG | 81 |
| | ESTGRER | 73 |
| Lung | ESTGRER | 73 |
| | TKSLSSG | 92 |
| | RGSTQVG | 94 |
| | KAQGVGG | 79 |
| | NARPVSA | 76 |

TABLE 6

| AAV9 targeting peptides for various organs. | | |
|---|---|---|
| Organ | Peptide | SEQ ID NO |
| Brain | RGGGVYG | 126 |
| | RAKPGME | 111 |
| | KGGGFHG | 110 |
| | GGDRTRG | 114 |
| | MMGRPGR | 136 |
| | RGDLQWV | 113 |
| | MDLTKAV | 135 |
| | GGRPGSW | 123 |
| Kidney | MMGRPGR | 136 |
| | RGDLQWV | 113 |
| | RAKPGME | 111 |
| | RSDVGSL | 120 |
| | KGGGFHG | 110 |
| | RGGGVYG | 126 |
| Heart | GGRPGSW | 123 |
| | RSDVGSL | 120 |
| | RGDLASV | 115 |
| | KGGGFHG | 110 |
| | GRDYTRL | 133 |
| | RGGGVYG | 126 |
| | RAKPGME | 111 |
| Liver | GGDRTRG | 114 |
| | GRDVTRS | 112 |
| | RDTTRNL | 116 |
| | RRDETRT | 129 |
| | RSDVGSL | 120 |
| | RGGGVYG | 126 |
| | RAKPGME | 111 |
| | GRDYTRL | 133 |
| Gonad | KGGGVHG | 117 |
| | KGGGFHG | 110 |
| | RSDVGSL | 120 |
| | GGRPGSW | 123 |
| | RRDETRT | 129 |
| | RGGGVYG | 126 |
| | GGDRTRG | 114 |
| | RGDRPVS | 119 |
| | RAKPGME | 111 |

I. Adeno-Associated Virus (AAV) Vectors

Adeno-associated virus (AAV) is a small nonpathogenic virus of the parvoviridae family. To date, numerous serologically distinct AAVs have been identified, and more than a dozen have been isolated from humans or primates. AAV is distinct from other members of this family by its dependence upon a helper virus for replication.

AAV genomes can exist in an extrachromosomal state without integrating into host cellular genomes; possess a broad host range; transduce both dividing and non-dividing cells in vitro and in vivo and maintain high levels of expression of the transduced genes. AAV viral particles are heat stable; resistant to solvents, detergents, changes in pH, and temperature; and can be column purified and/or concentrated on CsCl gradients or by other means. The AAV genome comprises a single-stranded deoxyribonucleic acid (ssDNA), either positive- or negative-sensed. The approximately 4.7 kb genome of AAV consists of one segment of single stranded DNA of either plus or minus polarity. The ends of the genome are short inverted terminal repeats (ITRs) that can fold into hairpin structures and serve as the origin of viral DNA replication.

An AAV "genome" refers to a recombinant nucleic acid sequence that is ultimately packaged or encapsulated to form an AAV particle. An AAV particle often comprises an AAV genome packaged with AAV capsid proteins. In cases where recombinant plasmids are used to construct or manufacture recombinant vectors, the AAV vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for plasmid propagation and production, but is not itself packaged or encapsulated into viral particles. Thus, an AAV vector "genome" refers to nucleic acid that is packaged or encapsulated by AAV capsid proteins.

The AAV virion (particle) is a non-enveloped, icosahedral particle approximately 25 nm in diameter that comprises an AAV capsid. The AAV particle comprises an icosahedral symmetry comprised of three related capsid proteins, VP1, VP2 and VP3, which interact together to form the capsid. The genome of most native AAVs often contain two open reading frames (ORFs), sometimes referred to as a left ORF and a right ORF. The right ORF often encodes the capsid proteins VP1, VP2, and VP3. These proteins are often found in a ratio of 1:1:10 respectively, but may be in varied ratios, and are all derived from the right-hand ORF. The VP1, VP2 and VP3 capsid proteins differ from each other by the use of alternative splicing and an unusual start codon. Deletion analysis has shown that removal or alteration of VP1 which is translated from an alternatively spliced message results in a reduced yield of infectious particles. Mutations within the VP3 coding region result in the failure to produce any single-stranded progeny DNA or infectious particles. In certain embodiments, the genome of an AAV particle encodes one, two or all three VP1, VP2 and VP3 polypeptides.

The left ORF often encodes the non-structural Rep proteins, Rep 40, Rep 52, Rep 68 and Rep 78, which are involved in regulation of replication and transcription in addition to the production of single-stranded progeny genomes. Two of the Rep proteins have been associated with the preferential integration of AAV genomes into a region of the q arm of human chromosome 19. Rep68/78 have been shown to possess NTP binding activity as well as DNA and RNA helicase activities. Some Rep proteins possess a nuclear localization signal as well as several potential phosphorylation sites. In certain embodiments the genome of an AAV (e.g., an rAAV) encodes some or all of the Rep proteins. In certain embodiments the genome of an AAV (e.g., an rAAV) does not encode the Rep proteins. In certain embodiments one or more of the Rep proteins can be delivered in trans and are therefore not included in an AAV particle comprising a nucleic acid encoding a polypeptide.

The ends of the AAV genome comprise short inverted terminal repeats (ITR) which have the potential to fold into T-shaped hairpin structures that serve as the origin of viral DNA replication. Accordingly, the genome of an AAV comprises one or more (e.g., a pair of) ITR sequences that flank a single stranded viral DNA genome. The ITR sequences often have a length of about 145 bases each. Within the ITR region, two elements have been described which are believed to be central to the function of the ITR, a GAGC repeat motif and the terminal resolution site (trs). The repeat motif has been shown to bind Rep when the ITR is in either a linear or hairpin conformation. This binding is thought to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The term "recombinant," as a modifier of vector, such as recombinant viral, e.g., lenti- or parvo-virus (e.g., AAV) vectors, as well as a modifier of sequences such as recombinant nucleic acid sequences and polypeptides, means that the compositions have been manipulated (i.e., engineered) in a fashion that generally does not occur in nature. A particular example of a recombinant vector, such as an AAV, retroviral, or lentiviral vector would be where a nucleic acid sequence that is not normally present in the wild-type viral genome is inserted within the viral genome. An example of a recombinant nucleic acid sequence would be where a nucleic acid (e.g., gene) encodes an inhibitory RNA cloned into a vector, with or without 5', 3' and/or intron regions that the gene is normally associated within the viral genome. Although the term "recombinant" is not always used herein in reference to vectors, such as viral vectors, as well as sequences such as polynucleotides, "recombinant" forms including nucleic acid sequences, polynucleotides, transgenes, etc. are expressly included in spite of any such omission.

A recombinant viral "vector" is derived from the wild type genome of a virus by using molecular methods to remove part of the wild type genome from the virus, and replacing with a non-native nucleic acid, such as a nucleic acid sequence. Typically, for example, for AAV, one or both inverted terminal repeat (ITR) sequences of the AAV genome are retained in the recombinant AAV vector. A "recombinant" viral vector (e.g., rAAV) is distinguished from a viral (e.g., AAV) genome, since part of the viral genome has been replaced with a non-native sequence with respect to the viral genomic nucleic acid such a nucleic acid encoding a transactivator or nucleic acid encoding an inhibitory RNA or nucleic acid encoding a therapeutic protein. Incorporation of such non-native nucleic acid sequences therefore defines the viral vector as a "recombinant" vector, which in the case of AAV can be referred to as a "rAAV vector."

In certain embodiments, an AAV (e.g., a rAAV) comprises two ITRs. In certain embodiments, an AAV (e.g., a rAAV) comprises a pair of ITRs. In certain embodiments, an AAV (e.g., a rAAV) comprises a pair of ITRs that flank (i.e., are at each 5' and 3' end) of a nucleic acid sequence that at least encodes a polypeptide having function or activity.

An AAV vector (e.g., rAAV vector) can be packaged and is referred to herein as an "AAV particle" for subsequent infection (transduction) of a cell, ex vivo, in vitro or in vivo. Where a recombinant AAV vector is encapsulated or packaged into an AAV particle, the particle can also be referred to as a "rAAV particle." In certain embodiments, an AAV particle is a rAAV particle. A rAAV particle often comprises a rAAV vector, or a portion thereof. A rAAV particle can be one or more rAAV particles (e.g., a plurality of AAV particles). rAAV particles typically comprise proteins that encapsulate or package the rAAV vector genome (e.g., capsid proteins). It is noted that reference to a rAAV vector can also be used to reference a rAAV particle.

Any suitable AAV particle (e.g., rAAV particle) can be used for a method or use herein. A rAAV particle, and/or genome comprised therein, can be derived from any suitable serotype or strain of AAV. A rAAV particle, and/or genome comprised therein, can be derived from two or more serotypes or strains of AAV. Accordingly, a rAAV can comprise proteins and/or nucleic acids, or portions thereof, of any serotype or strain of AAV, wherein the AAV particle is suitable for infection and/or transduction of a mammalian cell. Non-limiting examples of AAV serotypes include AAV1, AAV2, AAV3, AAV4, AAV5, AAV6, AAV7, AAV8, AAV9, AAV10, AAV11, AAV12, AAV-rh74, AAV-rh10 and AAV-2M8.

In certain embodiments a plurality of rAAV particles comprises particles of, or derived from, the same strain or serotype (or subgroup or variant). In certain embodiments a plurality of rAAV particles comprise a mixture of two or more different rAAV particles (e.g., of different serotypes and/or strains).

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV variants including capsid variants may not be serologically distinct from a reference AAV or other AAV serotype, they differ by at least one nucleotide or amino acid residue compared to the reference or other AAV serotype.

In certain embodiments, a rAAV vector based upon a first serotype genome corresponds to the serotype of one or more of the capsid proteins that package the vector. For example, the serotype of one or more AAV nucleic acids (e.g., ITRs) that comprises the AAV vector genome corresponds to the serotype of a capsid that comprises the rAAV particle.

In certain embodiments, a rAAV vector genome can be based upon an AAV (e.g., AAV2) serotype genome distinct from the serotype of one or more of the AAV capsid proteins that package the vector. For example, a rAAV vector genome can comprise AAV2 derived nucleic acids (e.g., ITRs), whereas at least one or more of the three capsid proteins are derived from a different serotype, e.g., an AAV1, AAV3, AAV4, AAV5, AAV6, AAV7, AAV8, AAV9, AAV10, AAV11, AAV12, Rh10, Rh74 or AAV-2i8 serotype or variant thereof.

In certain embodiments, a rAAV particle or a vector genome thereof related to a reference serotype has a polynucleotide, polypeptide or subsequence thereof that comprises or consists of a sequence at least 60% or more (e.g., 65%, 70%, 75%, 80%, 85%, 90%, 95%, 96%, 97%, 98%, 99%, 99.1%, 99.2%, 99.3%, 99.4%, 99.5%, etc.) identical to a polynucleotide, polypeptide or subsequence of an AAV1, AAV2, AAV3, AAV4, AAV5, AAV6, AAV7, AAV8, AAV9, AAV10, AAV11, AAV12, Rh10, Rh74 or AAV-2i8 particle. In particular embodiments, a rAAV particle or a vector genome thereof related to a reference serotype has a capsid or ITR sequence that comprises or consists of a sequence at least 60% or more (e.g., 65%, 70%, 75%, 80%, 85%, 90%, 95%, 96%, 97%, 98%, 99%, 99.1%, 99.2%, 99.3%, 99.4%, 99.5%, etc.) identical to a capsid or ITR sequence of an AAV1, AAV2, AAV3, AAV4, AAV5, AAV6, AAV7, AAV8, AAV9, AAV10, AAV11, AAV12, Rh10, Rh74 or AAV-2i8 serotype.

In certain embodiments, a method herein comprises use, administration or delivery of an rAAV1, rAAV2, rAAV3, rAAV4, rAAV5, rAAV6, rAAV7, rAAV8, rAAV9, rAAV10, rAAV11, rAAV12, rRh10, rRh74 or rAAV-2i8 particle.

In certain embodiments, a method herein comprises use, administration or delivery of a rAAV2 particle. In certain embodiments a rAAV2 particle comprises an AAV2 capsid. In certain embodiments a rAAV2 particle comprises one or more capsid proteins (e.g., VP1, VP2 and/or VP3) that are at least 60%, 65%, 70%, 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV2 particle. In certain embodiments a rAAV2 particle comprises VP1, VP2 and VP3 capsid proteins that are at least 75% or more identical, e.g., 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV2 particle. In certain embodiments, a rAAV2 particle is a variant of a native or wild-type AAV2 particle. In some aspects, one or more capsid proteins of an AAV2 variant have 1, 2, 3, 4, 5, 5-10, 10-15, 15-20 or more amino acid substitutions compared to capsid protein(s) of a native or wild-type AAV2 particle.

In certain embodiments a rAAV9 particle comprises an AAV9 capsid. In certain embodiments a rAAV9 particle comprises one or more capsid proteins (e.g., VP1, VP2 and/or VP3) that are at least 60%, 65%, 70%, 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV9 particle. In certain embodiments a rAAV9 particle comprises VP1, VP2 and VP3 capsid proteins that are at least 75% or more identical, e.g., 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV9 particle. In certain embodiments, a rAAV9 particle is a variant of a native or wild-type AAV9 particle. In some aspects, one or more capsid proteins of an AAV9 variant have 1, 2, 3, 4, 5, 5-10, 10-15, 15-20 or more amino acid substitutions compared to capsid protein(s) of a native or wild-type AAV9 particle.

In certain embodiments, a rAAV particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV1, AAV2, AAV3, AAV4, AAV5, AAV6, AAV7, AAV8, AAV9, AAV10, AAV11, AAV12, AAV-rh74, AAV-rh10 or AAV-2i8, as long as they retain one or more desired ITR functions (e.g., ability to form a hairpin, which allows DNA replication; integration of the AAV DNA into a host cell genome; and/or packaging, if desired).

In certain embodiments, a rAAV2 particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV2 particle, as long as they retain one or more desired ITR functions (e.g., ability to form a hairpin, which allows DNA replication; integration of the AAV DNA into a host cell genome; and/or packaging, if desired).

In certain embodiments, a rAAV9 particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV2 particle, as long as they retain one or more desired ITR functions (e.g., ability to form a hairpin, which allows DNA replication; integration of the AAV DNA into a host cell genome; and/or packaging, if desired).

A rAAV particle can comprise an ITR having any suitable number of "GAGC" repeats. In certain embodiments an ITR of an AAV2 particle comprises 1, 2, 3, 4, 5, 6, 7, 8, 9 or 10 or more "GAGC" repeats. In certain embodiments a rAAV2 particle comprises an ITR comprising three "GAGC" repeats. In certain embodiments a rAAV2 particle comprises an ITR which has less than four "GAGC" repeats. In certain embodiments a rAAV2 particle comprises an ITR which has more than four "GAGC" repeats. In certain embodiments an ITR of a rAAV2 particle comprises a Rep binding site wherein the fourth nucleotide in the first two "GAGC" repeats is a C rather than a T.

Exemplary suitable length of DNA can be incorporated in rAAV vectors for packaging/encapsidation into a rAAV particle can about 5 kilobases (kb) or less. In particular, embodiments, length of DNA is less than about 5 kb, less than about 4.5 kb, less than about 4 kb, less than about 3.5 kb, less than about 3 kb, or less than about 2.5 kb.

rAAV vectors that include a nucleic acid sequence that directs the expression of an RNAi or polypeptide can be generated using suitable recombinant techniques known in the art (e.g., see Sambrook et al., 1989). Recombinant AAV vectors are typically packaged into transduction-competent AAV particles and propagated using an AAV viral packaging system. A transduction-competent AAV particle is capable of binding to and entering a mammalian cell and subsequently delivering a nucleic acid cargo (e.g., a heterologous gene) to the nucleus of the cell. Thus, an intact rAAV particle that is transduction-competent is configured to transduce a mammalian cell. A rAAV particle configured to transduce a mammalian cell is often not replication competent, and requires additional protein machinery to self-replicate. Thus, a rAAV particle that is configured to transduce a mammalian cell is engineered to bind and enter a mammalian cell and deliver a nucleic acid to the cell, wherein the nucleic acid for delivery is often positioned between a pair of AAV ITRs in the rAAV genome.

Suitable host cells for producing transduction-competent AAV particles include but are not limited to microorganisms, yeast cells, insect cells, and mammalian cells that can be, or have been, used as recipients of a heterologous rAAV vectors. Cells from the stable human cell line, HEK293 (readily available through, e.g., the American Type Culture Collection under Accession Number ATCC CRL1573) can be used. In certain embodiments a modified human embryonic kidney cell line (e.g., HEK293), which is transformed with adenovirus type-5 DNA fragments, and expresses the adenoviral E1a and E1b genes is used to generate recombinant AAV particles. The modified HEK293 cell line is readily transfected, and provides a particularly convenient platform in which to produce rAAV particles. Methods of generating high titer AAV particles capable of transducing mammalian cells are known in the art. For example, AAV particle can be made as set forth in Wright, 2008 and Wright, 2009.

In certain embodiments, AAV helper functions are introduced into the host cell by transfecting the host cell with an AAV helper construct either prior to, or concurrently with, the transfection of an AAV expression vector. AAV helper constructs are thus sometimes used to provide at least transient expression of AAV rep and/or cap genes to complement missing AAV functions necessary for productive AAV transduction. AAV helper constructs often lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors are known which encode Rep and/or Cap expression products.

An "expression vector" is a specialized vector that contains a gene or nucleic acid sequence with the necessary regulatory regions needed for expression in a host cell. An expression vector may contain at least an origin of replication for propagation in a cell and optionally additional elements, such as a heterologous nucleic acid sequence, expression control element (e.g., a promoter, enhancer), intron, ITR(s), and polyadenylation signal.

II. Therapeutic Agents

In some embodiments, viral gene transfer methods can be used to introduce nucleic acids in mammalian cells or target tissues. Such methods can be used to administer nucleic acids encoding inhibitory RNAs, non-coding RNAs, and/or therapeutic proteins to cells in culture or in a host organism.

A. Inhibitory RNAs

"RNA interference (RNAi)" is the process of sequence-specific, post-transcriptional gene silencing initiated by siRNA. During RNAi, siRNA induces degradation of target mRNA with consequent sequence-specific inhibition of gene expression.

An "inhibitory RNA," "RNAi," "small interfering RNA" or "short interfering RNA" or "siRNA" molecule, "short hairpin RNA" or "shRNA" molecule, or "miRNA" is an RNA duplex of nucleotides that is targeted to a nucleic acid sequence of interest. As used herein, the term "siRNA" is a generic term that encompasses the subset of shRNAs and miRNAs. An "RNA duplex" refers to the structure formed by the complementary pairing between two regions of an RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding huntingtin. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

shRNAs are comprised of stem-loop structures which are designed to contain a 5' flanking region, siRNA region segments, a loop region, a 3' siRNA region and a 3' flanking region. Most RNAi expression strategies have utilized short-hairpin RNAs (shRNAs) driven by strong polIII-based promoters. Many shRNAs have demonstrated effective knock down of the target sequences in vitro as well as in vivo, however, some shRNAs which demonstrated effective knock down of the target gene were also found to have toxicity in vivo.

miRNAs are small cellular RNAs (~22 nt) that are processed from precursor stem loop transcripts. Known miRNA stem loops can be modified to contain RNAi sequences specific for genes of interest. miRNA molecules can be preferable over shRNA molecules because miRNAs are endogenously expressed. Therefore, miRNA molecules are unlikely to induce dsRNA-responsive interferon pathways, they are processed more efficiently than shRNAs, and they have been shown to silence 80% more effectively.

A recently discovered alternative approach is the use of artificial miRNAs (pri-miRNA scaffolds shuttling siRNA sequences) as RNAi vectors. Artificial miRNAs more naturally resemble endogenous RNAi substrates and are more amenable to Pol-II transcription (e.g., allowing tissue-specific expression of RNAi) and polycistronic strategies (e.g., allowing delivery of multiple siRNA sequences). See U.S. Pat. No. 10,093,927, which is incorporated by reference.

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional siRNAs. "Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (~35 nucleotides upstream and ~40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

In designing RNAi there are several factors that need to be considered, such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 80%, 85%, 90%, 95%, 98%, or even 100% identity between the sequence of the siRNA and the gene to be inhibited. Sequences less than about 80% identical to the target gene are substantially less effective. Thus, the greater homology between the siRNA and the gene to be inhibited, the less likely expression of unrelated genes will be affected.

In addition, the size of the siRNA is an important consideration. In some embodiments, the present invention relates to siRNA molecules that include at least about 19-25 nucleotides and are able to modulate gene expression. In the context of the present invention, the siRNA is preferably less than 500, 200, 100, 50, or 25 nucleotides in length. More preferably, the siRNA is from about 19 nucleotides to about 25 nucleotides in length.

A siRNA target generally means a polynucleotide comprising a region that encodes a polypeptide, or a polynucleotide region that regulates replication, transcription, or translation or other processes important to expression of the polypeptide, or a polynucleotide comprising both a region that encodes a polypeptide and a region operably linked thereto that regulates expression. Any gene being expressed in a cell can be targeted. Preferably, a target gene is one involved in or associated with the progression of cellular activities important to disease or of particular interest as a research object.

B. Non-Coding RNAs

As evidenced by cDNA cloning projects and genomic tiling arrays, more than 90% of the human genome undergoes transcription but does not code for proteins. These transcriptional products are referred to as non-protein coding RNAs (ncRNAs). A variety of ncRNA transcripts, such as ribosomal RNAs, transfer RNAs, competing endogenous RNA (ceRNA), small nuclear RNA (snRNA), and small nucleolar RNA (snoRNA), are essential for cell function. Similarly, a large number of short ncRNAs such as microRNAs (miRNAs), endogenous short interfering RNAs (siRNAs), PIWI-interacting RNAs (piRNAs), and small nucleolar RNAs (snoRNAs) are also known to play important regulatory roles in eukaryotic cells. Recent studies have demonstrated a group of long ncRNA (lncRNA) transcripts that exhibit cell type-specific expression and localize into specific subcellular compartments. lncRNAs are also known to play important roles during cellular development and differentiation supporting the view that they have been selected during the evolutionary process.

LncRNAs appear to have many different functions. In many cases, they seem to play a role in regulating the activity or localization of proteins, or serve as organizational frameworks for subcellular structures. In other cases, lncRNAs are processed to yield multiple small RNAs or they may modulate how other RNAs are processed. The latest edition of data produced by the public research consortium GenCode (version #27) catalogs just under 16,000 lncRNAs in the human genome, producing nearly 28,000 transcripts; when other databases are included, more than 40,000 lncRNAs are known.

Interestingly, lncRNAs can influence the expression of specific target proteins at specific genomic loci, modulate the activity of protein binding partners, direct chromatin-modifying complexes to their sites of action, and are post-transcriptionally processed to produce numerous 5'-capped small RNAs. Epigenetic pathways can also regulate the differential expression of lncRNAs.

A growing body of evidence also suggests that aberrantly expressed lncRNAs play important roles in normal physiological processes as well as multiple disease states. lncRNAs are misregulated in various diseases, including ischaemia, heart disease, Alzheimer's disease, psoriasis, and spinocerebellar ataxia type 8. This misregulation has also been shown in various types of cancers, such as breast cancer, colon cancer, prostate cancer, hepatocellular carcinoma and leukemia. Several lncRNAs, e.g. gadd74 and lncRNA-RoR5, modulate cell cycle regulators such as cyclins, cyclin-dependent kinases (CDKs), CDK inhibitors and p53 and thus provide an additional layer of flexibility and robustness to cell cycle progression. In addition, some lncRNAs are linked to mitotic processes such as centromeric satellite RNA, which is essential for kinetochore formation and thus crucial for chromosome segregation during mitosis in humans and flies. Another nuclear lncRNA, MA-lincl, regulates M phase exit by functioning in cis to repress the expression of its neighbouring gene Pura, a regulator of cell proliferation.

lncRNAs are a group that is commonly defined as transcripts of more than 200 nucleotides (e.g. about 200 to about 1200 nt, about 2500 nt, or more) that lack an extended open reading frame (ORF). The term "non-coding RNA" (ncRNA) includes lncRNA as well as shorter transcripts of, e.g., less than about 200 nt, such as about 30 to 200 nt.

Thus, in some embodiments, delivery of a ncRNA, such as to a specific brain structure of interest, corrects aberrant RNA expression levels or modulates levels of disease-causing lncRNA. Accordingly, in some embodiments, the present invention provides an rAAV, wherein the viral genome is engineered to encode a therapeutic non-coding RNA (ncRNA). In some embodiments, the ncRNA is a long non-coding RNA (lncRNA) of about 200 nucleotides (nt) in length or greater. In some embodiments, the therapeutic is a ncRNA of about 25 nt or about 30 nt to about 200 nt in length. In some embodiments, the lncRNA is about 200 nt to about 1,200 nt in length. In some embodiments, the lncRNA is about 200 nt to about 1,100, about 1,000, about 900, about 800, about 700, about 600, about 500, about 400, or about 300 nt in length.

C. CRISPR Systems

Gene editing is a technology that allows for the modification of target genes within living cells. Recently, harnessing the bacterial immune system of CRISPR to perform on demand gene editing revolutionized the way scientists approach genomic editing. The Cas9 protein of the CRISPR system, which is an RNA guided DNA endonuclease, can be engineered to target new sites with relative ease by altering its guide RNA sequence. This discovery has made sequence specific gene editing functionally effective.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes*.

The CRISPR system can induce double stranded breaks (DSBs) at the target site, followed by disruptions as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor (e.g., KRAB) or activator, to affect gene expression. Alternatively, a CRISPR system with a catalytically inactivate Cas9 further comprises a transcriptional repressor or activator fused to a ribosomal binding protein.

In some aspects, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The target sequence may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an "editing template" or "editing polynucleotide" or "editing sequence." In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. The Cas enzyme may be a target gene under the control of a regulated alternative splicing event, as disclosed herein, either as a chimeric target gene minigene or as a target gene for a chimeric minigene transactivator. The gRNA may be under the control of a constitutive promoter.

Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2.

The CRISPR enzyme can be Cas9 (e.g., from *S. pyogenes* or *S. pneumonia*). The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net).

The CRISPR enzyme may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US 20110059502, incorporated herein by reference.

D. Therapeutic Proteins

Some embodiments concern expression of recombinant proteins and polypeptides. In some aspects, the protein or polypeptide may be modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide. It is specifically contemplated that embodiments concerning a "modified protein" may be implemented with respect to a "modified polypeptide," and vice versa.

Recombinant proteins may possess deletions and/or substitutions of amino acids; thus, a protein with a deletion, a protein with a substitution, and a protein with a deletion and a substitution are modified proteins. In some embodiments, these proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region, i.e. a region of the protein determined to be antigenic in a particular organism, such as the organism to which the modified protein is being administered.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A recombinant protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

As used herein, a protein or peptide generally refers, but is not limited to, a protein of greater than about 200 amino acids, up to a full-length sequence translated from a gene; a polypeptide of greater than about 100 amino acids; and/or a peptide of from about 3 to about 100 amino acids. For convenience, the terms "protein," "polypeptide," and "peptide are used interchangeably herein.

As used herein, an "amino acid residue" refers to any naturally occurring amino acid, any amino acid derivative, or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Certain embodiments of the present invention concern fusion proteins. These molecules may have a therapeutic protein linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

III. Methods of Administration

Viral vectors in some aspects may be administered directly to patients (in vivo) or they can be used to treat cells in vitro or ex vivo, and then administered to patients. The term "vector" refers to small carrier nucleic acid molecule, a plasmid, virus (e.g., AAV vector, retroviral vector, lentiviral vector), or other vehicle that can be manipulated by insertion or incorporation of a nucleic acid. Vectors, such as viral vectors, can be used to introduce/transfer nucleic acid sequences into cells, such that the nucleic acid sequence therein is transcribed and, if encoding a protein, subsequently translated by the cells.

Any suitable cell or mammal can be administered or treated by a method or use described herein. Typically, a mammal in need of a method described herein is suspected of having or expressing an abnormal or aberrant protein that is associated with a disease state. Alternative, the mammalian recipient may have a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid or protein components.

Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In certain embodiments a mammal is a human. In certain embodiments a mammal is a non-rodent mammal (e.g., human, pig, goat, sheep, horse, dog, or the like). In certain embodiments a non-rodent mammal is a human. A mammal can be any age or at any stage of development (e.g., an adult, teen, child, infant, or a mammal in utero). A mammal can be male or female. In certain embodiments a mammal can be an animal disease model, for example, animal models having or expressing an abnormal or aberrant protein that is associated with a disease state or animal models with insufficient expression of a protein, which causes a disease state.

Mammals (subjects) treated by a method or composition described herein include adults (18 years or older) and children (less than 18 years of age). Adults include the elderly. Representative adults are 50 years or older. Children range in age from 1-2 years old, or from 2-4, 4-6, 6-18, 8-10, 10-12, 12-15 and 15-18 years old. Children also include infants. Infants typically range from 1-12 months of age.

In certain embodiments, a method includes administering a plurality of viral particles to a mammal as set forth herein, where severity, frequency, progression or time of onset of one or more symptoms of a disease state, such as a neuro-degenerative disease, decreased, reduced, prevented, inhibited or delayed. In certain embodiments, a method includes administering a plurality of viral particles to a mammal to treat an adverse symptom of a disease state, such as a neuro-degenerative disease. In certain embodiments, a method includes administering a plurality of viral particles to a mammal to stabilize, delay or prevent worsening, or progression, or reverse and adverse symptom of a disease state, such as a neuro-degenerative disease.

In certain embodiments a method includes administering a plurality of viral particles to the central nervous system, or portion thereof as set forth herein, of a mammal and severity, frequency, progression or time of onset of one or more symptoms of a disease state, such as a neuro-degenerative disease, are decreased, reduced, prevented, inhibited or delayed by at least about 5 to about 10, about 10 to about 25, about 25 to about 50, or about 50 to about 100 days.

In certain embodiments, a symptom or adverse effect comprises an early stage, middle or late stage symptom; a behavior, personality or language symptom; swallowing, movement, seizure, tremor or fidgeting symptom; ataxia; and/or a cognitive symptom such as memory, ability to organize.

IV. Pharmaceutical Compositions

As used herein the term "pharmaceutically acceptable" and "physiologically acceptable" mean a biologically acceptable composition, formulation, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Such composition, "pharmaceutically acceptable" and "physiologically acceptable" formulations and compositions can be sterile. Such pharmaceutical formulations and compositions may be used, for example in administering a viral particle to a subject.

Such formulations and compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Supplementary active compounds (e.g., preservatives, antibacterial, antiviral and antifungal agents) can also be incorporated into the formulations and compositions.

Pharmaceutical compositions typically contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as surfactants, wetting or emulsifying agents, pH buffering substances, and the like, may be present in such vehicles.

Pharmaceutical compositions can be formulated to be compatible with a particular route of administration or delivery, as set forth herein or known to one of skill in the art. Thus, pharmaceutical compositions include carriers, diluents, or excipients suitable for administration or delivery by various routes.

Pharmaceutical forms suitable for injection or infusion of viral particles can include sterile aqueous solutions or dispersions which are adapted for the extemporaneous preparation of sterile injectable or infusible solutions or dispersions, optionally encapsulated in liposomes. In all cases, the ultimate form should be a sterile fluid and stable under the conditions of manufacture, use and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Isotonic agents, for example, sugars, buffers or salts (e.g., sodium chloride) can be included. Prolonged absorption of injectable compositions can be brought about by the use in the compositions of agents delaying absorption, for example, aluminum monostearate and gelatin.

Solutions or suspensions of viral particles can optionally include one or more of the following components: a sterile diluent such as water for injection, saline solution, such as phosphate buffered saline (PBS), artificial CSF, a surfactants, fixed oils, a polyol (for example, glycerol, propylene glycol, and liquid polyethylene glycol, and the like), glycerin, or other synthetic solvents; antibacterial and antifungal agents such as parabens, chlorobutanol, phenol, ascorbic acid, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Pharmaceutical formulations, compositions and delivery systems appropriate for the compositions, methods and uses of the invention are known in the art (see, e.g., Remington: The Science and Practice of Pharmacy (2003) 20$^{th}$ ed., Mack Publishing Co., Easton, PA; Remington's Pharmaceutical Sciences (1990) 18$^{th}$ ed., Mack Publishing Co., Easton, PA; The Merck Index (1996) 12$^{th}$ ed., Merck Publishing Group, Whitehouse, NJ; Pharmaceutical Principles of Solid Dosage Forms (1993), Technonic Publishing Co., Inc., Lancaster, Pa.; Ansel and Stoklosa, Pharmaceutical Calculations (2001) 11$^{th}$ ed., Lippincott Williams & Wilkins, Baltimore, MD; and Poznansky et al., Drug Delivery Systems (1980), R. L. Juliano, ed., Oxford, N.Y., pp. 253-315).

Viral particles and their compositions may be formulated in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms are dependent upon the number of viral particles believed necessary to produce the desired effect(s). The amount necessary can be formulated in a single dose, or can be formulated in multiple dosage units. The dose may be adjusted to a suitable viral particle concentration, optionally combined with an anti-inflammatory agent, and packaged for use.

In one embodiment, pharmaceutical compositions will include sufficient genetic material to provide a therapeutically effective amount, i.e., an amount sufficient to reduce or ameliorate symptoms or an adverse effect of a disease state in question or an amount sufficient to confer the desired benefit.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Thus, for example, viral particles, and pharmaceutical compositions thereof, can be packaged in single or multiple unit dosage form for ease of administration and uniformity of dosage.

Formulations containing viral particles typically contain an effective amount, the effective amount being readily determined by one skilled in the art. The viral particles may typically range from about 1% to about 95% (w/w) of the composition, or even higher if suitable. The quantity to be administered depends upon factors such as the age, weight and physical condition of the mammal or the human subject considered for treatment. Effective dosages can be established by one of ordinary skill in the art through routine trials establishing dose response curves.

V. Definitions

The terms "polynucleotide," "nucleic acid" and "transgene" are used interchangeably herein to refer to all forms of nucleic acid, oligonucleotides, including deoxyribonucleic acid (DNA) and ribonucleic acid (RNA) and polymers thereof. Polynucleotides include genomic DNA, cDNA and antisense DNA, and spliced or unspliced mRNA, rRNA, tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides can include naturally occurring, synthetic, and intentionally modified or altered polynucleotides (e.g., variant nucleic acid). Polynucleotides can be single stranded, double stranded, or triplex, linear or circular, and can be of any suitable length. In discussing polynucleotides, a sequence or structure of a particular polynucleotide may be described herein according to the convention of providing the sequence in the 5' to 3' direction.

A nucleic acid encoding a polypeptide often comprises an open reading frame that encodes the polypeptide. Unless otherwise indicated, a particular nucleic acid sequence also includes degenerate codon substitutions.

Nucleic acids can include one or more expression control or regulatory elements operably linked to the open reading frame, where the one or more regulatory elements are configured to direct the transcription and translation of the polypeptide encoded by the open reading frame in a mammalian cell. Non-limiting examples of expression control/ regulatory elements include transcription initiation sequences (e.g., promoters, enhancers, a TATA box, and the like), translation initiation sequences, mRNA stability sequences, poly A sequences, secretory sequences, and the like. Expression control/regulatory elements can be obtained from the genome of any suitable organism.

A "promoter" refers to a nucleotide sequence, usually upstream (5') of a coding sequence, which directs and/or controls the expression of the coding sequence by providing the recognition for RNA polymerase and other factors required for proper transcription. A pol II promoter includes a minimal promoter that is a short DNA sequence comprised of a TATA-box and optionally other sequences that serve to specify the site of transcription initiation, to which regulatory elements are added for control of expression. A type 1 pol III promoter includes three cis-acting sequence elements downstream of the transcriptional start site: a) 5' sequence element (A block); b) an intermediate sequence element (I block); c) 3' sequence element (C block). A type 2 pol III promoter includes two essential cis-acting sequence elements downstream of the transcription start site: a) an A box (5' sequence element); and b) a B box (3' sequence element). A type 3 pol III promoter includes several cis-acting promoter elements upstream of the transcription start site, such as a traditional TATA box, proximal sequence element (PSE), and a distal sequence element (DSE).

An "enhancer" is a DNA sequence that can stimulate transcription activity and may be an innate element of the promoter or a heterologous element that enhances the level or tissue specificity of expression. It is capable of operating in either orientation (5'→3' or 3'→5'), and may be capable of functioning even when positioned either upstream or downstream of the promoter.

Promoters and/or enhancers may be derived in their entirety from a native gene, or be composed of different elements derived from different elements found in nature, or even be comprised of synthetic DNA segments. A promoter or enhancer may comprise DNA sequences that are involved in the binding of protein factors that modulate/control effectiveness of transcription initiation in response to stimuli, physiological or developmental conditions.

Non-limiting examples of promoters include SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from non-viral genes, such as the murine metallothionein gene, will also find use herein. Exemplary constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, actin promoter, U6, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others. In addition, sequences derived from intronic miRNA promoters, such as, for example, the miR107, miR206, miR208b, miR548f-2, miR569, miR590, miR566, and miR128 promoter, will also find use herein (see, e.g., Monteys et al., 2010). Accordingly, any of the above-referenced constitutive promoters can be used to control transcription of a heterologous gene insert.

A "transgene" is used herein to conveniently refer to a nucleic acid sequence/polynucleotide that is intended or has been introduced into a cell or organism. Transgenes include any nucleic acid, such as a gene that encodes an inhibitory RNA or polypeptide or protein, and are generally heterologous with respect to naturally occurring AAV genomic sequences.

The term "transduce" refers to introduction of a nucleic acid sequence into a cell or host organism by way of a vector (e.g., a viral particle). Introduction of a transgene into a cell by a viral particle is can therefore be referred to as "transduction" of the cell. The transgene may or may not be integrated into genomic nucleic acid of a transduced cell. If an introduced transgene becomes integrated into the nucleic acid (genomic DNA) of the recipient cell or organism it can be stably maintained in that cell or organism and further passed on to or inherited by progeny cells or organisms of the recipient cell or organism. Finally, the introduced transgene may exist in the recipient cell or host organism extra chromosomally, or only transiently. A "transduced cell" is therefore a cell into which the transgene has been introduced by way of transduction. Thus, a "transduced" cell is a cell into which, or a progeny thereof in which a transgene has been introduced. A transduced cell can be propagated, transgene transcribed and the encoded inhibitory RNA or protein expressed. For gene therapy uses and methods, a transduced cell can be in a mammal.

Transgenes under control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting a suitable promoter (constitutive versus inducible; strong versus weak), it is possible to control both the existence and level of expression of a polypeptide in the genetically modified cell. If the gene encoding the polypeptide is under the control of an inducible promoter, delivery of the polypeptide in situ is triggered by exposing the genetically modified cell in situ to conditions for permitting transcription of the polypeptide, e.g., by intraperitoneal injection of specific inducers of the inducible promoters which control transcription of the agent. For example, in situ expression by genetically modified cells of a polypeptide encoded by a gene under the control of the metallothionein promoter, is enhanced by contacting the genetically modified cells with a solution containing the appropriate (i.e., inducing) metal ions in situ.

A nucleic acid/transgene is "operably linked" when it is placed into a functional relationship with another nucleic acid sequence. A nucleic acid/transgene encoding and RNAi or a polypeptide, or a nucleic acid directing expression of a polypeptide may include an inducible promoter, or a tissue-specific promoter for controlling transcription of the encoded polypeptide. A nucleic acid operably linked to an expression control element can also be referred to as an expression cassette.

In certain embodiments, CNS-specific or inducible promoters, enhancers and the like, are employed in the methods and uses described herein. Non-limiting examples of CNS-specific promoters include those isolated from the genes from myelin basic protein (MBP), glial fibrillary acid protein (GFAP), and neuron specific enolase (NSE). Non-limiting examples of inducible promoters include DNA responsive elements for ecdysone, tetracycline, hypoxia and IFN.

In certain embodiments, an expression control element comprises a CMV enhancer. In certain embodiments, an expression control element comprises a beta actin promoter. In certain embodiments, an expression control element comprises a chicken beta actin promoter. In certain embodiments, an expression control element comprises a CMV enhancer and a chicken beta actin promoter.

As used herein, the terms "modify" or "variant" and grammatical variations thereof, mean that a nucleic acid, polypeptide or subsequence thereof deviates from a reference sequence. Modified and variant sequences may therefore have substantially the same, greater or less expression, activity or function than a reference sequence, but at least retain partial activity or function of the reference sequence. A particular type of variant is a mutant protein, which refers to a protein encoded by a gene having a mutation, e.g., a missense or nonsense mutation.

A "nucleic acid" or "polynucleotide" variant refers to a modified sequence which has been genetically altered compared to wild-type. The sequence may be genetically modified without altering the encoded protein sequence. Alternatively, the sequence may be genetically modified to encode a variant protein. A nucleic acid or polynucleotide variant can also refer to a combination sequence which has been codon modified to encode a protein that still retains at least partial sequence identity to a reference sequence, such as wild-type protein sequence, and also has been codon-modified to encode a variant protein. For example, some codons of such a nucleic acid variant will be changed without altering the amino acids of a protein encoded thereby, and some codons of the nucleic acid variant will be changed which in turn changes the amino acids of a protein encoded thereby.

The terms "protein" and "polypeptide" are used interchangeably herein. The "polypeptides" encoded by a "nucleic acid" or "polynucleotide" or "transgene" disclosed herein include partial or full-length native sequences, as with naturally occurring wild-type and functional polymorphic proteins, functional subsequences (fragments) thereof, and sequence variants thereof, so long as the polypeptide retains some degree of function or activity. Accordingly, in methods and uses of the invention, such polypeptides encoded by nucleic acid sequences are not required to be identical to the endogenous protein that is defective, or whose activity, function, or expression is insufficient, deficient or absent in a treated mammal.

Non-limiting examples of modifications include one or more nucleotide or amino acid substitutions (e.g., about 1 to about 3, about 3 to about 5, about 5 to about 10, about 10 to about 15, about 15 to about 20, about 20 to about 25, about 25 to about 30, about 30 to about 40, about 40 to about 50, about 50 to about 100, about 100 to about 150, about 150 to about 200, about 200 to about 250, about 250 to about 500, about 500 to about 750, about 750 to about 1000 or more nucleotides or residues).

An example of an amino acid modification is a conservative amino acid substitution or a deletion. In particular embodiments, a modified or variant sequence retains at least part of a function or activity of the unmodified sequence (e.g., wild-type sequence).

Another example of an amino acid modification is a targeting peptide introduced into a capsid protein of a viral particle. Peptides have been identified that target recombinant viral vectors, to the central nervous system, such as to distinct brain regions.

A recombinant virus so modified may preferentially bind to one type of tissue (e.g., CNS tissue) over another type of tissue (e.g., liver tissue). In certain embodiments, a recombinant virus bearing a modified capsid protein may "target" brain vascular epithelia tissue by binding at level higher than a comparable, unmodified capsid protein. For example, a recombinant virus having a modified capsid protein may bind to brain vascular epithelia tissue at a level 50% to 100% greater than an unmodified recombinant virus.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein. In certain embodiments, the fragment or portion is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of activity or function of wild-type).

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence. In certain embodiments, the variant is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of activity or function of wild-type).

"Conservative variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

The term "substantial identity" of polynucleotide sequences means that a polynucleotide comprises a sequence that has at least 70%, 71%, 72%, 73%, 74%, 75%, 76%, 77%, 78%, or 79%, or at least 80%, 81%, 82%, 83%, 84%, 85%, 86%, 87%, 88%, or 89%, or at least 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or even at least 95%.

The term "substantial identity" in the context of a polypeptide indicates that a polypeptide comprises a sequence with at least 70%, 71%, 72%, 73%, 74%, 75%, 76%, 77%, 78%, or 79%, or 80%, 81%, 82%, 83%, 84%, 85%, 86%, 87%, 88%, or 89%, or at least 90%, 91%, 92%, 93%, or 94%, or even, 95%, 96%, 97%, 98% or 99%, sequence identity to the reference sequence over a specified comparison window. An indication that two polypeptide sequences are identical is that one polypeptide is immunologically reactive with antibodies raised against the second polypeptide. Thus, a polypeptide is identical to a second polypeptide, for example, where the two peptides differ only by a conservative substitution.

The terms "treat" and "treatment" refer to both therapeutic treatment and prophylactic or preventative measures, wherein the object is to prevent, inhibit, reduce, or decrease an undesired physiological change or disorder, such as the development, progression or worsening of the disorder. For purposes of this invention, beneficial or desired clinical results include, but are not limited to, alleviation of symptoms, diminishment of extent of disease, stabilizing a (i.e., not worsening or progressing) symptom or adverse effect of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those predisposed (e.g., as determined by a genetic assay).

VI. Kits

The invention provides kits with packaging material and one or more components therein. A kit typically includes a label or packaging insert including a description of the components or instructions for use in vitro, in vivo, or ex vivo, of the components therein. A kit can contain a collection of such components, e.g., a nucleic acid, recombinant vector, and/or viral particles.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, or an electrical storage media such as RAM and ROM or hybrids of these such as magnetic/optical storage media, FLASH memory, hybrids and memory type cards.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Identification of AAV Variants that Target Brain Parenchyma

Figure 3:
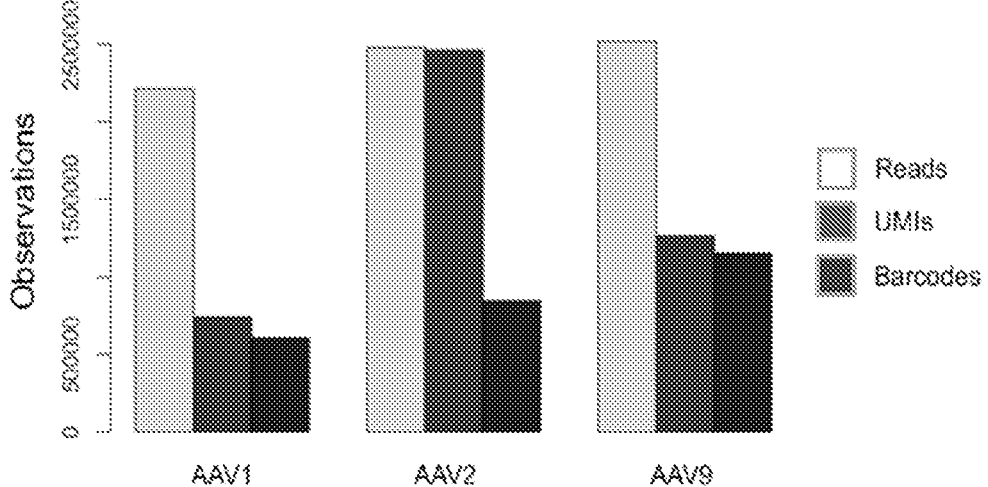
FIG. 3. Graphical representation of input library diversity. Diversity of the input viral library measured from aliquots of AAV1, AAV2, and AAV9 viral vector prior to Round1 ICV injection.

Advanced bar-coded AAV libraries were developed using AAV1, AAV2 and AAV9 capsids as starting platforms. AAV1, AAV2, and AAV9 peptide display libraries were generated by insertion of random sequences at position 590 of AAV1 capsid, position 587 of AAV2 capsid, and position 588 of AAV9 capsid, respectively (FIG. 1). The library had a diversity of $1 \times 10^7$ unique clones (FIG. 3).

To test the utility of the libraries, pilot studies were performed with bench-grade (low titer, low purity) capsid modified AAV2. The AAV2 library was injected intravenously into two C57BL/6 mice at $8 \times 10^{10}$ vector genomes per animal. After 72 hours, the cerebral cortex, cerebellum, and spinal cord were dissected. Of note, heart, skeletal muscle, and diaphragm were separately harvested in order to identify the muscle tropism. Viral genomic DNA was isolated, and the recovered random oligonucleotide sequences were amplified by PCR. The PCR products from brain were pooled to generate the second-round library, which was injected into two mice at $4 \times 10^{10}$ vector genomes per animal. After the second injection, vector genomes were recovered as before and were subjected to NexGen sequencing along with the starting library and $1^{st}$ round tissues. To test if sequences showing enrichment in brain tissues could indeed extend AAV2s reach to the brain, individual hits were cloned into the AAV2 capsid packaging plasmid, and eGFP-expressing AAV2s were generated. Bench-grade vectors were made, and $3 \times 10^{10}$ vector genomes of the AAV2-based capsid modified viruses were injected into mice. Four weeks later, eGFP fluorescence was seen in the brain, even for these low titer variants.

Using these advanced bar-coded AAV libraries, AAV variants that can target distinct primate brain structures in non-human primates were identified. The AAV1, AAV2, and AAV9 libraries were delivered via intracerebroventricular injection to one non-human primate (FIG. 2). Seventy-two hours post-infusion, brain regions were microdissected for viral DNA isolation and AAV DNA amplified by PCR. Products were pooled and used for packaging the 2nd round library, which was infused into an additional NHP. Brain regions were then microdissected 12 days after infusion. After two rounds of panning, vector genomes were recovered and subjected to next generation sequencing. Specifically, genomic DNA extracted from the round1 and round2 tissues was PCR amplified to generate Illumina amplicon sequencing libraries at the position of the vector barcode. The resulting libraries were pooled and run on a single lane of an Illumina HiSeq 4000 using 100 bp single end read chemistry. To illustrate the utility of the approach, several target regions were tested as examples: the ependyma, the meninges and the cerebellum. In general, the sequences directing the AAVx to the ependyma, meninges and cerebellum were different, and different for the various serotypes.

Figure 4:
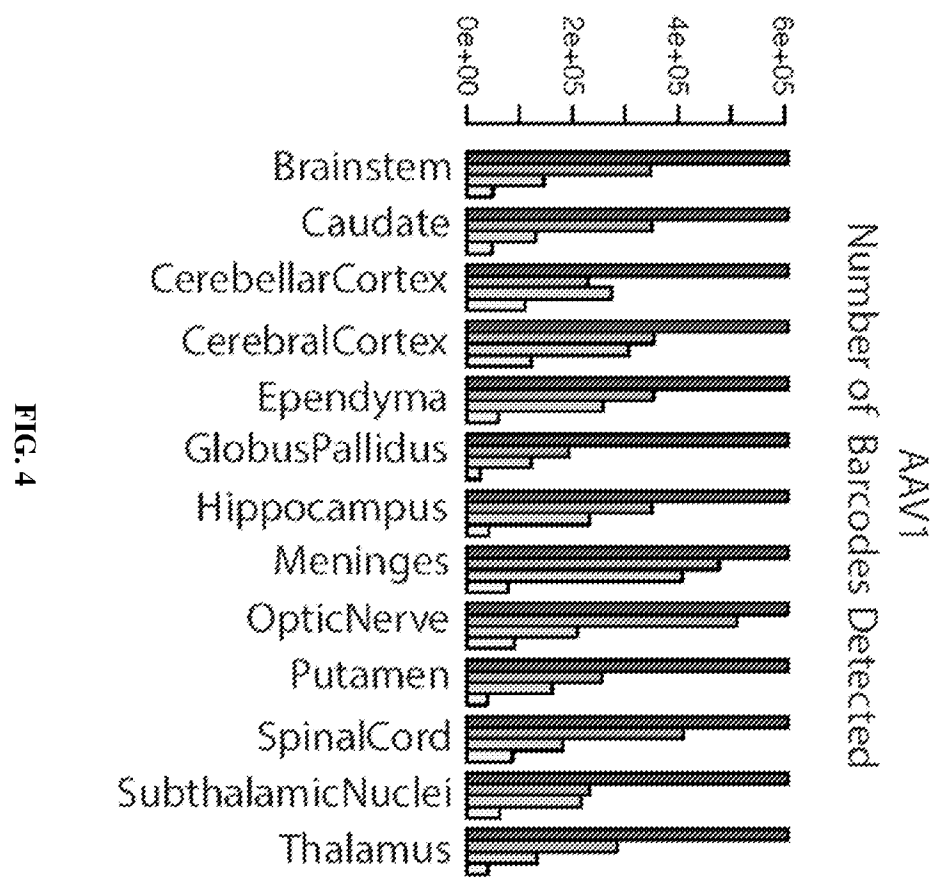
Figure 5:
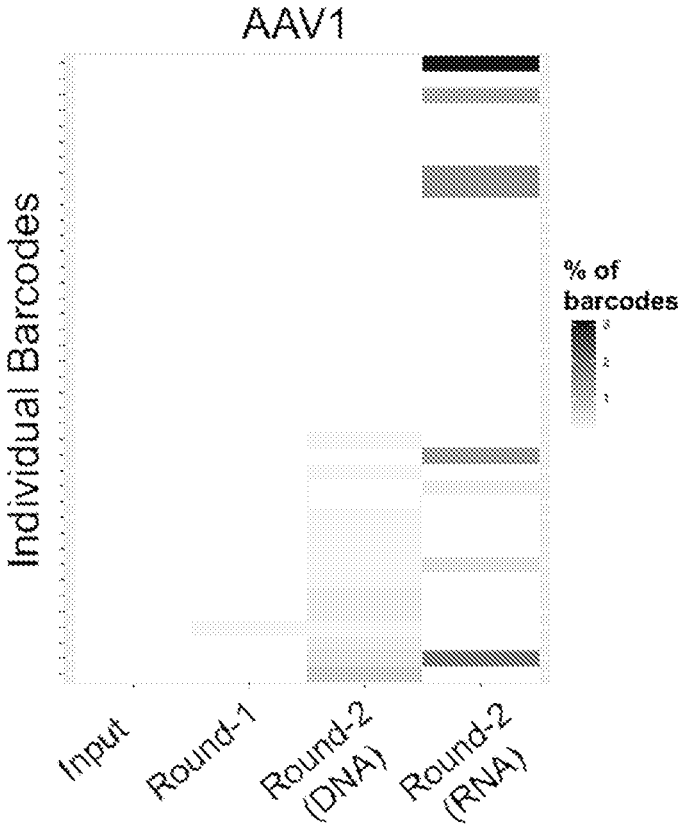
FIG. 5. Illustration of round-over-round enrichment of barcodes in AAV1, AAV2, and AAV9 serotypes for cerebellar cortex.
Figure 6:
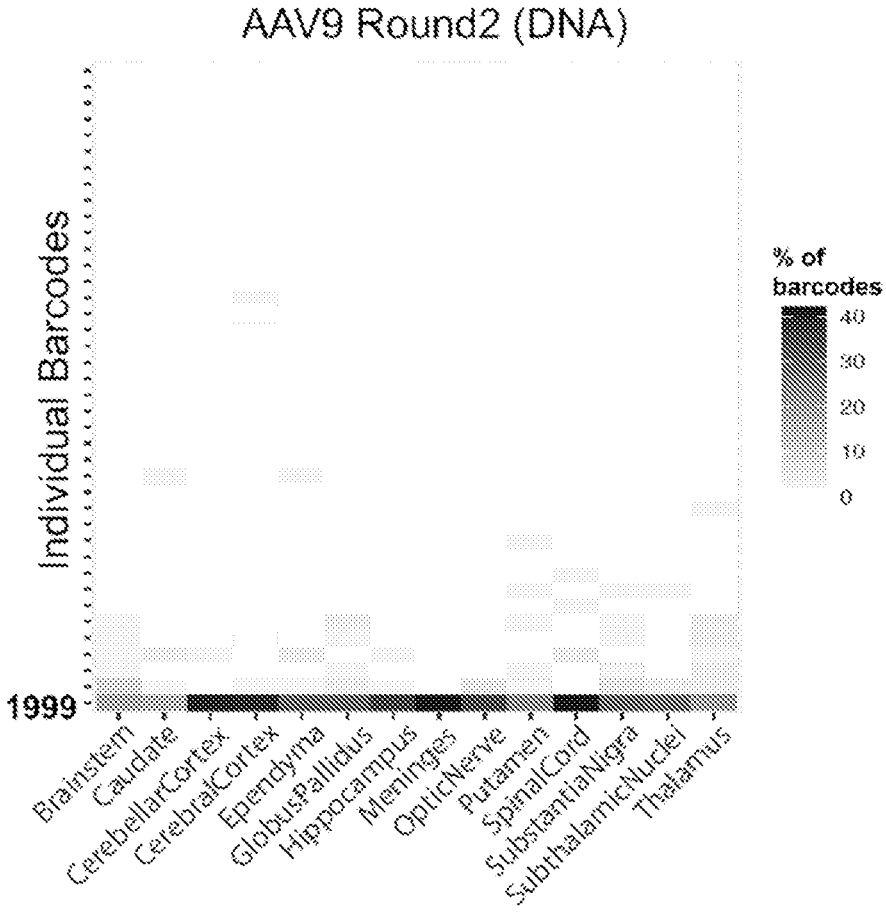
FIG. 6. Illustration of enrichment for AAV9 1999. Heatmap depictions of barcode enrichment from AAV9, cells are colored by the percentage of barcodes detected from the indicated tissue. Barcodes recovered from DNA are shown on the left while barcodes recovered from RNA are on the right.
Figure 7A:
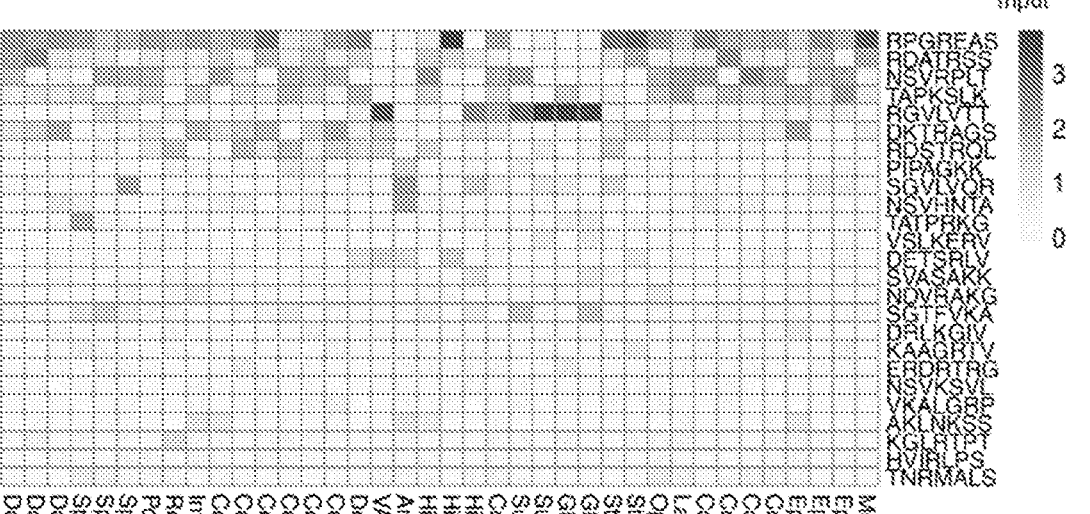
FIGS. 7A-C. Heatmap depictions of pool barcode enrichment from AAV1 (FIG. 7A), AAV2 (FIG. 7B), and AAV9 (FIG. 7C).
Figure 7B:
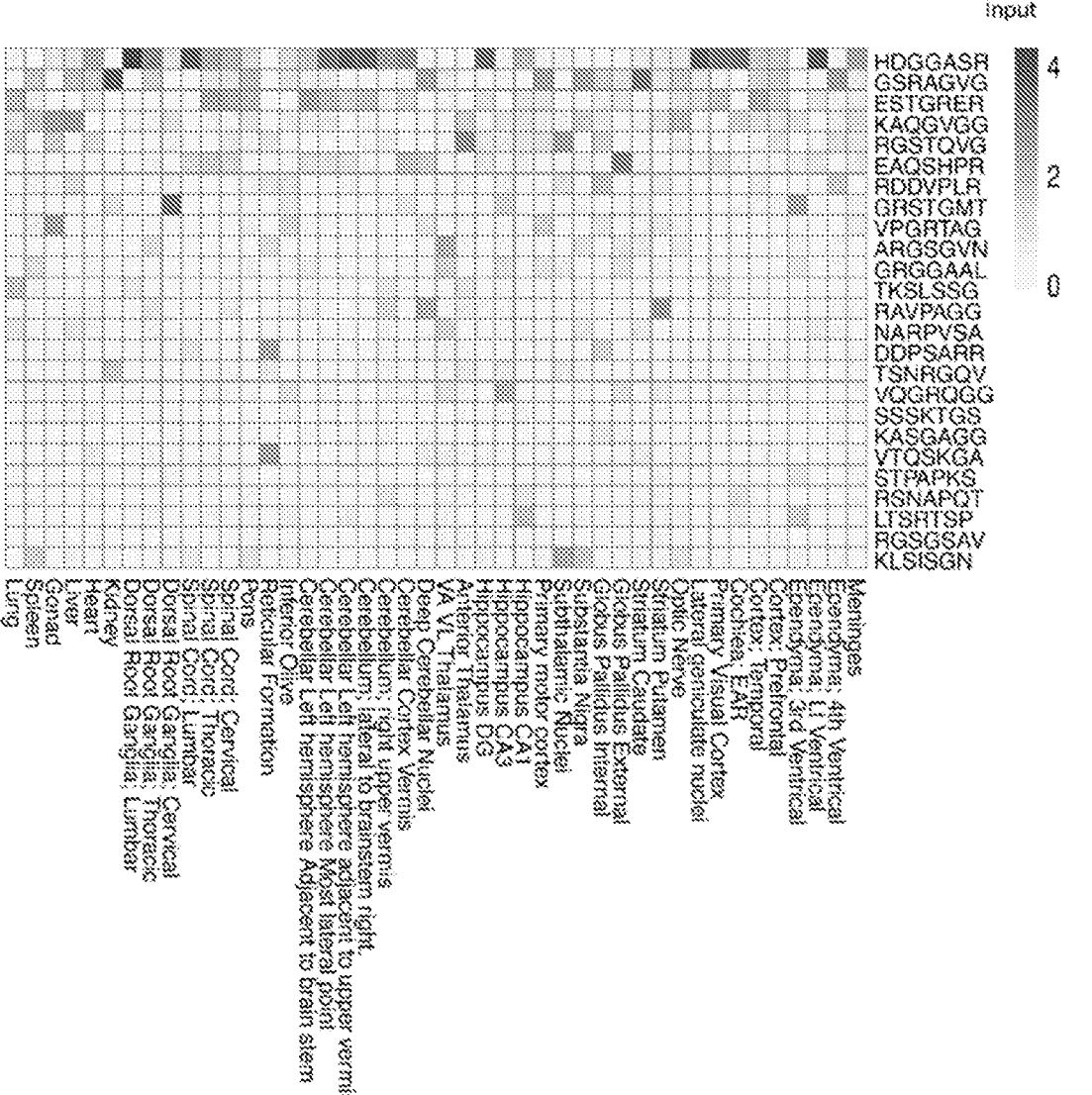
Figure 7C:
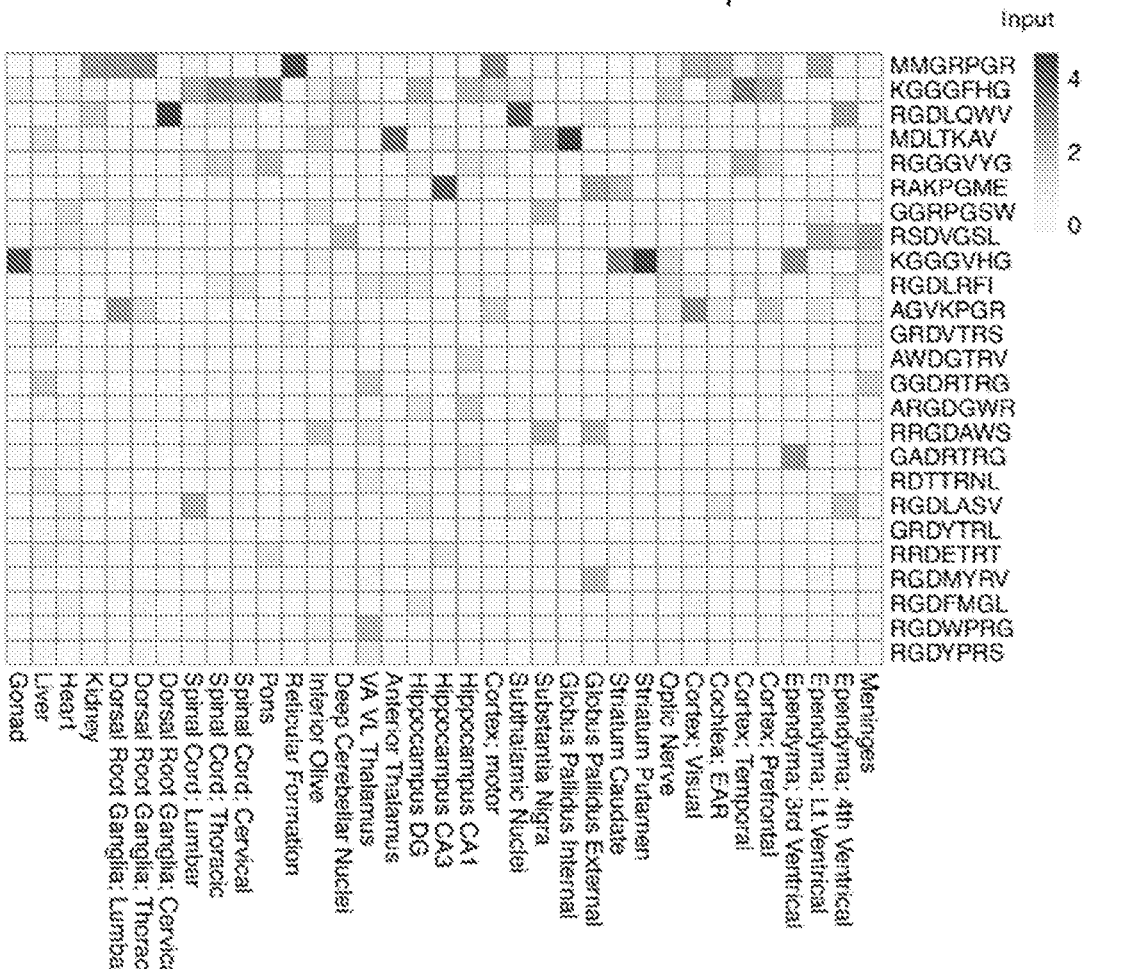

Round-over-Round enrichment graphs (FIG. 4) and heatmaps (FIGS. 5 and 6) were generated for the following tissues: brainstem, caudate, cerebellar cortex (FIG. 5), cerebral cortex, ependyma, globus pallidus, hippocampus, meninges, optic nerve, putamen, spinal cord, substantia nigra, subthalamic nuclei, and thalamus. These illustrate the enrichment of indicated barcodes at baseline (round 0), and after rounds one and two of in vivo passaging through rhesus macaque. To generate these, the fastq results files for each tissue and round combination were processed using a custom Python script designed to extract and quantify unique barcode configurations observed at the DNA level. A custom R script was used to calculate the percentages of barcodes present in each sample and convert DNA barcodes to amino acid barcodes. Table 1 corresponds to samples treated with the AAV1-derived library; Table 2 represents tissues treated with the AAV2-derived library; Table 3 corresponds to samples treated with the AAV9-derived library. Top hits were selected from these three libraries and were assembled and generated into a validation library containing 50 (AAV1), 58 (AAV2), and 30 (AAV9) derived barcodes. This validation library was delivered into an additional Rhesus macaque by ICV injection. Tissues were again collected and processed to facilitate recovery of barcode abundance by deep sequencing. Barcode abundance was evaluated in recovered tissues and the input viral library. Enrichment values for each barcode were calculated relative to their abundance in the input viral library. The resulting relative enrichment values are a robust indicator of vector performance amongst the various tissues evaluated, facilitating identification of broad and specific AAV vector variants (FIGS. 7A-C).

Figure 8:
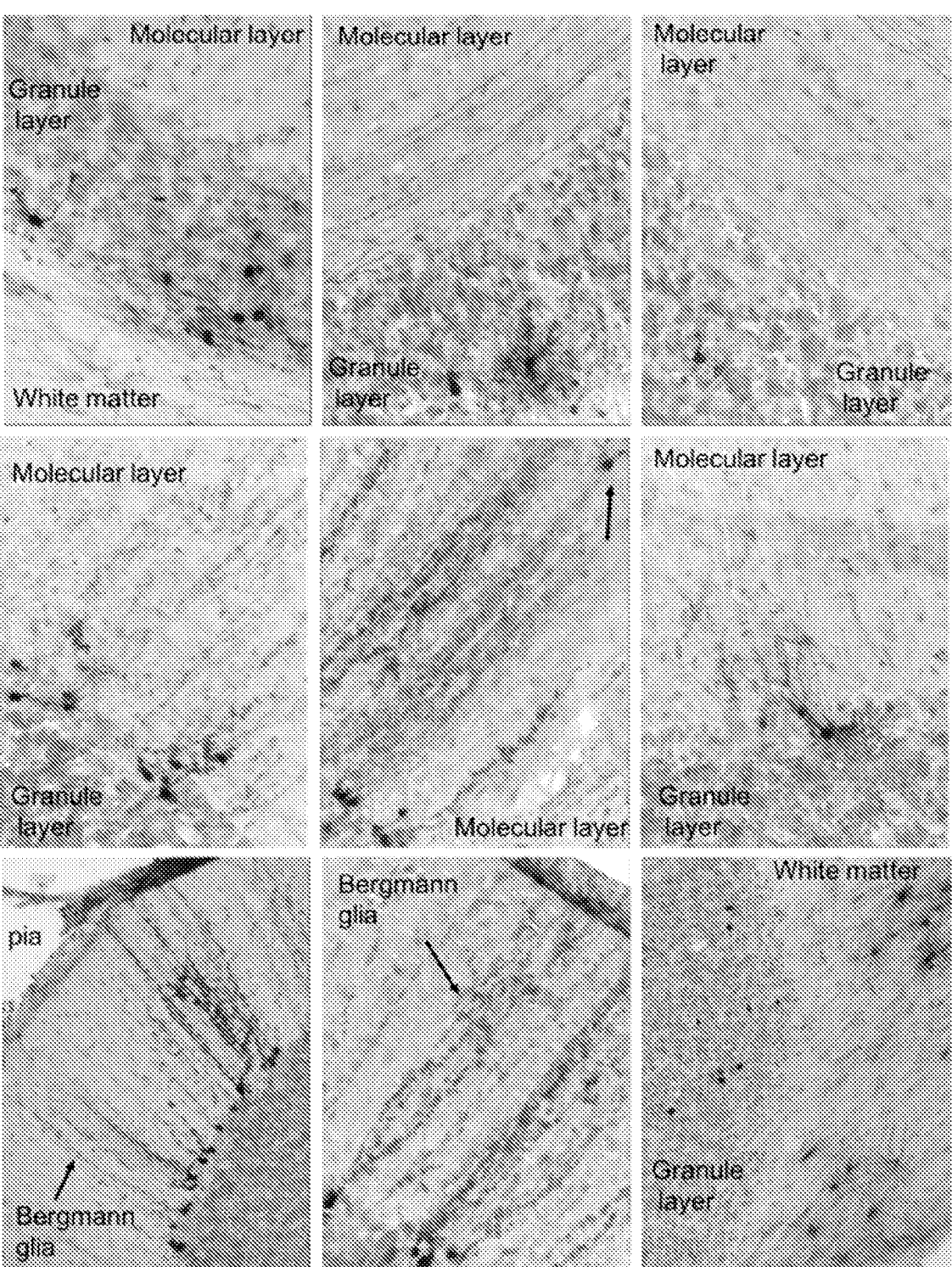
FIG. 8. AAV9 1999 in vivo Rhesus macaque validation. An eGFP expression construct was packaged into AAV9 1999 driven by the CAG promoter. 1.5 E13 vg of AAV9 1999 was delivered to a 5 year old, female Rhesus macaque by ICV injection. Representative images of H&E stained cerebellum depicting the transduction pattern of AAV9 1999 are shown.

In order to validate the identified cell-type specificity, AAV9-1999 (having a targeting peptide sequence of KGGGFHG; SEQ ID NO: 110) was selected for in vivo validation. An eGFP expression construct was packaged into AAV9-1999 driven by the CAG promoter. A 5-year-old, female Rhesus macaque was administered 1.5 E13 vg of AAV9-1999 by ICV injection to the left lateral ventricle. Brain was collected 30 days post-injection for histological analysis. Cerebellum slices were H&E stained to depict the transduction pattern of AAV9-1999 (FIG. 8). The cochlea were also collected from this animal and surprisingly had strong transduction of hair cells. In addition, AAV9-1999 and AAV9 capsids containing the eGFP construct were delivered to C57BL/6 p0 mouse pups by ICV injection at 1 E10 vg per hemisphere. After 21 days, the mice were perfused. Whole mount brains (FIG. 9A), 40 µm whole brain sagittal sections (FIG. 9B), 40 µm S1 cortex sections (FIG. 9C, left), 40 µm hippocampus sections (FIG. 9C, middle), 40 µm cerebellum sagittal sections (FIG. 9C, right), and 40 µm lumbar spinal cord coronal sections (FIG. 9D) were imaged for eGFP fluorescence signal. AAV9-1999 injected into Bl/6 neonate mouse pups showed ubiquitous expression greater than dose-matched injections of AAV9.

One adult rhesus macaque was injected with a mixture of four modified AAVs: AAV9 with a RGDLQWV (SEQ ID NO: 113) targeting peptide sequence and a mTAGBFP2 tag; AAV1 with a ERDRTRG (SEQ ID NO: 21) targeting peptide sequence as a mTFP1 tag; AAV2 with a GRGAPGG (SEQ ID NO: 80) targeting peptide sequence and a mNG tag; and AAV2 with a DDPSARR (SEQ ID NO: 53) targeting peptide sequence and a mRuby3 tag. The viruses were mixed straight at equal volumes to achieve the final total doses for each as follows:

| | |
|---|---|
| AAV9.RGDL mTagBFP2 | 6.13E12 total vg |
| AAV1.ERDR mTFP1 | 1.23E13 total vg |
| AAV2.GRGA mNG | 8.8E12 total vg |
| AAV2.DDPS mRuby3 | 1.32E13 total vg |

Figure 10A:
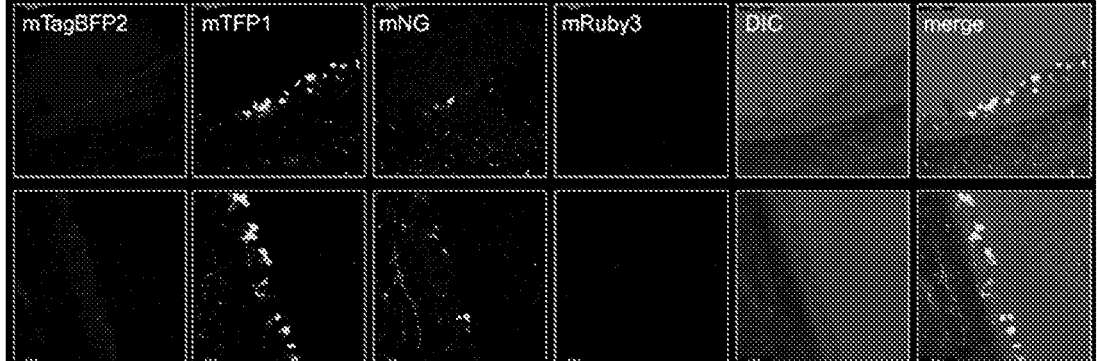
FIGS. 10A-C. Fluorescent images of AAV mixture in vivo Rhesus macaque lateral ventricle (A), fourth ventricle (B), and meninges (C).
Figure 10B:
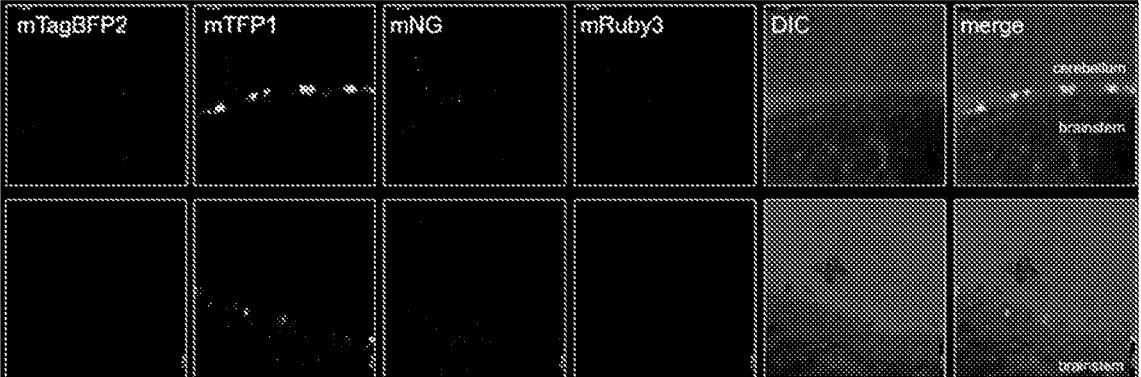
Figure 10C:
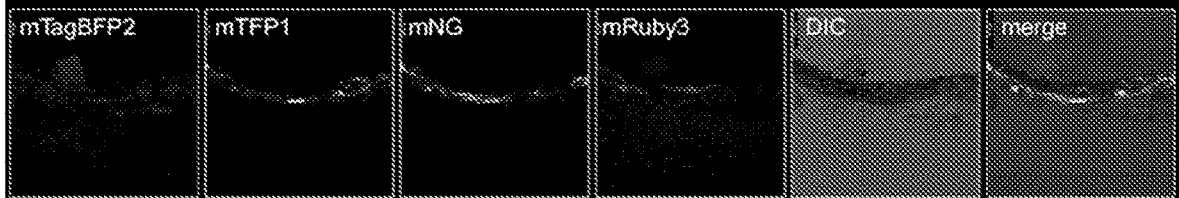

Brain was collected 30 days post-injection for fluorescence imaging. Lateral ventricle sections (FIG. 10A), fourth ventricle sections (FIG. 10B), and meninges sections (FIG. 10C) were imaged for mTagBFP2, mTFP2, mNG, and mRuby3 fluorescence signals.

Figure 11A:
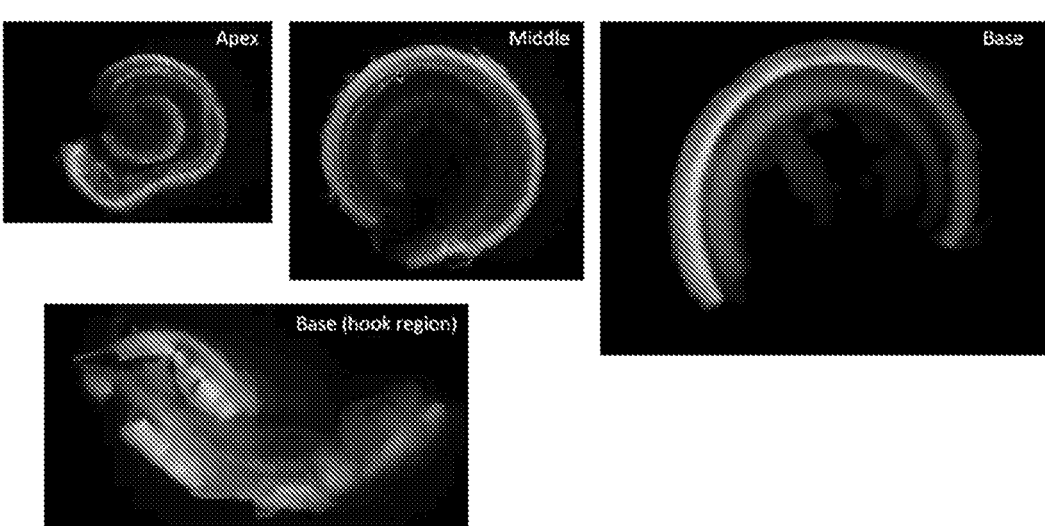
FIGS. 11A-C. Fluorescent images of cochlear turns (A), inner hair cells (B), organ of corti (C), and distal modiolus (C) following cochlear administration of AAV9 1999 capsids containing the eGFP construct to mice.
Figure 11B:
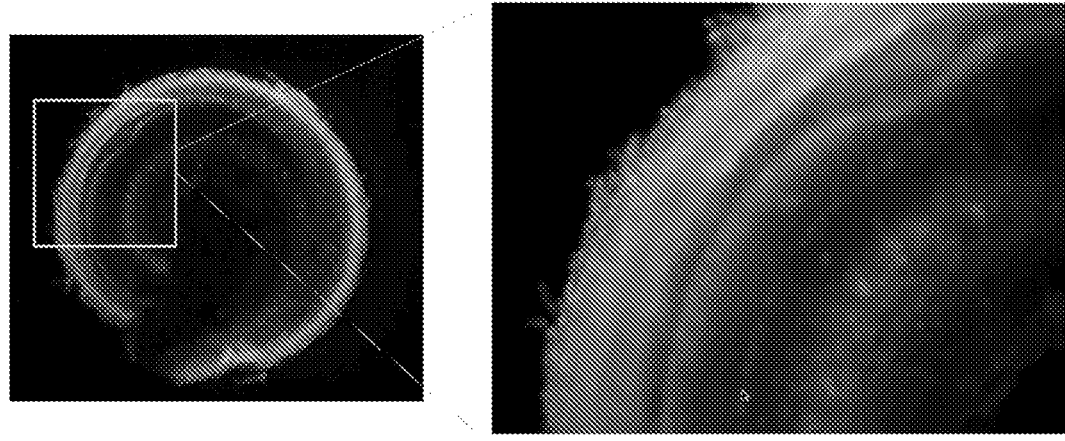
Figure 11C:
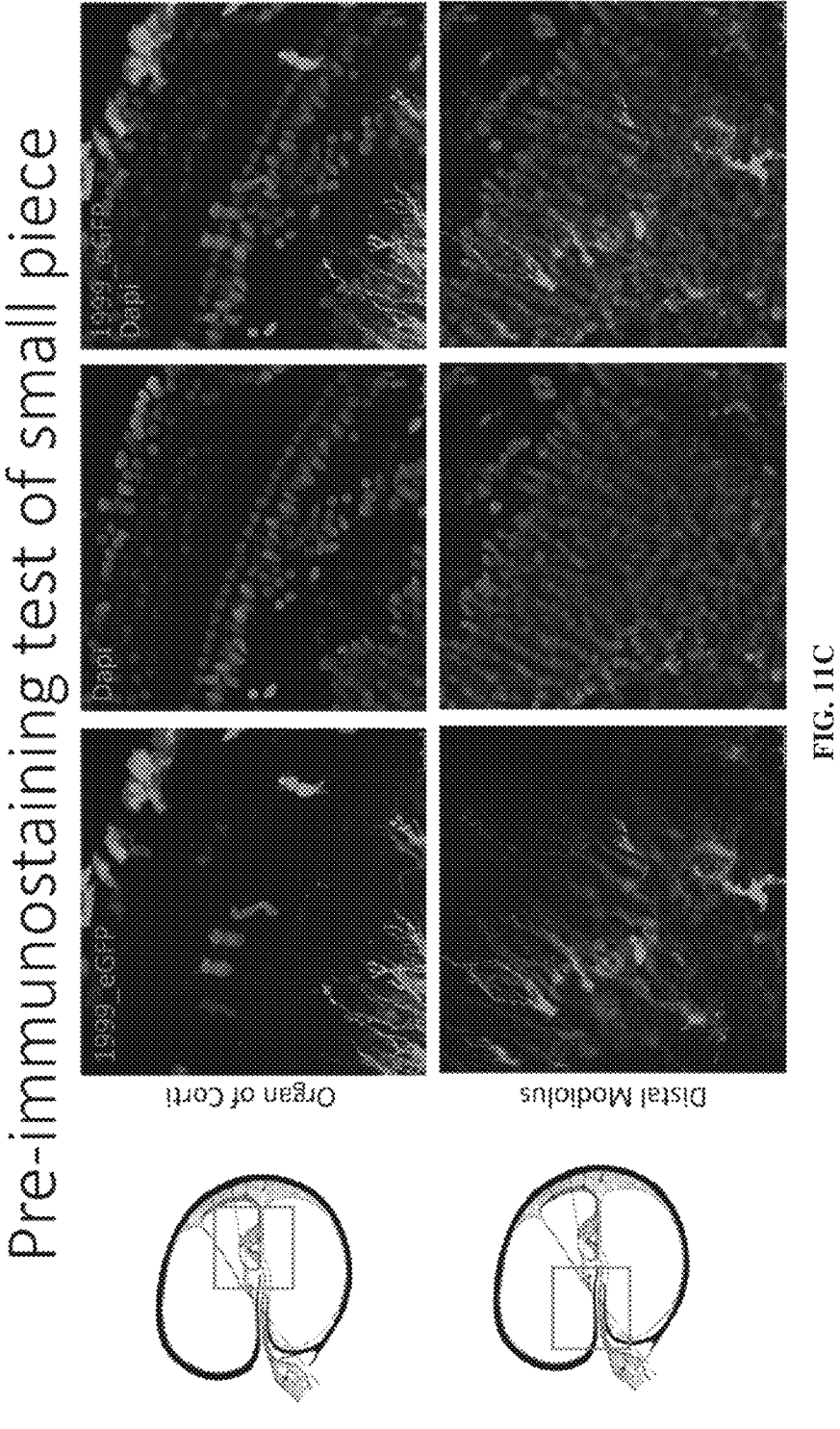

Additional experiments were performed by injecting the AAV9-1999 into the cochlea of rhesus macaques. Based on the results of cochlear transduction, an animal received AAV9-1999 to their lateral ventricle. A single animal received 3 E11 vg of AAV9-1999 injected directly to their round window with canal fenestrations (FIGS. 11A-C).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 8,299,215

U.S. Pat. No. 8,691,948

United States Patent Application Publication No. 2018/0142259

Chen et al., Molecular signatures of disease brain endothelia provide new sites for CNS-directed enzyme therapy. Nat Med, 2009. 15(10): p. 1215-8.

Chen et al., Overcoming Limitations Inherent in Sulfamidase to Improve Mucopolysaccharidosis IIIA Gene Therapy. Mol Ther, 2018. 26(4): p. 1118-1126.

Deverman et al., Cre-dependent selection yields AAV variants for widespread gene transfer to the adult brain. Nat Biotechnol, 2016. 34(2): p. 204-9.

Hartz et al., Isolation of Cerebral Capillaries from Fresh Human Brain Tissue. J Vis Exp, 2018(139).

Hordeaux et al., The Neurotropic Properties of AAV-PHP.B Are Limited to C57BL/6J Mice. Mol Ther, 2018. 26(3): p. 664-668.

Katz et al., AAV gene transfer delays disease onset in a TPP1-deficient canine model of the late infantile form of Batten disease. Sci Transl Med, 2015. 7(313): p. 313ra180.

Keiser et al., Broad distribution of ataxin 1 silencing in rhesus cerebella for spinocerebellar ataxia type 1 therapy. Brain, 2015. 138(Pt 12): p. 3555-66.

Koerber et al., DNA shuffling of adeno-associated virus yields functionally diverse viral progeny. Mol Ther, 2008. 16(10): p. 1703-9.

Matsuzaki et al., Intravenous administration of the adeno-associated virus-PHP.B capsid fails to upregulate transduction efficiency in the marmoset brain. Neurosci Lett, 2018. 665: p. 182-188.

McBride et al., Preclinical safety of RNAi-mediated HTT suppression in the rhesus macaque as a potential therapy for Huntington's disease. Mol Ther, 2011. 19(12): p. 2152-62.

Monteys et al., CRISPR/Cas9 Editing of the Mutant Huntingtin Allele In Vitro and In Vivo. Mol Ther, 2017. 25(1): p. 12-23.

Muller et al., Random peptide libraries displayed on adeno-associated virus to select for targeted gene therapy vectors. Nat Biotechnol, 2003. 21(9): p. 1040-6.

Schaffer & Maheshri, Directed evolution of AAV mutants for enhanced gene delivery. Conf Proc IEEE Eng Med Biol Soc, 2004. 5: p. 3520-3.

Zhong et al., Next generation of adeno-associated virus 2 vectors: point mutations in tyrosines lead to high-efficiency transduction at lower doses. Proc Natl Acad Sci USA, 2008. 105(22): p. 7827-32.

What is claimed is:

1. A modified adeno-associated (AAV) capsid protein comprising a targeting peptide that targets a viral vector comprising the modified AAV capsid protein to a distinct brain structure, wherein the targeting peptide is up to ten amino acids in length, wherein the targeting peptide comprises an amino acid sequence selected from the amino acid sequence of SEQ ID NOs: 110-137, wherein the modified AAV capsid protein is a modified AAV9 capsid protein having a sequence at least 95% identical to the amino acid sequence of SEQ ID NO: 143 and the targeting peptide is inserted after residue 591 of the amino acid sequence of SEQ ID NO: 143.

2. The modified AAV capsid protein of claim 1, wherein the distinct brain structure is the brainstem, caudate, cerebellar cortex, cerebral cortex, deep cerebellar nuclei, ependyma, globus pallidus, hippocampus, meninges, motor cortex, optic nerve, prefrontal cortex, putamen, spinal cord, substantia nigra, subthalamic nuclei, temporal cortex, thalamus, or visual cortex.

3. The modified AAV capsid protein of claim 1, wherein the targeting peptide is flanked by linker sequences, wherein the linker sequences on each side of the targeting peptides are two or three amino acids long.

4. The modified AAV capsid protein of claim 3, wherein the linker sequences are AAA on the N-terminal side of the targeting peptide and AS on the C-terminal side of the targeting peptide.

5. The modified AAV capsid protein of claim 1, wherein the targeting peptide is seven amino acids in length.

6. The modified AAV capsid protein of claim 1, wherein the distance brain structure is the brainstem, caudate, cerebellar cortex, cerebral cortex, deep cerebellar nuclei, ependyma, globus pallidus, hippocampus, meninges, motor cortex, optic nerve, prefrontal cortex, putamen, spinal cord, substantia nigra, subthalamic nuclei, temporal cortex, thalamus, or visual cortex.

7. The modified AAV capsid protein of claim 6, wherein the distinct brain structure is the brainstem, and wherein the targeting peptide is selected from SEQ ID NOs: 110-117.

8. The modified AAV capsid protein of claim 6, wherein the distinct brain structure is the caudate, and wherein the targeting peptide is selected from SEQ ID NOs: 110, 113, 115, 116, and 118-121.

9. The modified AAV capsid protein of claim 6, wherein the distinct brain structure is the cerebellar cortex, and wherein the targeting peptide is selected from SEQ ID NOs: 110, 111, 113, 119, and 122-125.

10. The modified AAV capsid protein of claim 6, wherein the distinct brain structure is the cerebral cortex, and wherein the targeting peptide is selected from SEQ ID NOs: 110, 111, 113, 114, 116, and 125-127.

11. The modified AAV capsid protein of claim 6, wherein the distinct brain structure is the ependyma, and wherein the targeting peptide is selected from SEQ ID NOs: 110, 111, 113, 118-120 and 128.

12. The modified AAV capsid protein of claim 6, wherein the distinct brain structure is the globus pallidus, and wherein the targeting peptide is selected from SEQ ID NOs: 110-112, 114, 119, 120, and 129.

13. The modified AAV capsid protein of claim 6, wherein the distinct brain structure is the hippocampus, and wherein the targeting peptide is selected from SEQ ID NOs: 110, 111, 113, 116, 123, 125, 129, and 130.

14. The modified AAV capsid protein of claim 6, wherein the distinct brain structure is the meninges, and wherein the targeting peptide is selected from SEQ ID NOs: 110, 111, 113, 114, 118, 119, 122, and 131.

15. The modified AAV capsid protein of claim 6, wherein the distinct brain structure is the optic nerve, and wherein the targeting peptide is selected from SEQ ID NOs: 110, 111, 114, 115, 117, 129, and 132.

16. The modified AAV capsid protein of claim 6, wherein the distinct brain structure is the putamen, and wherein the targeting peptide is selected from SEQ ID NOs: 110, 112, 113, 116, 123, 127, 133, and 134.

17. The modified AAV capsid protein of claim 6, wherein the distinct brain structure is the spinal cord, and wherein the targeting peptide is selected from SEQ ID NOs: 110, 113, 119, 120, 122, 123, 128, 134.

18. The modified AAV capsid protein of claim 6, wherein the distinct brain structure is the substantia nigra, and wherein the targeting peptide is selected from SEQ ID NOs: 110-114, 117, and 129.

19. The modified AAV capsid protein of claim 6, wherein the distinct brain structure is the subthalamic nuclei, and wherein the targeting peptide is selected from SEQ ID NOs: 110, 111, 113, 119, 120, 122, 132, and 135.

20. The modified AAV capsid protein of claim 6, wherein the distinct brain structure is the thalamus, and wherein the targeting peptide is selected from SEQ ID NOs: 110, 112-114, 125, 133, 136, and 137.

21. The modified AAV capsid protein of claim 1:

wherein the targeting peptide comprises the amino acid sequence of SEQ ID NO: 110 and wherein the modified AAV capsid protein comprises the amino acid sequence of SEQ ID NO: 143;

wherein the targeting peptide comprises the amino acid sequence of SEQ ID NO: 111 and wherein the modified AAV capsid protein comprises the amino acid sequence of SEQ ID NO: 143;

wherein the targeting peptide comprises the amino acid sequence of SEQ ID NO: 112 and wherein the modified AAV capsid protein comprises the amino acid sequence of SEQ ID NO: 143;

wherein the targeting peptide comprises the amino acid sequence of SEQ ID NO: 113 and wherein the modified AAV capsid protein comprises the amino acid sequence of SEQ ID NO: 143;

wherein the targeting peptide comprises the amino acid sequence of SEQ ID NO: 114 and wherein the modified AAV capsid protein comprises the amino acid sequence of SEQ ID NO: 143;

wherein the targeting peptide comprises the amino acid sequence of SEQ ID NO: 115 and wherein the modified AAV capsid protein comprises the amino acid sequence of SEQ ID NO: 143;

wherein the targeting peptide comprises the amino acid sequence of SEQ ID NO: 116 and wherein the modified AAV capsid protein comprises the amino acid sequence of SEQ ID NO: 143;

wherein the targeting peptide comprises the amino acid sequence of SEQ ID NO: 117 and wherein the modified AAV capsid protein comprises the amino acid sequence of SEQ ID NO: 143;

wherein the targeting peptide comprises the amino acid sequence of SEQ ID NO: 118 and wherein the modified AAV capsid protein comprises the amino acid sequence of SEQ ID NO: 143;

wherein the targeting peptide comprises the amino acid sequence of SEQ ID NO: 119 and wherein the modified AAV capsid protein comprises the amino acid sequence of SEQ ID NO: 143;

wherein the targeting peptide comprises the amino acid sequence of SEQ ID NO: 120 and wherein the modified AAV capsid protein comprises the amino acid sequence of SEQ ID NO: 143;

wherein the targeting peptide comprises the amino acid sequence of SEQ ID NO: 121 and wherein the modified AAV capsid protein comprises the amino acid sequence of SEQ ID NO: 143;

wherein the targeting peptide comprises the amino acid sequence of SEQ ID NO: 122 and wherein the modified AAV capsid protein comprises the amino acid sequence of SEQ ID NO: 143;

wherein the targeting peptide comprises the amino acid sequence of SEQ ID NO: 123 and wherein the modified AAV capsid protein comprises the amino acid sequence of SEQ ID NO: 143;

wherein the targeting peptide comprises the amino acid sequence of SEQ ID NO: 124 and wherein the modified AAV capsid protein comprises the amino acid sequence of SEQ ID NO: 143;

wherein the targeting peptide comprises the amino acid sequence of SEQ ID NO: 125 and wherein the modified AAV capsid protein comprises the amino acid sequence of SEQ ID NO: 143;

wherein the targeting peptide comprises the amino acid sequence of SEQ ID NO: 126 and wherein the modified AAV capsid protein comprises the amino acid sequence of SEQ ID NO: 143;

wherein the targeting peptide comprises the amino acid sequence of SEQ ID NO: 127 and wherein the modified AAV capsid protein comprises the amino acid sequence of SEQ ID NO: 143;

wherein the targeting peptide comprises the amino acid sequence of SEQ ID NO: 128 and wherein the modified AAV capsid protein comprises the amino acid sequence of SEQ ID NO: 143;

wherein the targeting peptide comprises the amino acid sequence of SEQ ID NO: 129 and wherein the modified AAV capsid protein comprises the amino acid sequence of SEQ ID NO: 143;

wherein the targeting peptide comprises the amino acid sequence of SEQ ID NO: 130 and wherein the modified AAV capsid protein comprises the amino acid sequence of SEQ ID NO: 143;

wherein the targeting peptide comprises the amino acid sequence of SEQ ID NO: 131 and wherein the modified AAV capsid protein comprises the amino acid sequence of SEQ ID NO: 143;

wherein the targeting peptide comprises the amino acid sequence of SEQ ID NO: 132 and wherein the modified AAV capsid protein comprises the amino acid sequence of SEQ ID NO: 143;

wherein the targeting peptide comprises the amino acid sequence of SEQ ID NO: 133 and wherein the modified AAV capsid protein comprises the amino acid sequence of SEQ ID NO: 143;

wherein the targeting peptide comprises the amino acid sequence of SEQ ID NO: 134 and wherein the modified AAV capsid protein comprises the amino acid sequence of SEQ ID NO: 143;

wherein the targeting peptide comprises the amino acid sequence of SEQ ID NO: 135 and wherein the modified AAV capsid protein comprises the amino acid sequence of SEQ ID NO: 143;

wherein the targeting peptide comprises the amino acid sequence of SEQ ID NO: 136 or 137 and wherein the modified AAV capsid protein comprises the amino acid sequence of SEQ ID NO: 143.

22. The modified AAV capsid protein of claim 1, wherein the targeting peptide comprises the amino acid sequence of SEQ ID NO: 110.

23. The modified AAV capsid protein of claim 1, wherein the targeting peptide comprises the amino acid sequence of SEQ ID NO: 113.

* * * * *